(12) United States Patent
Rohwer et al.

(10) Patent No.: US 11,975,035 B2
(45) Date of Patent: *May 7, 2024

(54) METHODS FOR TREATING MICROBIAL INFECTIONS USING CAUDOVIRALES BACTERIOPHAGES

(71) Applicants: SAN DIEGO STATE UNIVERSITY (SDSU) FOUNDATION, San Diego, CA (US); THE REGENTS OF THE UNIVERSITY OF CALIFORNIA, Oakland, CA (US)

(72) Inventors: Forest Rohwer, San Diego, CA (US); Jeremy J. Barr, San Diego, CA (US); J. Bruce German, San Diego, CA (US)

(73) Assignees: SAN DIEGO STATE UNIVERSITY (SDSU) FOUNDATION, San Diego, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 153 days.

This patent is subject to a terminal disclaimer.

(21) Appl. No.: 17/541,063

(22) Filed: Dec. 2, 2021

(65) Prior Publication Data

US 2022/0160799 A1 May 26, 2022

Related U.S. Application Data

(63) Continuation of application No. 15/528,354, filed as application No. PCT/US2015/061409 on Nov. 18, 2015, now Pat. No. 11,260,089.

(60) Provisional application No. 62/126,577, filed on Feb. 28, 2015, provisional application No. 62/082,074, filed on Nov. 19, 2014.

(51) Int. Cl.
| | | |
|---|---|---|
| A61K 35/76 | (2015.01) |
| A23C 7/04 | (2006.01) |
| A23C 9/152 | (2006.01) |
| A23C 9/158 | (2006.01) |
| A23C 9/20 | (2006.01) |
| A23C 13/12 | (2006.01) |
| A23K 20/10 | (2016.01) |
| A23L 2/52 | (2006.01) |
| A23L 33/00 | (2016.01) |
| A23L 33/10 | (2016.01) |
| A61K 45/06 | (2006.01) |

(52) U.S. Cl.
CPC ............ *A61K 35/76* (2013.01); *A23C 7/04* (2013.01); *A23C 9/152* (2013.01); *A23C 9/158* (2013.01); *A23C 9/206* (2013.01); *A23C 13/12* (2013.01); *A23K 20/10* (2016.05); *A23L 2/52* (2013.01); *A23L 33/10* (2016.08); *A23L 33/40* (2016.08); *A61K 45/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 7,435,434 B1 | 10/2008 | Bruessow et al. |
| 2007/0010001 A1 | 1/2007 | Bujanover |
| 2008/0038322 A1 | 2/2008 | Murthy et al. |

*Primary Examiner* — Nicole Kinsey White
(74) *Attorney, Agent, or Firm* — Gregory P. Einhorn; Greer, Burns & Crain, Ltd.

(57) ABSTRACT

Provided are compositions and methods for treating, ameliorating and preventing various infections, disorders and conditions in mammals, including genetically-predisposed and chronic disorders, where a microbial or bacterial flora is at least one causative or symptom-producing factor, where exemplary compositions are products of manufacture, a food, a drink, a nutraceutical, a dietary supplement, a formulation, a pharmaceutical or a pharmaceutical preparation comprising at least one or several of: a plurality of isolated, or substantially purified bacteriophages or prophages, or bacteriophage subunits, a milk, a milk product, milk lipid, milk fat globule (MFG) macromolecule, a milk mucin, a milk glycolipid, a milk free glycan, a milk mucin-like glycoprotein, a milk protein, a milk sugar or lactose, a milk fat or butterfat, a milk vitamin. In alternative embodiment, provided are compositions and methods for treating, preventing or ameliorating an infection, for example, an infection in the gastrointestinal tract, or bowel.

28 Claims, 30 Drawing Sheets

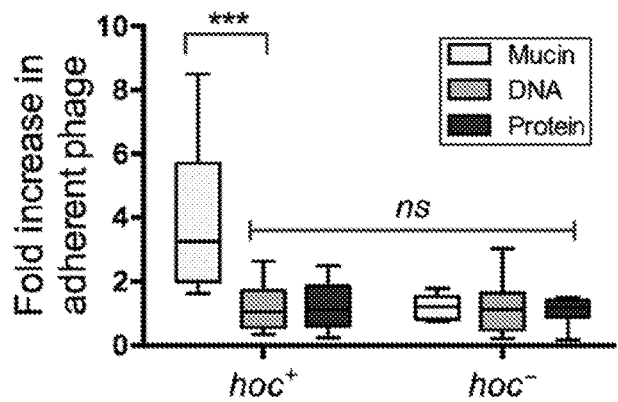
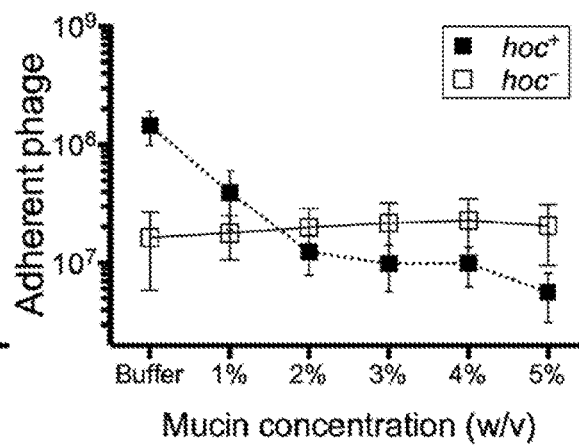
FIG. 3A
FIG. 3B
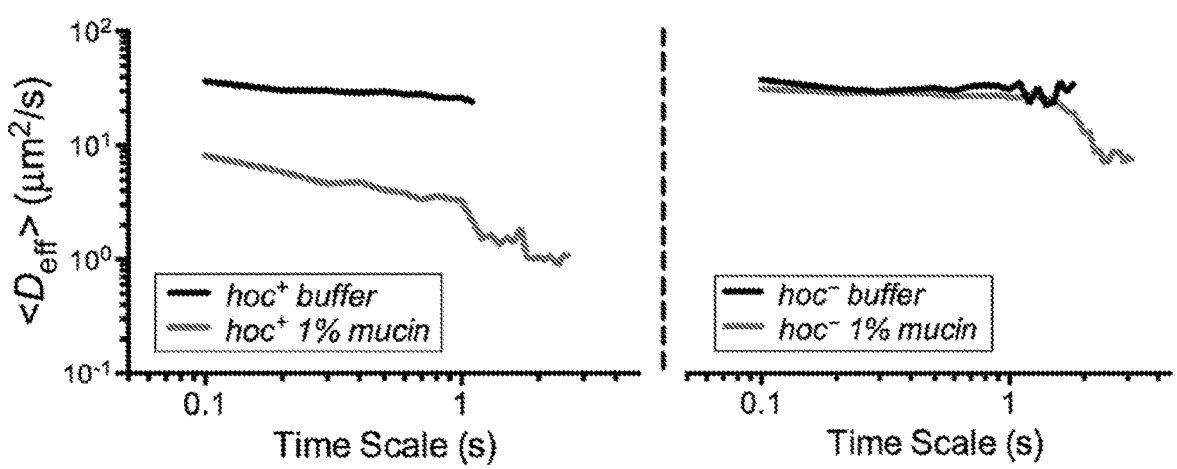
FIG. 3C

Composition of breast milk

Breast milk contains:
- Proteins
- Sugars
- Fats
- Vitamins
- Fatty acids

A number of active components:
- Enzymes
- Antibodies
- White blood cells

Table I Chemical composition of human milk compared with milk from various species (values per 100ml)

| Constituents | Human milk | Cow milk | Buffalo milk |
|---|---|---|---|
| Protein (g) | 1.2 | 3.3 | 3.8 |
| Casein (g) | 0.4 | 2.8 | 3.0 |
| Lactalbumin (g) | 0.3 | 0.4 | 0.4 |
| Lactoglobulin (g) | 0.2 | 0.2 | 0.2 |
| Fat (g) | 3.8 | 3.7 | 7.5 |
| Lactose (g) | 7.0 | 4.8 | 4.4 |
| Calorie (Kcal) | 71 | 69 | 100 |
| Mineral matter (g) | 0.21 | 0.72 | 0.80 |
| Calcium (mg) | 33 | 125 | 210 |
| Phosphorus (mg) | 15 | 96 | 130 |
| Chlorine (mg) | 43 | 103 | 112 |
| Magnesium (mg) | 4 | 12 | 15 |
| Potassium (mg) | 55 | 138 | 142 |
| Sodium (mg) | 15 | 58 | 65 |
| Iron (mg) | 0.15 | 0.10 | 0.20 |
| Copper (mg) | 0.04 | 0.03 | 0.02 |
| Magnesium (mg) | 0.7 | 2.0 | - |
| Zinc (mg) | 0.53 | 0.38 | - |
| Iodine (mg) | 0.007 | 0.021 | 0.004 |
| Vitamin A (IU) | 160 | 158 | 200 |
| Vitamin D (IU) | 1.4 | 2.0 | - |
| Thiamine (mg) | 0.017 | 0.04 | 0.05 |
| Riboflavin (mg) | 0.04 | 0.18 | 0.10 |
| Nicotinic acid (mg) | 0.17 | 0.08 | 0.28 |
| Pantothenic acid (mg) | 0.20 | 0.35 | - |
| Vitamin $B_4$ (mg) | 0.001 | 0.035 | - |
| Folic acid ($\mu$g) | 1.3 | 5.6 | 3.3 |
| Biotin ($\mu$g) | 0.4 | 2.0 | - |
| Vitamin $B_{12}$ ($\mu$g) | 0.03 | 0.50 | 0.30 |
| Vitamin C (mg) | 4.0 | 2.0 | 2.5 |

Source: Swaminathan (1994)

FIG. 6

Breast milk samples

Patient breast milk samples were non-sterilely collected by the mother and frozen.

- Samples were warmed to 37C
- Protease inhibitors added
- Samples were aliquot to smaller volumes for analysis

| Patient ID | Date | Day of Lactation | Mom Age | Infant Sex |
|---|---|---|---|---|
| 6001 | 5/9/11 | 72 | 28 | F |
| 6002 | 9/2/11 | 126 | MISSING | MISSING |
| 6003 | 8/20/10 | 70 | 32 | M |
| 6011 | 5/2/11 | 146 | 31 | F |
| 6014 | 10/13/12 | 294 | 26 | M |

FIG. 8

Sequencing the milk virome

Obtained breast milk from 21 mothers → 1 mL milk collected → Samples purified for VLP, DNA extracted, phizg amplified → Multiplex sequenced on Illumin MiSeq

| Patient ID | Milk | Infant Stool | Mom age | Birth mode | Infant sex | Mastitis | Antibiotics |
|---|---|---|---|---|---|---|---|
| 1002 | d6, d42 | d42 | 27 | V | M | | |
| 1006 | d6, d42 | d42 | 26 | V | F | | |
| 1010 | d6, d42 | d42 | 28 | V | M | | d0 |
| 1011 | d6, d42 | d42 | 30 | V | F | | |
| 1013 | d6, d42 | d42 | 32 | V | M | | |
| 1016 | d6, d42 | d42 | 31 | V | F | | |
| 1019 | d6, d42 | d42 | 28 | V | F | | |
| 1021 | d6, d42 | d42 | 31 | V | M | | |
| 1025 | d6, d42 | d42 | 31 | C | M | | |
| 1028 | d6, d42 | d42 | 30 | V | F | | |
| 1029 | d6, d42 | d42 | 38 | V | F | | |
| 1031 | d6, d42 | d42 | 28 | V | M | | d5-26 |
| 1033 | d6, d42 | d42 | 35 | V | F | | |
| 1034 | d6, d42 | d42 | 33 | V | M | d14-d21 | d21 |
| 1037 | d6, d42 | d42 | 28 | V | M | | |
| 1040 | d6, d42 | d42 | 27 | V | F | | |
| 1044 | d6, d42 | d42 | 45 | V | F | | |
| 1050 | d6, d42 | d42 | 32 | V | M | d35 | d30-37 |
| 1053 | d6, d42 | d42 | 26 | V | F | d35 | d30-42 |
| 1060 | d6, d42 | d42 | 34 | V | F | | |
| 1065 | d6, d42 | d42 | 33 | V | F | | d15-21 |

FIG. 10

What is the role of phage in milk?

*Breast milk transmits microbes to the infant gut epithelium, does it also transmit phage?*

First barrier to phage is the stomach!

- Fasting gastric pH 3.1–3.4
- Phage are stable over pH range 5–8

*Adams 1959.*

- During first 10 min of breast feeding, gastric pH increased to 5.1–6.0

*Armand 1996. Pediatric Research*

FIG. 11

Phage adherence to milk

Needed to further test this increase in adherence across our five patient sample set.

| Patient ID | Date | Day of Lactation | Mom Age | Infant Sex |
|---|---|---|---|---|
| 6001 | 5/9/11 | 72 | 28 | F |
| 6002 | 9/2/11 | 126 | MISSING | MISSING |
| 6003 | 8/20/10 | 70 | 32 | M |
| 6011 | 5/2/11 | 146 | 31 | F |
| 6014 | 10/13/12 | 294 | 26 | M |

FIG. 15

Affect of MFG on phage adherence

MFG separation
1. MFG was isolated from raw breast milk by low centrifugation (600 RPM for 5min)
2. MFG collected at top of milk as a fat layer
3. Skim milk was collected from the lower fraction

- MFG were then mixed with Skim milk at varying ratios to test affect on page adherence Cream Layer (contains MFG)

Skim Milk (MFG depleted)

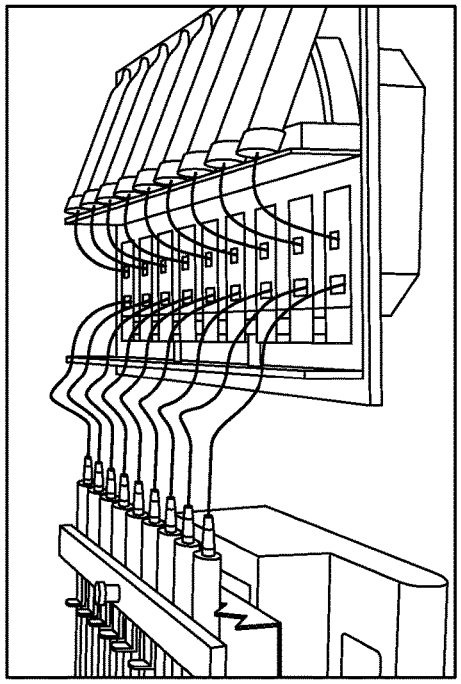
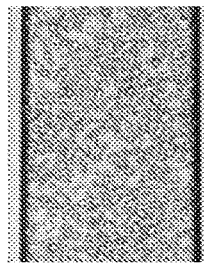
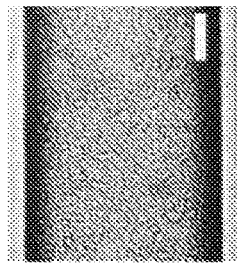
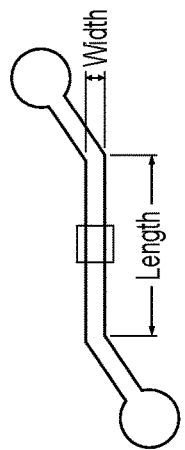
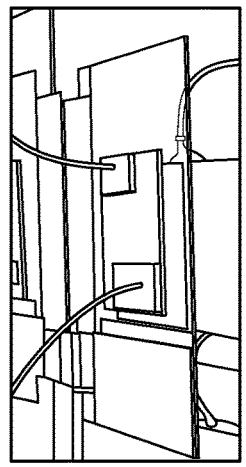
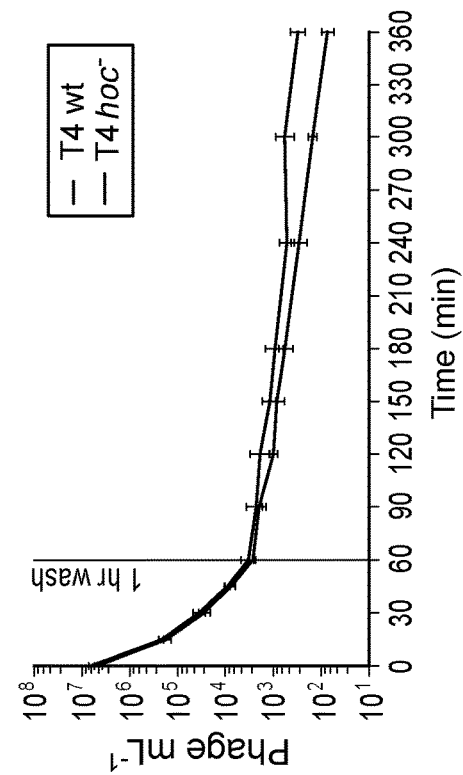
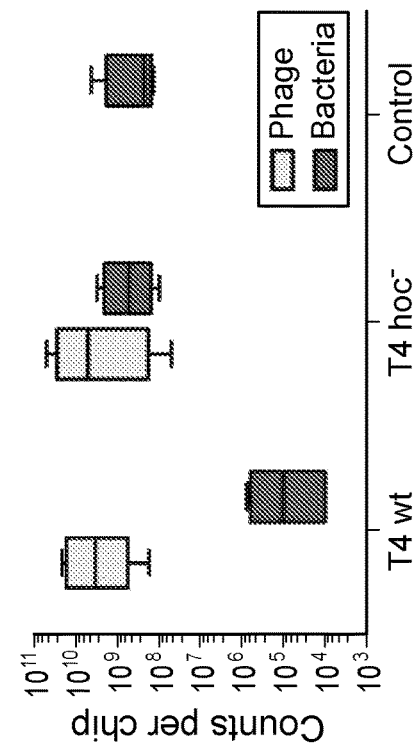

| Glycan# | Structure | Linkage | T4 RFU | T4 %CV | hoc- RFU | hoc-%CV |
|---|---|---|---|---|---|---|
| 609 | GlcNAcb1-3Fuca | -N(CH3)-O-(CH2)2-NH2 | 4921 | 3 | 394 | 16 |
| 610 | Galb1-3GalNAcb1-4(Neu5Aca2-8Neu5Aca2-8Neu5Aca2-3)Galb1-4Glcb | -N(CH3)-O-(CH2)2-NH2 | 4685 | 11 | 472 | 13 |
| 573 | Neu5Aca2-8Neu5Aca2-3Galb1-3GalNAcb1-4(Neu5Aca2-3)Galb1-4Glc | -N(CH3)-O-(CH2)2-NH2 | 4161 | 1 | 316 | 11 |
| 608 | Neu5Aca2-6Galb1-4GlcNAcb1-3Galb1-4GlcNAcb1-2Mana1-6(Neu5Aca2-6Galb1-4GlcNAcb1-3Galb1-4GlcNAcb1-2Mana1-3)Manb1-4GlcNAcb1-4GlcNAcb | Asparagine | 4685 | 4 | 497 | 17 |
| 145 | Galb1-3GalNAcb1-4Galb1-4Glcb | CH2CH2CH2NH2 | 5823 | 3 | 565 | 7 |
| 195 | Glca1-4Glcb | CH2CH2CH2NH2 | 5845 | 1 | 544 | 3 |
| 514 | GalNAcb1-4(6S)GlcNAc | CH2CH2CH2NH2 | 4818 | 6 | 568 | 17 |
| 287 | Neu5Gca | CH2CH2CH2NH2 | 4182 | 3 | 356 | 9 |
| 119 | Gala1-4(Fuca1-2)Galb1-4GlcNAcb | CH2CH2CH2NH2 | 4157 | 3 | 331 | 8 |
| 336 | GalNAca1-3(Fuca1-2)Galb1-4GlcNAcb1-3Galb1-4GlcNAcb | CH2CH2NH2 | 7670 | 31 | 472 | 51 |
| 217 | Manb1-4GlcNAcb | CH2CH2NH2 | 4766 | 3 | 647 | 24 |
| 144 | Galb1-3GalNAcb1-4(Neu5Aca2-3)Galb1-4Glcb | CH2CH2NH2 | 4797 | 4 | 589 | 26 |
| 517 | Galb1-4(6P)GlcNAcb | CH2CH2NH2 | 4751 | 11 | 526 | 20 |
| 218 | Neu5Aca2-3Galb1-4GlcNAcb1-3Galb1-4(Fuca1-3)GalNAca | CH2CH2NH2 | 4737 | 3 | 322 | 10 |
| 334 | GalNAcb1-3Gala1-4Galb1-4GlcNAcb1-3Galb1-4Glcb | CH2CH2NH2 | 4261 | 4 | 499 | 8 |
| 143 | Galb1-3GalNAcb1-3Glca1-4Glca1-4Glcb | CH2CH2NH2 | 4236 | 1 | 451 | 13 |

FIG. 28A

| | | | | |
|---|---|---|---|---|
| 581 | Galb1-4GlcNAcb1-3Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-3Galb1- | EN or NK | 5465 | 6 | 262 | 7 |
| 360 | Fuca1-2Galb1-3GlcNAcb1-2Mana1-6(Fuca1-2Galb1-3GlcNAcb1-2Mana1-3)Manb1-4GlcNAcb1-4GlcNAcb | GENR | 4914 | 2 | 482 | 12 |
| 588 | Galb1-4GlcNAcb1-3Galb1-4GlcNAcb1-3Galb1-4GlcNAcb1-3Galb1-4GlcNAcb1-6(Galb1-4GlcNAcb1-3Galb1-4GlcNAcb1-3Galb1-4GlcNAcb1-3Galb1-4GlcNAb1-2)Mana1-6(Galb1-4GlcNAcb1-3Galb1-4GlcNAcb1-3Galb1-4GlcNAcb1-3Galb1-4GlcNAcb1-2Mana1-3)Manb1-4GlcNAcb1-4(Fuca1-6)GlcNAcb | KVANKT | 3926 | 2 | 154 | 5 |
| 470 | Glca1-4Glca1-4Glcb | NHCOCH2NH | 7521 | 10 | 1288 | 17 |
| 516 | (4S)GalNAcb | NHCOCH2NH | 6148 | 2 | 464 | 3 |
| 359 | KDNa2-3Galb1-3GalNAca | Threonine (O-linked glycan) | 7484 | 17 | 1080 | 24 |
| 471 | Neu5Aca2-3Galb1-4GlcNAcb1-6(Neu5Aca2-3Galb1-4GlcNAcb1-3)GalNAca | Threonine (O-linked glycan) | 5877 | 6 | 585 | 2 |
| 491 | Neu5Aca2-3Galb1-3GlcNAcb1-6GalNAca | Threonine (O-linked glycan) | 4755 | 2 | 394 | 8 |
| 596 | Neu5Aca2-3Galb1-4GlcNAcb1-6Galb1-4GlcNAcb1-6(Neu5Aca2-3Galb1-4GlcNAcb1-3)GalNAca | Threonine (O-linked glycan) | 4703 | 14 | 242 | 7 |
| 595 | GlcNAcb1-3Galb1-4GlcNAcb1-6(GlcNAcb1-3Galb1-4GlcNAcb1-3)GalNAca | Threonine (O-linked glycan) | 4653 | 1 | 392 | 9 |
| 605 | Neu5Aca2-6Galb1-4GlcNAcb1-3Galb1-4GlcNAcb1-6(Neu5Aca2-6Galb1-4GlcNAcb1-3)GalNAca | Threonine (O-linked glycan) | 4078 | 1 | 410 | 10 |
| 480 | Neu5Aca2-6Galb1-4GlcNAcb1-6GalNAca | Threonine (O-linked glycan) | 4143 | 5 | 301 | 20 |
| 592 | Neu5Aca2-6Galb1-4GlcNAcb1-3Galb1-4GlcNAcb1-3GalNAca | Threonine (O-linked glycan) | 4200 | 11 | 266 | 11 |

FIG. 28B

METHODS FOR TREATING MICROBIAL INFECTIONS USING CAUDOVIRALES BACTERIOPHAGES

RELATED APPLICATIONS

This U.S. utility patent application is a continuation of U.S. utility patent application Ser. No. 15/528,354, filed May 19, 2017, now U.S. Pat. No. 11,260.089, issue date Mar. 1, 2022, which is a national phase application claiming benefit of priority under 35 U.S.C. § 371 to Patent Convention Treaty (PCT) International Application Ser. No; PCT/US2015/061409, filed Nov. 18, 2015, which claims benefit of priority under 35 U.S.C. § 119(e) of U.S. provisional patent application Ser. No. 62/082,074, filed Nov. 19, 2014, and U.S. Ser. No. 62/126,577, filed on Feb. 28, 2015. The aforementioned applications are expressly incorporated herein by reference in their entirety and for all purposes.

STATEMENT AS TO FEDERALLY SPONSORED RESEARCH

This invention was made with government support under grant numbers NIH R01: GM095384, and NTH R21: AT094534, awarded by the National Institute of General Medical, National Institutes of Health (NIH), DHHS. The government has certain rights in the invention.

TECHNICAL FIELD

This invention generally relates to medicine, infectious diseases, pharmacology and microbiology. In alternative embodiments, provided are compositions and methods for treating, ameliorating and preventing various infections, disorders and conditions in mammals, including genetically-predisposed and chronic disorders, where a microbial or bacterial flora is at least one causative or symptom-producing factor, where exemplary compositions as provided herein are products of manufacture, a food, a drink, a nutraceutical, a formulation, a pharmaceutical or a pharmaceutical preparation comprising at least one or several of: a plurality of isolated, or substantially purified bacteriophages, or bacteriophage subunits, a milk, a milk product, milk lipid, milk fat globule (MFG) macromolecule, a milk mucin, a milk glycolipid, a milk free glycan, a milk mucin-like glycoprotein, a milk protein, a milk sugar or lactose, a milk fat or butterfat, a milk vitamin, or equivalents thereof, or a mixture thereof. In alternative embodiment, provided are compositions and methods for treating, preventing or ameliorating an infection, for example, an infection in the gastrointestinal tract, or bowel. In alternative embodiments, provided are compositions and methods using bacteriophage or bacteriophages subunits for targeting specific infectious agents or pathogens, for example, bacteria.

BACKGROUND

Mucosal surfaces are the primary zones where animals meet their environment, and thus also the main points of entry for pathogenic microorganisms. The mucus layer is heavily colonized by bacterial symbionts that provide additional genetic and metabolic potentials to the host (1, 2). Bacterial symbionts are associated with a variety of host surfaces, providing beneficial goods and services, e.g., nutrients (3-6), bioluminescence (7, 8), and antibiotics (9, 10). The resident symbiotic bacteria benefit from the available nutrients, as well as the opportunity for both vertical transmission and increased dissemination (11-13).

Within the mucus, the predominant macromolecules are the large (up to $10^6$-$10^9$ Da) mucin glycoproteins. The amino acid backbone of these proteins incorporates tandem repeats of exposed hydrophobic regions alternating with blocks with extensive O-linked glycosylation (14). Hundreds of variable, branched, negatively-charged glycan chains extend 0.5-5 nm from the peptide core outward into the surrounding environment (14, 15). In addition to mucins, DNA, proteins and other cellular debris are also present. Continual secretion and shedding of mucins maintains a protective mucus layer from 10 to 700 μm thick, depending on species and body location (16-19).

By offering both structure and nutrients, mucus layers commonly support higher bacterial concentrations than the surrounding environment (20, 21). Secretions produced by the underlying epithelium influence the composition of this microbiota (22-24). Of necessity, hosts employ a variety of mechanisms to limit microbial colonization (23, 25-27). When invaded by pathogens, the epithelium may respond by increased production of anti-microbial agents, hypersecretion of mucin, or alteration of mucin glycosylation patterns to subvert microbial attachment (28-30).

Also present in the mucus environment are bacteriophage (phage), the most common and diverse biological entities. As specific bacterial predators, they increase microbial diversity through Red Queen/Kill-the-Winner dynamics (31, 32). Many phages instead establish symbiotic relationships with their bacterial hosts through lysogeny. As integrated prophages they often express genes that increase host fitness or virulence (33-35) and protect their host from lysis by related phages. As free phages they aid their host strain by killing competing strains (36-38). Phages participate, along with their bacterial hosts, in tripartite symbioses with metazoans that affect metazoan fitness (39-42). However, no direct symbiotic interactions between phage and metazoans are known.

Recently, Minot et al. showed that phages in the human gut encode a population of hypervariable proteins (43). For 29 hypervariable regions, evidence indicated that hypervariability was conferred by targeted mutagenesis through a reverse transcription mechanism (43, 44). Approximately half of these encoded proteins (14) possessed the C-type lectin fold previously found in the major tropism determinant protein at the tip of the *Bordetella* phage BPP-1 tail fibers (45); six others contained Ig-like domains. These Ig-like proteins, similar to antibodies and T-cell receptors, can accommodate large sequence variation (>$10^{13}$ potential alternatives) (46). Immunoglobulin-like (Ig-like) domains are also displayed in the structural proteins of many phage (47, 48). That most of these displayed Ig-like domains are dispensable for phage growth in the laboratory (44, 48) led to the hypothesis that they aid adsorption to their bacterial prey under environmental conditions (48). The possible role and function of these hypervariable proteins remain to be clarified.

SUMMARY

In alternative embodiments, provided are products of manufacture, foods or feeds, dietary supplements, drinks, nutraceuticals, formulations (e.g., infant formulations), pharmaceuticals and pharmaceutical preparations comprising a plurality of isolated, or substantially purified bacteriophages or prophages formulated with: (a) a milk, wherein optionally the milk is a human milk; (b) a milk product comprising a milk lipid, a milk fat globule (MFG) macromolecule, a mucin found in a milk (a milk mucin), a glycolipid found in a milk (a milk glycolipid), a free glycan found in a milk (a milk free glycan), a mucin-like glycoprotein found in a milk (a milk mucin-like glycoprotein), a milk protein (e.g., a casein, a casein micelle, or a whey, e.g., a beta-lactoglobulin or an alpha-lactalbumin), a milk sugar or a lactose, a milk fat or a butterfat (e.g., a saturated fatty acid, e.g., a Palmitic acid, a Myristic acid, a Stearic acid, a lower e.g., less than 12 carbon, saturated fatty acids, a pentadecanoic acid, or a heptadecanoic acid; or, an unsaturated fatty acid, e.g., an Oleic acid, a Palmitoleic acid, a Linoleic acid or an alpha-Linolenic acid), a milk vitamin (e.g., water soluble vitamins thiamin (vitamin B1), riboflavin (vitamin B2), niacin (vitamin B3), pantothenic acid (vitamin B5), vitamin B6 (pyridoxine), vitamin B12 (cobalamin), vitamin C (L-ascorbic acid) or folate) and fat soluble vitamin, e.g., a vitamin A, a vitamin D (e.g., a secosteroid, a calcidiol, a hydroxycholecalciferol or a cholecalciferol), a vitamin E (e.g., a tocopherol or a tocotrienol), or a vitamin K (e.g., a phylloquinone, a phytomenadione, or a phytonadione)), or equivalents thereof, or a mixture thereof; (c) an isolated, or substantially purified: milk lipid, milk fat globule (MFG) macromolecule, mucin found in a milk (a milk mucin), glycolipid found in a milk (a milk glycolipid), free glycan found in a milk (a milk free glycan), mucin-like glycoprotein found in a milk (a milk mucin-like glycoprotein), milk protein, milk sugar or lactose, milk fat or butterfat, milk vitamin, or equivalents thereof, or a mixture thereof; (d) a liposome or a micelle, a hydrogel (e.g., a biocompatible crosslinked degradable thiol-ene polymer) a dendrimer, a particle or a microparticle (e.g., a biodegradable polymeric particle, e.g., a poly(lactic acid) (PLA), a poly(glycolic acid)- (PGA)- or a poly(lactic-co-glycolic acid) (PLGA)-comprising particle), a powder, a nanostructure or a nanoparticle comprising a component of any of (a), (b) or (c); or (e) a poly(lactic-co-glycolic acid) (PLGA); a poly(lactic acid) (PLA); a poly(glycolic acid); a poly(vinyl alcohol)(PVA); a poly(ethylene glycol)(PEG); a poly(ethylene oxide); a poly(ethylene oxide)-co-poly(propylene oxide) block copolymer; a polyoxamine; a polyanhydride; a polyorthoester; a poly(hydroxyl acids); a polydioxanone; a polycarbonate; a polyaminocarbonate; a poly(vinyl pyrrolidone; a poly(ethyl oxazoline); a carboxymethyl cellulose; a hydroxyalkylated cellulose; a heparin sulfate, a chondroitin sulfate, a heparin, an alginate, a gelatin, a collagen, a albumin, a ovalbumin, or equivalents thereof, or a mixture thereof; or (f) any combination of the plurality of isolated, or substantially purified bacteriophages or prophages with (a), (b), (c), (d) and/or (e) thereof.

In alternative embodiments, provided are products of manufacture, foods or feeds, drinks, nutraceuticals, dietary supplements, formulations (e.g., infant formulations), pharmaceuticals and pharmaceutical preparations comprising:

(a) a plurality of isolated, or substantially purified bacteriophages or prophages,
  wherein optionally the prophage is an extrachromosomal plasmid form, or is integrated into the genome of a microorganism, optionally a bacteria, optionally a probiotic bacterium;

(b) a milk or a cream,
  wherein optionally the milk is a mammalian or a human milk, and optionally the milk is a skim milk or a whole (full) milk;

(c) a milk product, milk component or milk isolate comprising: a milk lipid, a milk fat globule (MFG) macromolecule (including intact, e.g., non-pasteurized) milk fat globules (MFGs), which comprise e.g., the cream fraction of milk and fat droplets which are stabilized by an external membrane derived mainly from the apical plasma membrane of mammary secretory cells), a mucin found in a milk (a milk mucin), a glycolipid found in a milk (a milk glycolipid), a free glycan found in a milk (a milk free glycan), a mucin-like glycoprotein found in a milk (a milk mucin-like glycoprotein), a milk protein (e.g., a casein, a casein micelle, or a whey, e.g., a beta-lactoglobulin or an alpha-lactalbumin), a milk sugar or a lactose, a milk fat or a butterfat (e.g., a saturated fatty acid, e.g., a Palmitic acid, a Myristic acid, a Stearic acid, a lower e.g., less than 12 carbon, saturated fatty acids, a pentadecanoic acid, or a heptadecanoic acid; or, an unsaturated fatty acid, e.g., an Oleic acid, a Palmitoleic acid, a Linoleic acid or an alpha-Linolenic acid), a milk vitamin (e.g., water soluble vitamins thiamin (vitamin B1), riboflavin (vitamin B2), niacin (vitamin B3), pantothenic acid (vitamin B5), vitamin B6 (pyridoxine), vitamin B12 (cobalamin), vitamin C (L-ascorbic acid) or folate) and fat soluble vitamin, e.g., a vitamin A, a vitamin D (e.g., a secosteroid, a calcidiol, a hydroxycholecalciferol or a cholecalciferol), a vitamin E (e.g., a tocopherol or a tocotrienol), or a vitamin K (e.g., a phylloquinone, a phytomenadione, or a phytonadione)), or equivalents thereof, or a mixture thereof;

(d) an isolated, or substantially purified: milk lipid, milk fat globule (MFG) macromolecule, mucin found in a milk (a milk mucin), glycolipid found in a milk (a milk glycolipid), free glycan found in a milk (a milk free glycan), mucin-like glycoprotein found in a milk (a milk mucin-like glycoprotein), milk protein, milk sugar or lactose, milk fat or butterfat, milk vitamin, or equivalents thereof, or a mixture thereof;

(c) a liposome or a micelle, a plasma membrane, or component of a plasma membrane (optionally a bacterial plasma membrane), a hydrogel (e.g., a biocompatible crosslinked degradable thiol-ene polymer) a dendrimer, a particle or a microparticle (e.g., a biodegradable polymeric particle, e.g., a poly(lactic acid) (PLA), a poly(glycolic acid)- (PGA)- or a poly(lactic-co-glycolic acid) (PLGA)-comprising particle), a powder, a nanostructure or a nanoparticle comprising a component of any of (a), (b), (c) or (d),
  wherein optionally the plasma membrane, or component of a plasma membrane, is reconstituted as a globular particle of a specific size range, optionally having a size of between about: 1 nm to 100 nm, 100 nm to 1000 nm, 1 um to 100 um, or 100 um to 1000 um,
  and optionally the plasma membrane component comprises a milk fat globule membrane, another lipid bilayer, another lipid bilayer comprising and displaying a mucin or a negatively charged glycan;

(f) a poly(lactic-co-glycolic acid) (PLGA); a poly(lactic acid) (PLA); a poly(glycolic acid); a poly(vinyl alcohol) (PVA); a poly(ethylene glycol)(PEG); a poly(ethylene oxide); a poly(ethylene oxide)-co-poly(propylene oxide) block copolymer; a polyoxamine; a polyanhydride; a polyorthoester; a poly(hydroxyl acids); a polydioxanone; a polycarbonate; a polyaminocarbonate; a poly(vinyl pyrrolidone; a poly(ethyl oxazoline); a carboxymethyl cellulose; a hydroxyalkylated cellulose; a heparin sulfate, a chondroitin sulfate, a heparin, an alginate, a gelatin, a collagen, a albumin, a ovalbumin, or equivalents thereof, or a mixture thereof;

(g) the combination of: (a) and (b): (a) and (c); (a) and (d); (a) and (e); (a) and (f); (a) and (g); (a), (b) and (e); (a), (b) and (f); (a), (c) and (e); (a), (c) and (f); (a), (d) and (e); or (a), (d) and (f); or (h) any combination thereof, wherein optionally the mucin comprises a membrane-tethered, membrane-integrated or secreted mucin, and optionally the mucin comprises a MUC1, MUC3A, MUC3B, MUC4, MUC10, MUC11, MUC12, MUC13, MUC14, MUC15, MUC16, MUC17, MUC18, MUC20, MUC21, MUC2, MUC5AC, MUC5B, MUC6, MUC7, MUC8, MUC9, MUC19, and optionally the glycan is an O-linked glycosylated glycan, an optionally a glycan with O-linked GalNAc or N-linked glycosylation, and optionally a glycan as set forth in FIG. 28.

In alternative embodiments, the plurality of isolated, or substantially purified bacteriophages or prophages are selected from the group consisting of:

(a) a plurality of isolated, or substantially purified bacteriophages or prophages derived from a mammal, wherein optionally the mammal is human;

(b) a plurality of isolated, or substantially purified bacteriophages or prophages derived or isolated from milk of a mammal, wherein optionally the mammal milk is a human milk;

(c) a plurality of isolated, or substantially purified bacteriophages or prophages from the order Caudovirales or Ligamenvirales;

(d) a plurality of isolated, or substantially purified bacteriophages or prophages from the family Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globuloviridae, Guttaviridaelnoviridae, Leviviridae, Microviridae, Plasmaviridae or a combination thereof;

(e) a plurality of isolated, or substantially purified bacteriophages or prophages known or demonstrated to be toxic or lysogenic to a bacteria, or is bacteriocidal or bacteriostatic, or can treat, inhibit or prevent an infection (optionally a microbial or a bacterial infection), wherein optionally the bacteriophages or prophages are bacteriocidal or bacteriostatic to gram negative bacteria or gram positive bacteria, optionally the bacteria or infection is or is caused by an MSRA infection, a *Staphylococcus*, a *Staphylococcus aureus*, a *Clostridium*, or a *Clostridium difficile*, *Escherichia coli*, a *Shigella*, a *Salmonella*, a *Campylobacter*, a Cholerae, a *Bacillus*, or a *Yersinia*;

(f) a plurality of isolated, or substantially purified bacteriophages or prophages made by a process comprising: screening a plurality of bacteriophages or prophages for bacteriocidal or bacteriostatic properties against a bacteria of interest, and selecting the bacteriophages or prophages having a lysogenic or a bacteriocidal or bacteriostatic activity;

(g) a plurality of isolated or substantially purified temperate phage, optionally a phage or prophage that are either integrated or excised from a bacteria, optionally a probiotic bacteria; or (f) any combination thereof.

In alternative embodiments: (a) the bacteriophage or prophage are isolated or substantially purified based on the bacteriophage or prophage having the following properties; or, the bacteriophage or prophage are characterized as having the following properties: having a cesium chloride density between 1.5 to 1.7 g/mL, being resistant to lysis by chloroform, having a particle size between about 0.01 and 0.2 μm, between about 0.005 and 0.5 μm or between about 0.001 and 0.8 μm, and being detectable via dsDNA fluorescence stain; or, (b) the bacteriophage or prophage are formulated per dose, or per serving, or per unit dosage at, or at a total daily dose of: between about $10(1)$ (or $10^1$) and $10(20)$ plaque-forming units (PFUs), or between about $10(3)$ and $10(17)$ PFUs, or between about $10(5)$ and $10(12)$ PFUs, or between about $10(7)$ and $10(9)$ PFUs.

In alternative embodiments, the products of manufacture, foods or feeds, dietary supplements, drinks, nutraceuticals, formulations (e.g., infant formulations), pharmaceuticals and pharmaceutical preparations further comprise: an additional active agent or pharmaceutical or pharmaceutical preparation, wherein optionally the additional pharmaceutical or pharmaceutical preparation comprises an antibiotic, and optionally the additional active agent comprises a microorganism, optionally a bacteria or a yeast, optionally a probiotic bacteria, and optionally the additional active agent comprises a probiotic, a prebiotic, a postbiotic, or a synbiotic, and optionally the prebiotic comprises a nondigestible oligosaccharide, optionally an inulin, a fructan, a xylose, a maltose, a mannose, or a fructooligosaccharide, and optionally the probiotic bacteria comprise: a *Bacillus* or a *Lactobacillus*; or, a *Bacillus coagulans*, a *Lactobacillus acidophilus*, a *Lactobacillus plantarum* or a *Lactobacillus rhamnosus*, and optionally the yeast comprises a *Saccharomyces*; or a *Saccharomyces boulardii*.

In alternative embodiments, the products of manufacture, foods or feeds, dietary supplements, drinks, nutraceuticals, formulations (e.g., infant formulations), pharmaceuticals and pharmaceutical preparations are manufactured, formulated, dosaged and/or packaged for administration in vivo; or for enteral or parenteral administration, or for ophthalmic, topical, oral, intranasal, intrarectal, intravaginal, intravenous, intra-peritoneal, intraocular, intra-placental, intrabladder, cutaneous, intravenous (IV), intramuscular (IM), intrathecal, subcutaneous (SC), intracerebral, epidural, intracranial or rectal administration, or by inhalation.

In alternative embodiments, the products of manufacture, foods or feeds, dietary supplements, drinks, nutraceuticals, formulations (e.g., infant formulations), pharmaceuticals and pharmaceutical preparations are formulated, dosaged, manufactured as or placed or formulated into: (a) a particle, a nanoparticle, a liposome, a tablet, a pill, a capsule, a gel, a geltab, a liquid, a powder, a suspension, a syrup, an emulsion, a lotion, an ointment, an aerosol, a spray, a lozenge, an ophthalmic preparation, an aqueous or a sterile or an injectable solution, a patch (optionally a transdermal patch or a medicated adhesive patch), an implant, a dietary supplement, an ice cream, an ice, a yogurt, a cheese, an infant formula or infant dietary supplement, a pasteurized milk or milk product or milk-comprising product; or, (b) a veterinary formulations or feed, or as dietary supplements.

In alternative embodiments, the products of manufacture, foods or feeds, dietary supplements, drinks, nutraceuticals, formulations (e.g., infant formulations), pharmaceuticals and pharmaceutical preparations further comprise, or have added to:

a pharmaceutically acceptable excipient.

a flavoring or a sweetening agent, an aspartamine, a stevia, monk fruit, a sucralose, a saccharin, a cyclamate, a xylitol, a vanilla, an artificial vanilla or chocolate or strawberry flavor, an artificial chocolate essence, or a mixture or combination thereof.

a preservative, a benzoic acid, a potassium sorbate.

at least one probiotic or prebiotic, wherein optionally the prebiotic comprises an inulin, lactulose, extracts of artichoke, chicory root, oats, barley, various legumes, garlic, kale, beans or flacks or an herb, at least one congealing agent, wherein optionally the congealing agent comprises an arrowroot or a plant starch, a powdered flour, a powdered potato or potato starch, an absorbent polymer, an ABSORBABLE MODIFIED POLY- MER™ (AMP®), ENDOCLOT™, Santa Clara, Calif.), and/or a corn flour or a corn starch.

at least one an anti-inflammatory agent, wherein optionally the inflammatory agent comprises or is an NSAID, a 4 or a 5-amino-salicylate, an olsalazine, a mesalazine, a sulfasalazine and/or a balsalazide or an equivalent thereof or a combination thereof.

an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supplement, or a prebiotic nutrient, and optionally the buffer or a buffering agent or the pharmaceutically acceptable excipient comprises an inorganic salt, a citric acid, a sodium chloride, a potassium chloride, a sodium sulfate, a potassium nitrate, a sodium phosphate monobasic, a sodium phosphate dibasic or combinations thereof, and optionally the antacid comprises a calcium carbonate, a magnesium hydroxide, a magnesium oxide, a magnesium carbonate, an aluminum hydroxide, a sodium bicarbonate or a dihydroxyaluminum sodium carbonate; or any combination thereof.

In alternative embodiments, the products of manufacture, foods or feeds, dietary supplements, drinks, nutraceuticals, formulations (e.g., infant formulations), pharmaceuticals and pharmaceutical preparations are manufactured, processed, isolated, treated, formulated or prepared:

(a) as a delayed or gradual enteric release composition or formulation, and optionally the formulation comprises a gastro-resistant coating designed to dissolve at a pH of 7 in the terminal ileum, e.g., an active ingredient is coated with an acrylic based resin or equivalent, e.g., a poly(meth)acrylate, e.g. a methacrylic acid copolymer B, NF, such as EUDRAGIT S™ (Evonik Industries AG, Essen, Germany), which dissolves at pH 7 or greater, e.g., comprises a multimatrix (MMX) formulation; or (b) by treating the milk, the cream, the milk product, the milk component or the milk isolate, or a component of (1)(a), (1)(b), (1)(c), (1)(d), (1)(e) or (1)(f), to a process selected from the group consisting of: aeration, agitation, stirring, pumping, shaking, rocking, centrifugation, temperature, incubation, drying, ageing, pasteurizing, homogenizing, coagulation, chemical addition, bacterial growth, flow cytometry, particle size selection, fluorescent tagging or labelling, rheology, microscopy, micromanipulation, microfluidics, density gradients, gel electrophoresis, column filtration and any combination thereof.

In alternative embodiments, the milk, the cream, the milk product, the milk component or the milk isolate is isolated, processed, manufactured, or derived from:

(a) a mammal ranging in age from between about 1 to 3 years, 3 to 5 years, or 5 to 10 years of age;

(b) a mammal ranging in age from between about 1 to 30 days postnatal, 30 to 90 days postnatal, or 90 to 360 postnatal;

(c) a mammal during a specific season or month of the year;

(d) a mammal fed on a diet or feed: high in fat, protein and/or carbohydrate content;

(e) a mammal bred to increase a specific component of milk or cream; or (f) a specific breed of mammal or individual animal that is infected, diseased, or suffering from a mastitis, clinical and non-clinical.

In alternative embodiments, the milk, the cream, the milk product, the milk component or the milk isolate comprises, or consists of, components having a particle size between about: 0.1 nm to 10.0 nm, 1 nm to 100 nm, 100 nm to 1000 nm, 1 um to 100 um, or 100 um to 1000 um.

In alternative embodiments, the milk, the cream, the milk product, the milk component or the milk isolate comprises between about 0.01% to 1%, 1% to 20%, or 20% to 100% of the food or a feed, drink, nutraceutical, formulation, pharmaceutical or pharmaceutical preparation.

In alternative embodiments, provided are delivery vehicles, products of manufacture, containers, syringes, devices or implants, comprising: foods or feeds, drinks, dietary supplements, nutraceuticals, formulations, freeze-dried compositions, an infant formula, pharmaceuticals or pharmaceutical preparations comprising, consisting of or having contained therein or being packaged or stored therein one or more or a plurality of compositions as provided herein, e.g., products of manufacture, foods or feeds, dietary supplements, drinks, nutraceuticals, formulations (e.g., infant formulations), pharmaceuticals and pharmaceutical preparations as described herein.

In alternative embodiments, provided are products of manufacture, liquids, suspensions, gels, geltabs, a semisolid, a tablet, a sachet, a lozenge or a capsule, a freeze-dried composition, an infant formula, or an enteral or parenteral formulation, comprising: food or a feed, drink, nutraceutical, formulation, pharmaceutical or pharmaceutical preparation as provided herein, e.g., one or more or a plurality of compositions as described herein.

In alternative embodiments, provided are methods for:
 treating, ameliorating and preventing a microbial or a bacterial infection,
 increasing or decreasing an effective dose of a probiotic, a prebiotic, a postbiotic or a synbiotic;
 increasing or decreasing efficacy of a probiotic, a prebiotic, a postbiotic or a synbiotic attaching to mucosal surfaces;
 increasing or decreasing access of a probiotic, a prebiotic, a postbiotic or a synbiotic to mucosal surfaces;
 increasing or decreasing chance of an enteral or gastrointestinal pathogenic infection or disease; or
 increasing or decreasing resistance of a probiotic, a prebiotic, a postbiotic or a synbiotic to temperature, pH, mechanical stress, osmotic stress and/or gastrointestinal enzymes,
comprising administering, feeding or applying to an individual in need thereof:
 (a) a product of manufacture, food or a feed, drink, nutraceutical, formulation, pharmaceutical or pharmaceutical preparation as provided herein, or as described herein;
 (b) a delivery vehicle, a product of manufacture, a container, a syringe, device or an implant as provided herein, or as described herein; or
 (c) liquid, a suspension, a gel, a geltab, a semisolid, a tablet, a sachet, a lozenge or a capsule, a freeze-dried composition, an infant formula, or an enteral or parenteral formulation, comprising: food or a feed, drink, nutraceutical, formulation as provided herein, or as described herein,
 wherein optionally the individual is a mammal, and optionally the mammal is a human, or a human infant,
 and optionally an antacid or a buffer or buffering agent or a pharmaceutically acceptable excipient is administered before, during or after, or before and during, administration of the product of manufacture, food or a feed, drink, nutraceutical, formulation, pharmaceutical or pharmaceutical preparation of (a), and optionally sufficient amount of antacid, buffer or buffering agent is administered (optionally before, during or after, or before and during, administration) to raise the pH of the stomach in the individual to between about 2.5 and 7, or between about 3 and 6.5, or to about 5.0, 5.5, 6.0, 6.5, 6.8 or 7.0 (optionally these pH values reached before, during or after, or before and during, administration), and optionally the buffer or a buffering agent or the pharmaceutically acceptable excipient comprises an inorganic salt, a citric acid, a sodium chloride, a potassium chloride, a sodium sulfate, a potassium nitrate, a sodium phosphate monobasic, a sodium phosphate dibasic or combinations thereof, and optionally the antacid comprises a calcium carbonate, a magnesium hydroxide, a magnesium oxide, a magnesium carbonate, an aluminum hydroxide, a sodium bicarbonate or a dihydroxyaluminum sodium carbonate.

In alternative embodiments, provided are Uses of:

(a) a product of manufacture, a food or a feed, a drink, a nutraceutical, a formulation, a pharmaceutical or a pharmaceutical preparation as provided herein, or as described herein;

(b) a delivery vehicle, a product of manufacture, a container, a syringe, device or an implant as provided herein, or as described herein; or (c) a liquid, a suspension, a gel, a geltab, a semisolid, a tablet, a sachet, a lozenge or a capsule, a freeze-dried composition, an infant formula, or an enteral or parenteral formulation, comprising: food or a feed, drink, nutraceutical, formulation as provided herein, or as described herein, for:
treating, ameliorating and preventing a microbial or a bacterial infection, increasing or decreasing an effective dose of a probiotic, a prebiotic, a postbiotic or a synbiotic;

increasing or decreasing efficacy of a probiotic, a prebiotic, a postbiotic or a synbiotic attaching to mucosal surfaces;

increasing or decreasing access of a probiotic, a prebiotic, a postbiotic or a synbiotic to mucosal surfaces;

increasing or decreasing chance of an enteral or gastrointestinal pathogenic infection or disease; or increasing or decreasing resistance of a probiotic, a prebiotic, a postbiotic or a synbiotic to temperature, pH, mechanical stress, osmotic stress and/or gastrointestinal enzymes.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments as provided herein and are not meant to limit the scope of the invention as encompassed by the claims.

FIG. 1a, Phage-to-bacteria ratio (PBR) for diverse mucosal surfaces and the adjacent environment. On average, PBRs for mucosal surfaces were 4.4-fold greater than for the adjacent environment (n=9, t=4.719 *P=0.0002, unpaired t test); FIG. 1b, Phage adherence to TC cell monolayers, with and without surface mucus (unpaired t tests). (left) Non-mucus producing Huh-7 liver hepatocyte cells and mucus-producing T84 colon epithelial cells (n>18, t=8.366, P<0.0001); (center) mucus-producing A549 lung epithelial cells with and without treatment with NAC, a mucolytic agent (n>40, t=9.561, P<0.0001); (right) mucus-producing shRNA control A549 cells (shControl) and mucus-knockdown (MUC$^-$) A549 cells (n>37, t=7.673, P<0.0001); FIG. 1c, Phage adherence to agar plates coated with mucin, DNA, or protein and an uncoated agar control (n=12, t=5.306, **P<0.0001, unpaired t test); as further discussed in Example 1, below.

FIG. 2a, Bacterial attachment to mucus producing (T84 and A549) and non-mucus producing (Huh-7, MUC$^-$) TC cells, with and without phage pretreatment. Phage pretreatment significantly decreased subsequent bacterial adherence to mucus-producing TC cell lines (T84; n>30, t=32.05, **P<0.0001, A549; n>30, t=36.85, P<0.0001, unpaired t tests). Less dramatic shifts were seen for non-mucus producing cells (Huh-7; n>30, t=2.72, P=0.0098, MUC$^-$; n>30, t=3.52, *P=0.0007, unpaired t tests). FIG. 2b, Mortality of mucus-producing (A549) and mucus knockdown (MUC$^-$) A549 lung epithelial cells following overnight incubation with E. coli (ns=not significant). Phage pretreatment completely protected mucus-producing A549 cells from bacterial challenge (n=12, **P<0.0001, Tukey's one-way ANOVA), while phage comparatively protected MUC$^-$ cells 3.1-fold less (n=12, *P=0.0181); as further discussed in Example 1, below.

FIG. 3a, FIG. 3b, FIG. 3c graphically illustrate data showing the effect of Hoc protein on phage-mucin interactions. FIG. 3a, Adherence of hoc$^+$ and hoc$^-$ T4 phage to agar coated with mucin, DNA, or protein versus plain agar controls (n>11, t=3.977, ***P=0.0007, unpaired t test). FIG. 3b, Competitive adherence of hoc$^+$ and hoc$^-$ T4 phage in 0%-5% mucin solutions that were washed over mucus-producing A549 cells (n=25 per sample). FIG. 3c, Diffusion of fluorescence-labeled hoc$^+$ (left) and hoc$^-$ (right) T4 phage in buffer and 1% mucin as determined by multiple particle tracking. Mucin hindered diffusion of hoc$^+$ T4 phage but not hoc$^-$ phage (ten analyses per sample, trajectories of n>100 particles for each analysis); as further discussed in Example 1, below.

FIG. 4a, Phylogenetic tree of sequences from viral metagenomes with high sequence homology to Ig-like domains; many of these homologs are from mucus-associated environments (e.g., human feces, sputum); also included are T4 Hoc and hypervariable Ig-like domains previously obtained by deep sequencing of phage from the human gut (7). Scale bar represents an estimated 0.5 amino acid substitutions per site; FIG. 4b, Binding of fluorescence stained hoc$^+$ and hoc$^-$ T4 phage to a microarray of 610 mammalian glycans; Normalized relative fluorescence units (RFU) were calculated from mean fluorescence minus background binding; as further discussed in Example 1, below.

Phage interact weakly with variable glycan residues displayed on mucin glycoproteins, via variable capsid proteins (e.g., Ig-like domains). 3) Phage adherence creates an antimicrobial layer that reduces bacterial attachment to and colonization of the mucus, which in turn lessens epithelium cell death. 4) Since phage are more likely to encounter bacterial hosts in the mucus, they are under positive selection for capsid proteins that enable them to maintain in the mucus layer; thus phage rapidly adapt to variable mucus glycans. 5) Continual sloughing of the outer mucus provides a dynamic mucosal environment; as further discussed in Example 1, below.

FIG. 6 illustrates a table showing the composition of a breast milk.

Figures 7A, 7B, 7C:

FIG. 7A, FIG. 7B and FIG. 7C schematically illustrate (FIG. 7A) and by illustrating images (FIG. 7B and FIG. 7C) describe and illustrate compounds found in breast milk.

Figure 9:
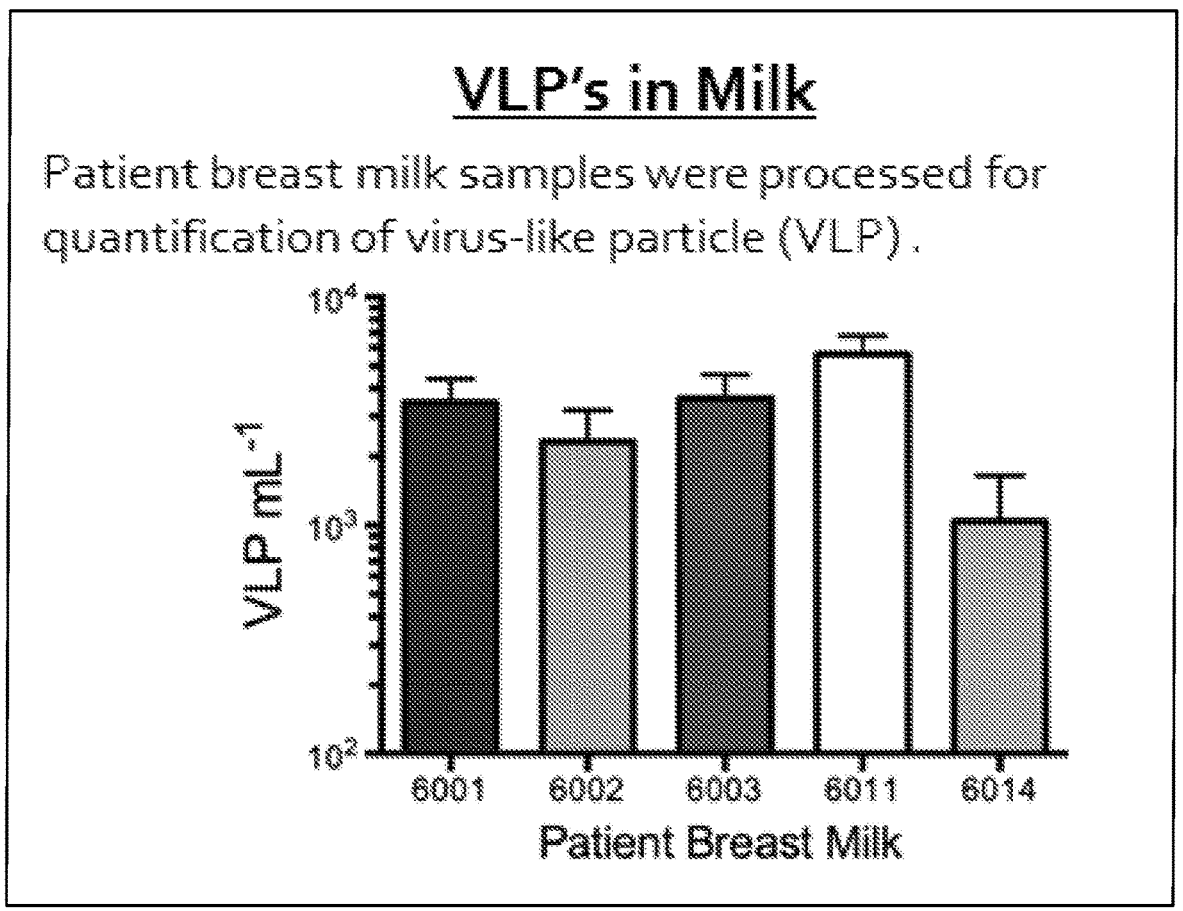

FIG. 8 illustrates a table showing and describing how breast milk samples were collected and from whom, to analyze Virus-Like Particles (VLPs) in human breast milk to characterize a human breast milk virome population, for analysis as shown in FIG. 9 and FIG. 10.

FIG. 9 graphically illustrates quantification of VLPs from human breast milk.

FIG. 10 illustrates a table showing how the sequencing of the VLPs collected from human breast milk as illustrated in FIG. 9 was done.

FIG. 11 illustrates and describes possible avenues of transmission of phage from human breast milk to an infant gut epithelium.

Figure 12:
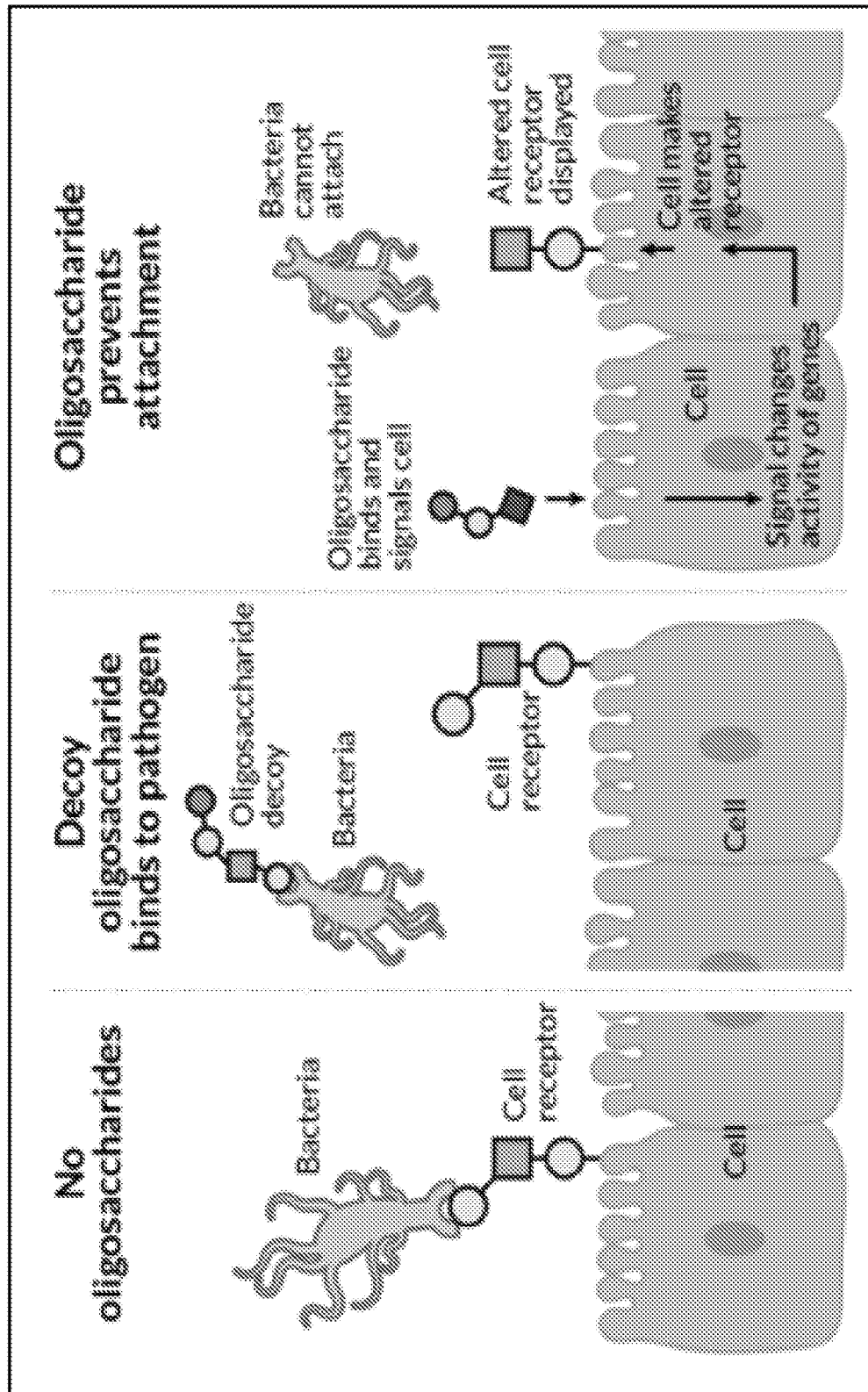

FIG. 12 schematically illustrates how breast milk oligosaccharides bind to bacteria, which can be pathogens, and this binding preventing the bacteria from attaching to gut cells of the gut cell wall, and that the oligosaccharides also can directly bind to the cell wall and alter what cell receptors are displayed in the gut lumen.

Figure 13:
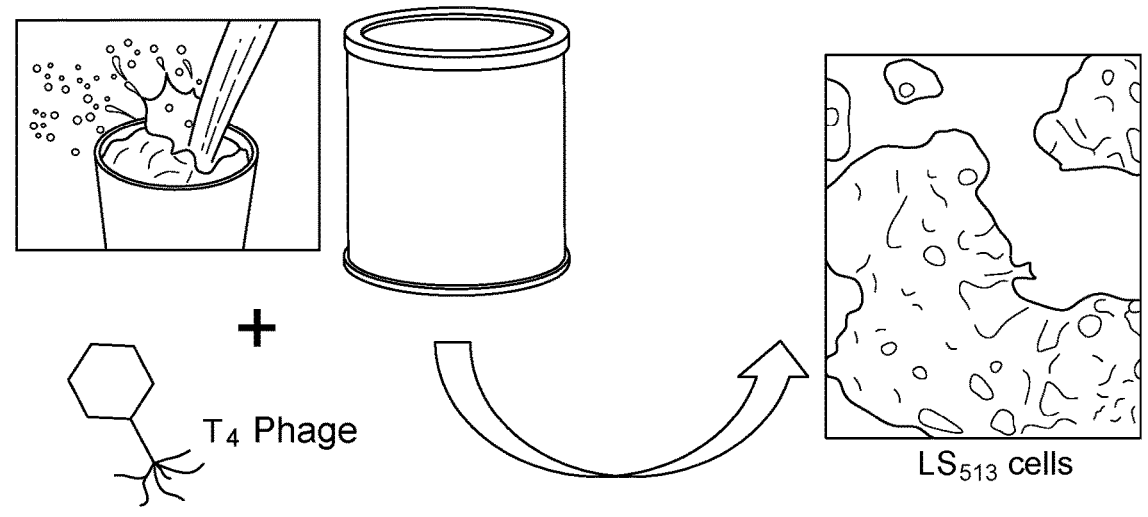

FIG. 13 schematically illustrates and describes an experimental setup to determine and quantify if milk (breast milk oligosaccharides) bind to (or associate with after washing) phage and/or adheres to cultured gut epithelial cells, and illustrates an image of phage adhering to an epithelial cell, in particular, the mucous-producing adherent cultured LS513 epithelial cell.

Figure 14:
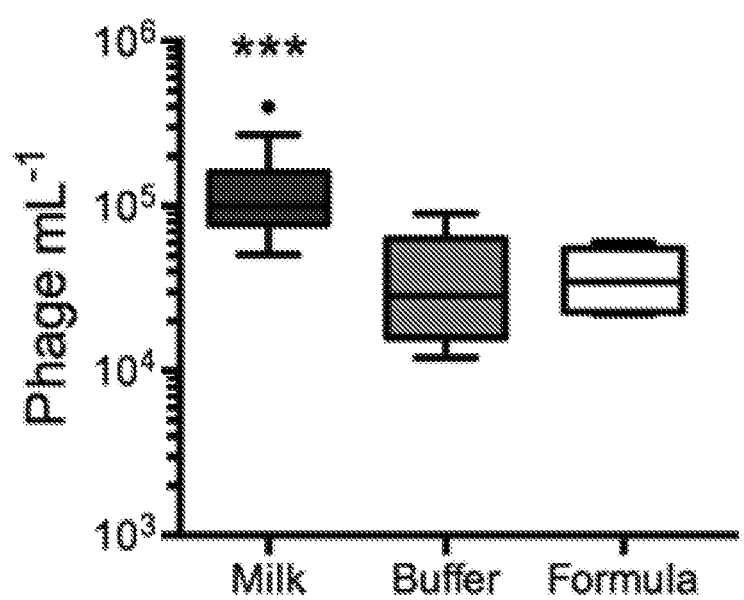

FIG. 14 graphically illustrates quantification of phage adherence to adherent cultured LS513 epithelial cells using the protocol of FIG. 13, where T4 phage were mixed with milk, buffer or formula, added to the cultured adherent cells, incubated, the cells then washed, and the adherent cells quantified by plaque forming units (PFU), and the data shows that there is a greater amount of phage binding to (or associated with after washing) adherent cells in the milk fraction as compared to the formula or buffer fractions.

FIG. 15 illustrates a table describing from whom breast milk sample was collected to analyze phage adherence to human breast milk and gut epithelium.

Figure 16:
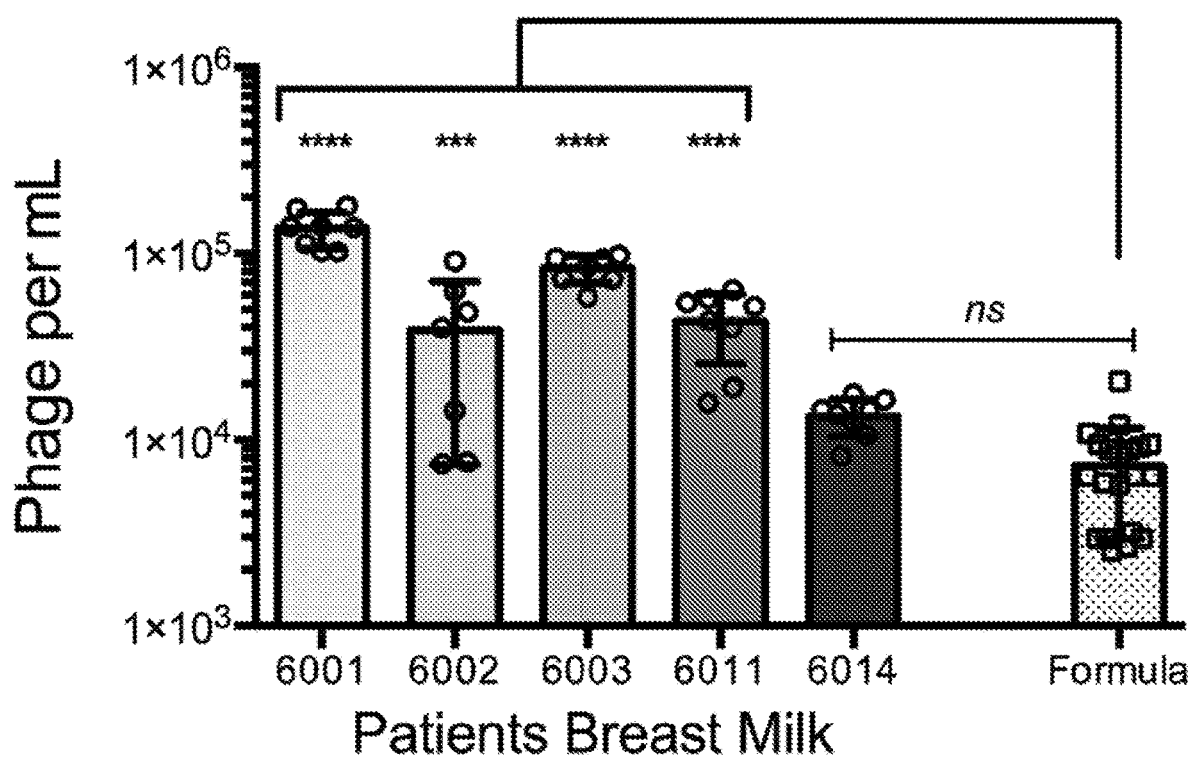

FIG. 16 graphically illustrates quantification of phage adherence to adherent cultured LS513 epithelial cells as for FIG. 13 and FIG. 14, and shows that there is a greater amount of phage binding to (or associated with after washing) the LS513 epithelial cells as compared to formula.

Figure 17A:
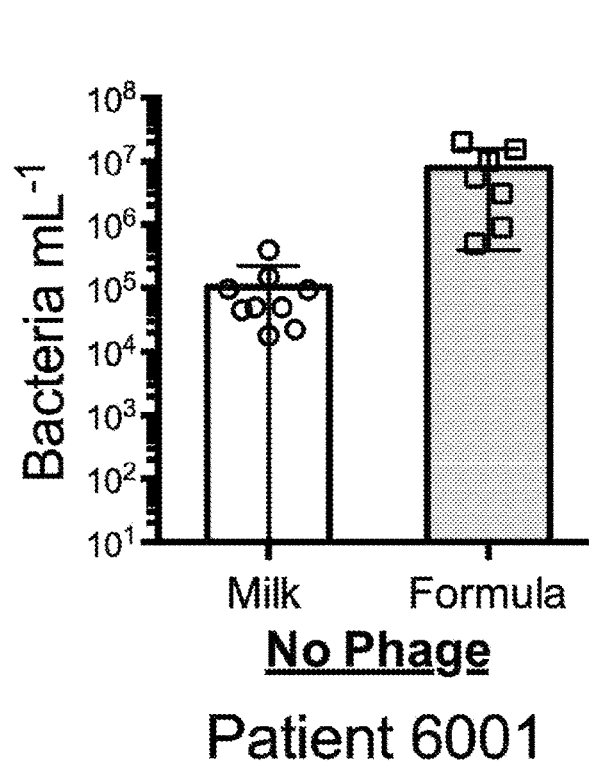
Figure 17B:
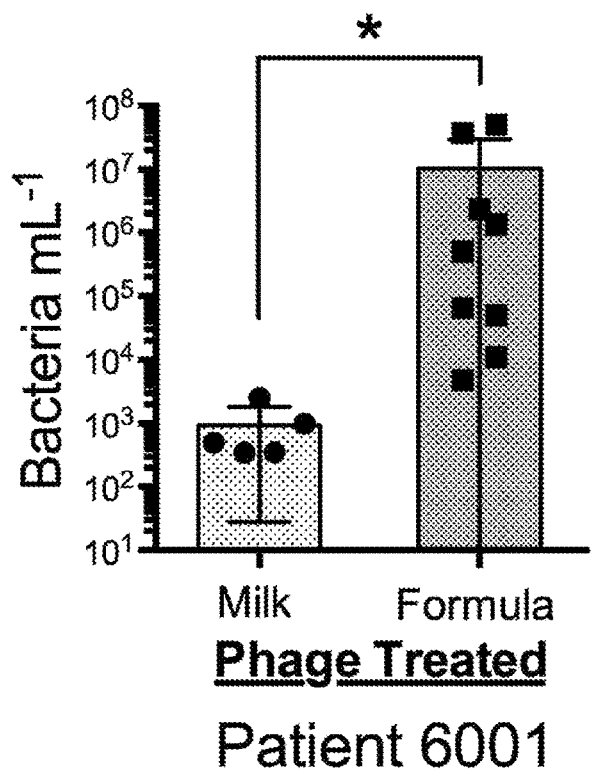

FIG. 17A and FIG. 17B graphically illustrate quantification of bacteria to adherent cultured LS513 epithelial cells, and the data shows: FIG. 17A data illustrates that in the "bacteria/no phage" sample there are fewer bacteria adherent to (associated with after washing) the LS513 epithelial cells in the milk fraction versus the formula fraction; and FIG. 17B illustrates that in the "bacteria/with phage" sample there are even fewer bacteria adherent to (associated with after washing) the LS513 epithelial cells in the milk fraction versus the formula fraction, demonstrating that the "phage and milk" fraction is most effective in reducing bacterial adherence to the epithelial cells.

Figure 18:
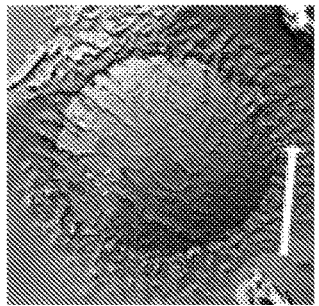

FIG. 18 illustrates an image, and describes, a milk fat globule (MFG) containing a triglyceride core coated by a lipid bilayer that displays mucins (as indicated by the arrow), and that the MFG is covered or layered by negatively charged mucins, and notes that formula does not contain mucin-comprising MFGs, thus suggesting that the mucin component of the MFG of milk may be responsible for increasing the effectiveness of the "phage and milk" fraction in preventing bacterial adherence to the LS513 epithelial cells as found in the study of FIG. 17.

Figure 19:
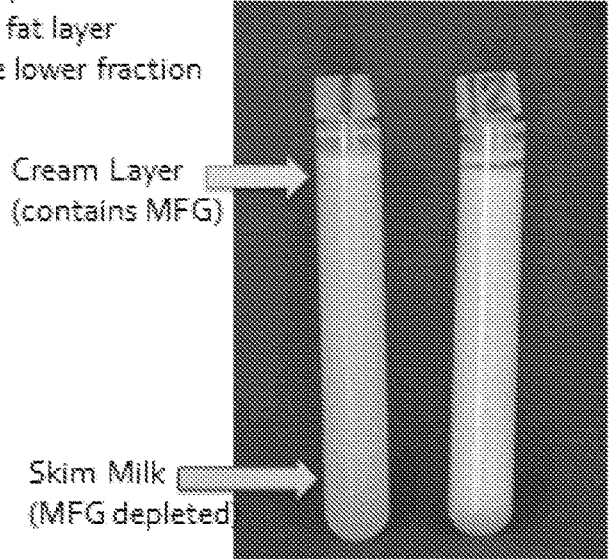

FIG. 19 illustrates an image, and describes, MFG separation from raw breast milk by low centrifugation, the illustrated figure showing an MFG-enriched "cream layer" and an MFG-depleted "skim milk" layer.

Figure 20A:
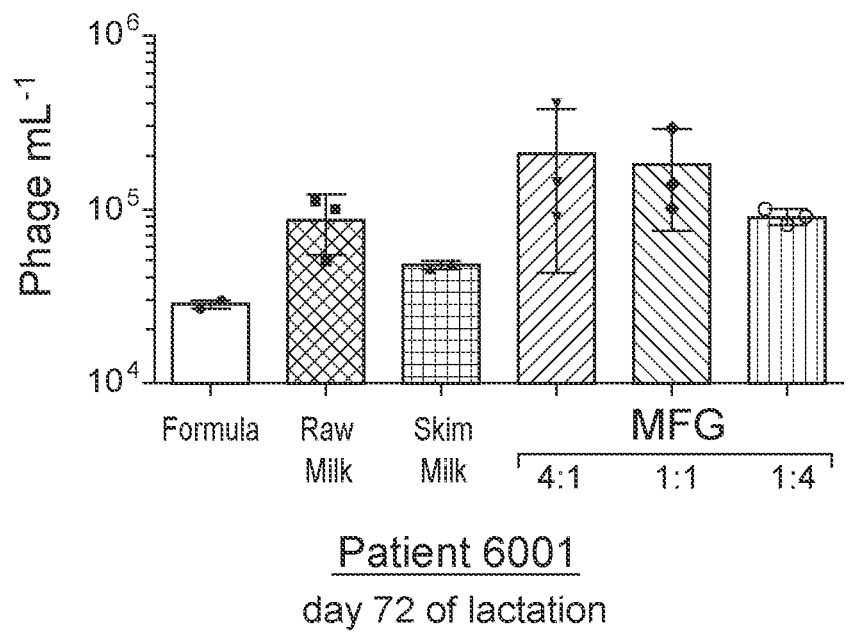
Figure 20B:
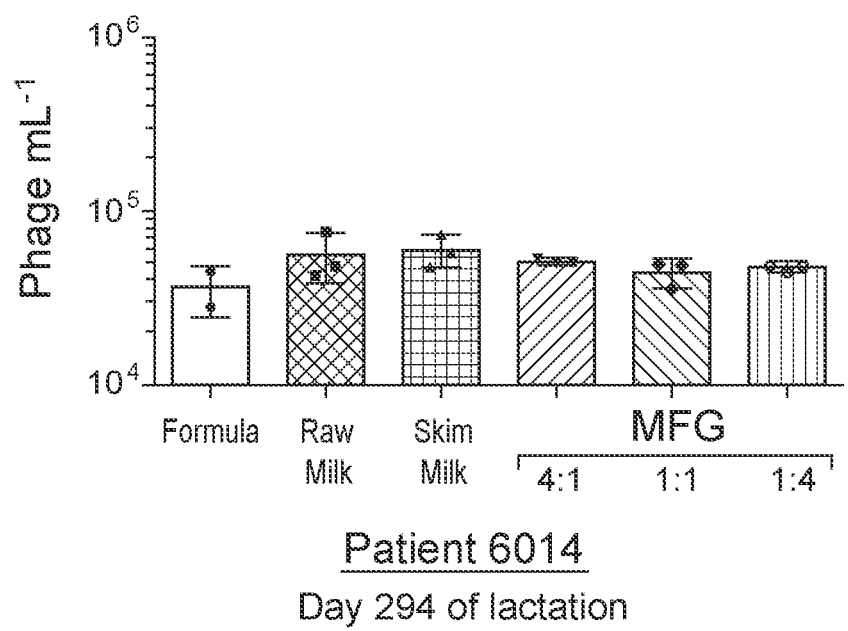

FIG. 20A and FIG. 20B graphically illustrates how the MFG as isolated in FIG. 19 affects the adherence of phage in two different human milk samples (FIG. 20A and FIG. 20B, see FIG. 15), where the data demonstrates that the MFG (mixed with raw milk) is better than (FIG. 20A) or is at least comparable to (FIG. 20B) raw and skim milk alone (no MFG), as compared to formula, in facilitating phage adherence to LS513 epithelial cells (where T4 phage at $10^7$/ml was mixed with either formula, raw breast milk, skim milk or varying ratios of isolated MFG and raw milk; the mix layered onto the LS513 epithelial cells for 30 min, 37° C., washed and adherent phage quantified by PFU.

Figure 21:
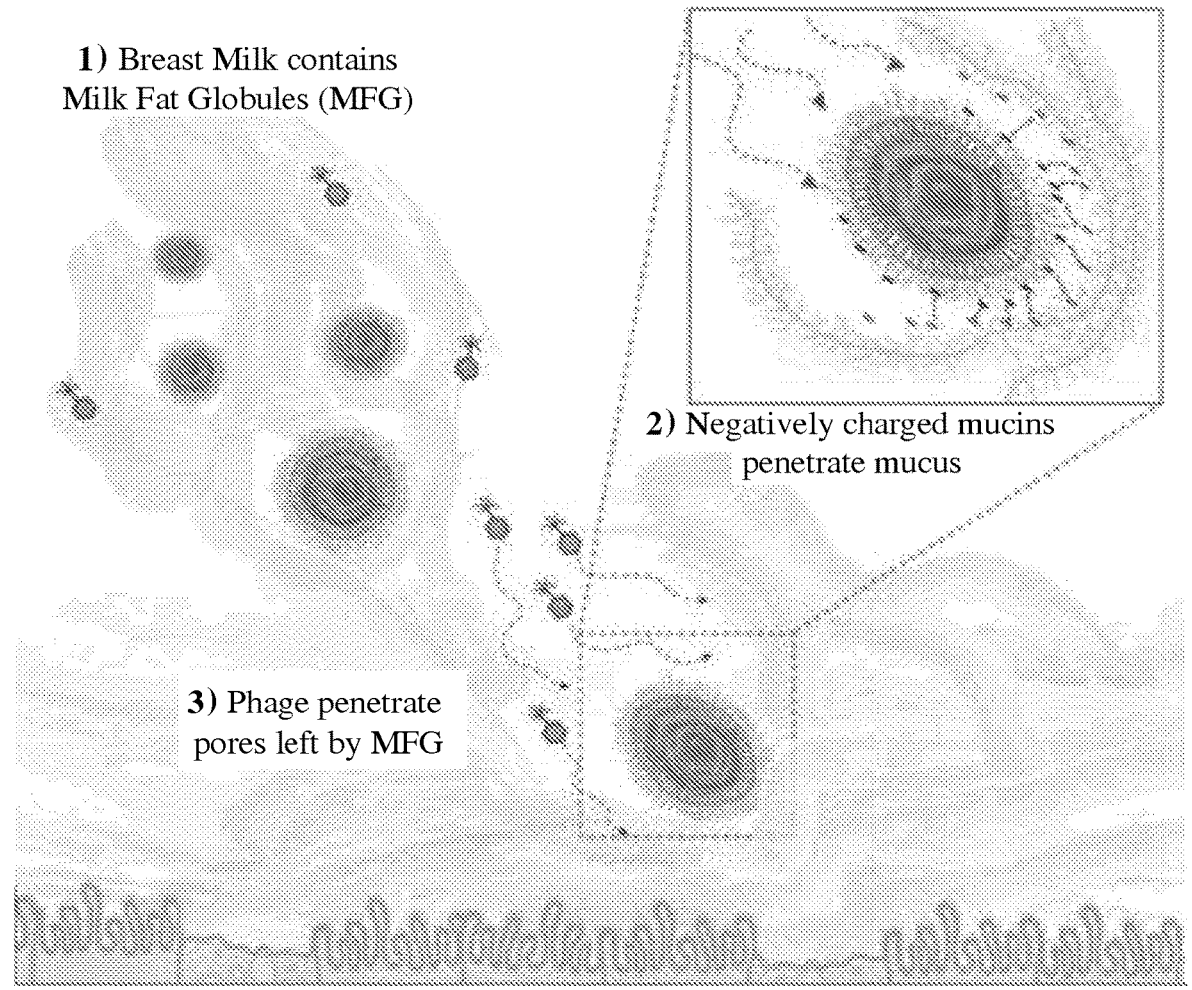

FIG. 21 illustrates an image, and describes, how the negatively charged mucins of breast milk MFGs facilitate the penetration of phage into an epithelial cell surface mucin layer.

Figure 22:
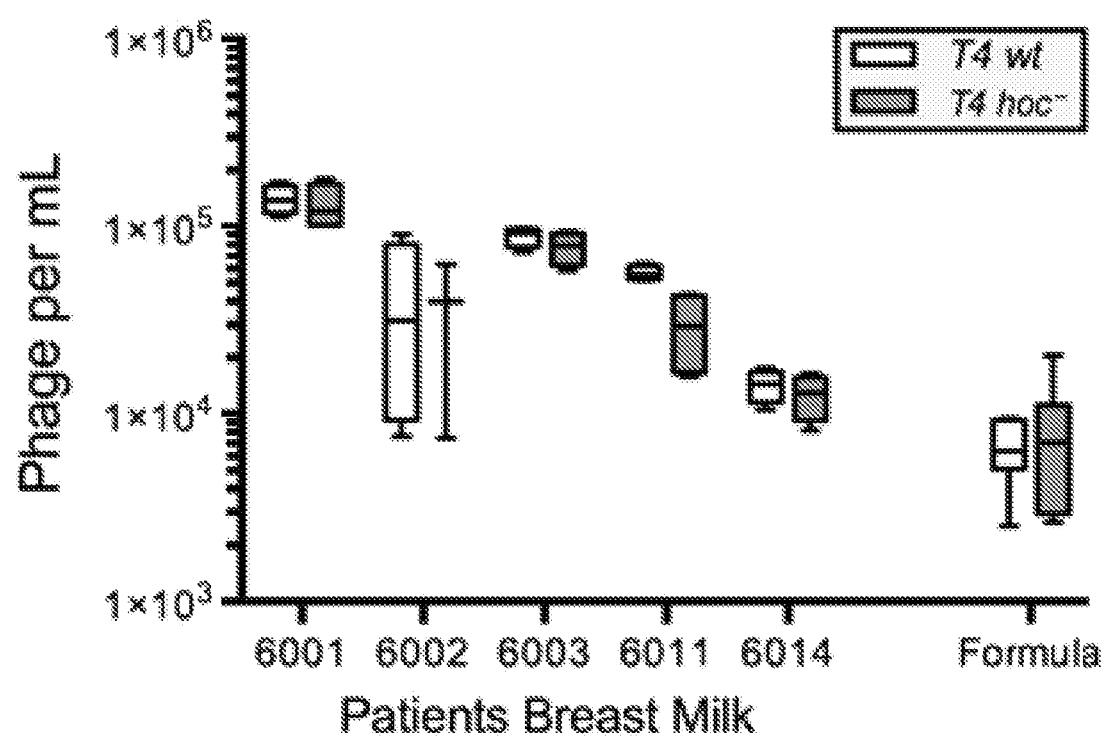

FIG. 22 graphically illustrates quantification of phage adherent to an epithelial cell surface in five different human breast milk samples (see FIG. 15) and formula, where either wild type (WT) or hoc$^-$ T4 phage at $10^7$/ml were mixed with breast milk for 30 min, 37° C., washed 3 times, the cells harvested and adherent phage quantified by PFU (as discussed below, Hoc structural proteins displayed on the T4 phage capsid interact with mucin, thereby slowing phage diffusion in mucus and increasing phage mucosal residence time).

FIG. 23A, FIG. 23B, FIG. 23C, FIG. 23D, FIG. 23E, FIG. 23F and FIG. 23G (or FIG. 1, of Example 2) schematically and graphically illustrates an exemplary microfluidic device (chip) designed to simulate a life-like in vitro mucosal surface, and their function, respectively. FIG. 23A) Schematic of chip design and measurements. FIG. 23B) Single chip bonded to a glass microscope slide with microfluidic tubing attached to in and out ports. FIG. 23C) Mucus-producing lung tissue cultured cells seeded into main channel. FIG. 23D) Cells in main after seven days of fluid flow and growth. E) Multiplex syringe pump running nine chips simultaneously. FIG. 23F) Phage therapy assay with phage and bacterial counts taken from the mucosal surface. FIG. 23G) Phage detachment rates from mucosal surface over a six hour period, dashed line indicates the 1 hr wash time point used in phage therapy assay; as further discussed in Example 2, below.

Figure 2A:
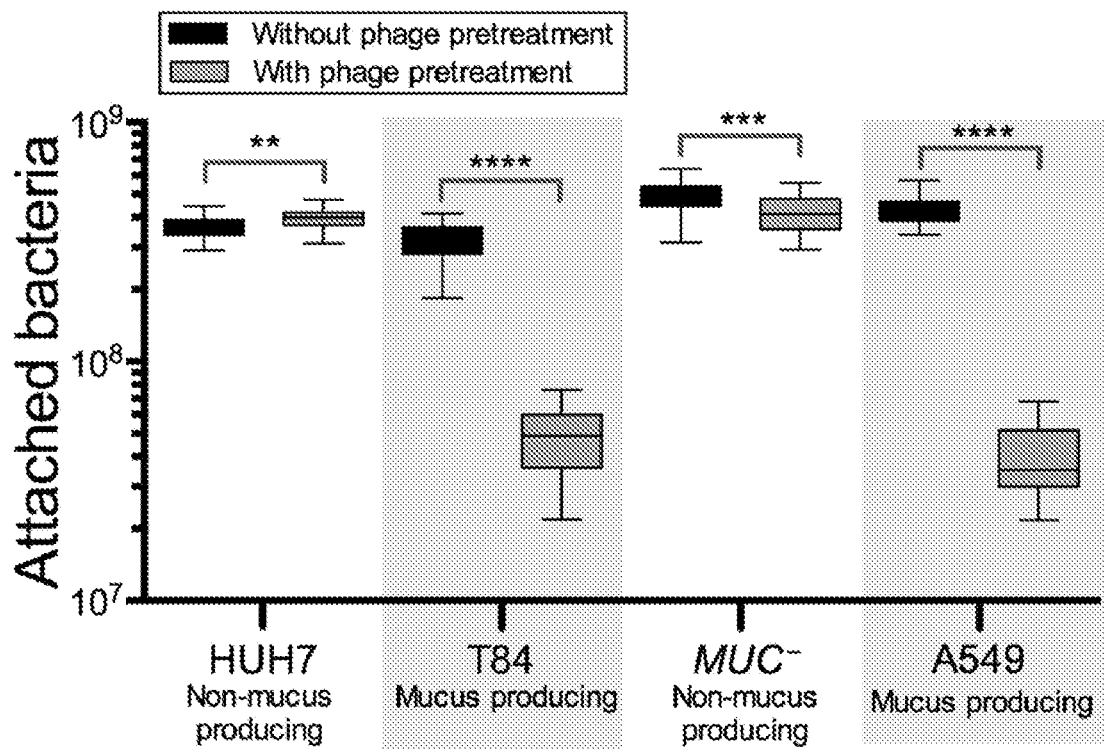
FIG. 2a and FIG. 2b graphically illustrate data showing the effect of phage adsorption on bacterial infection of epithelial cells.
Figure 24A:
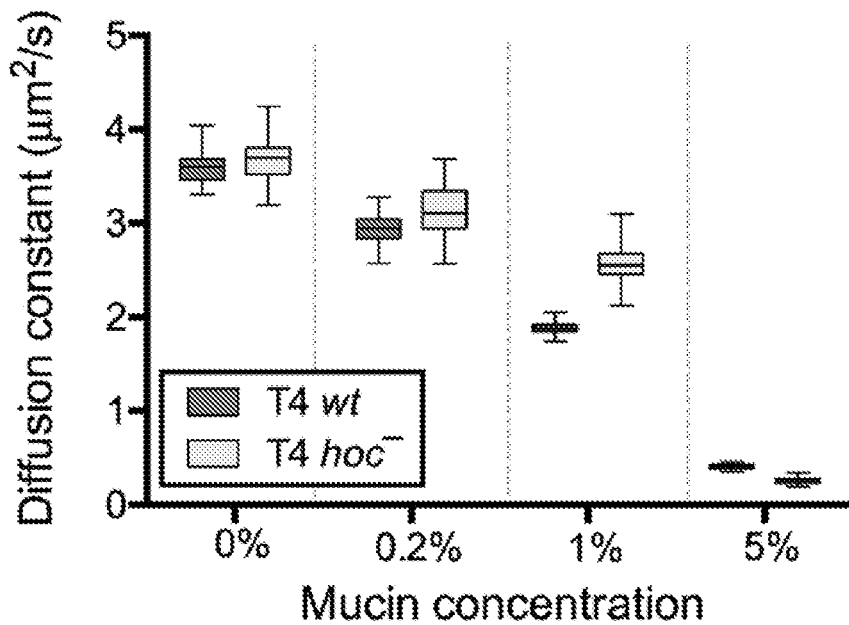
Figure 24B:
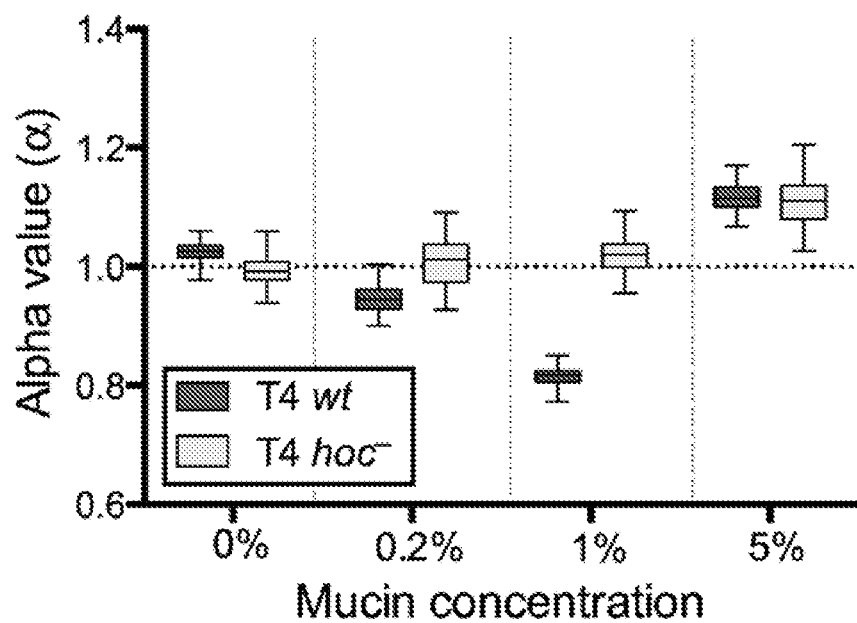

FIG. 24A and FIG. 24B (or FIG. 2, of Example 2) graphically illustrates: FIG. 24A) Mucus-adherent T4 wt and non-adherent T4 hoc$^-$ phage diffusion constants ($\mu m^2$/s) in 0% (buffer), 0.2%, 1%, and 5% mucin solutions (wt/vol). FIG. 24B) Alpha value ($\alpha$) measurements of T4 wt and T4 hoc⁻ phage in 0% (buffer), 0.2%, 1%, and 5% mucin solutions (wt/vol). Brownian diffusion $\alpha \approx 1$, subdiffusion $\alpha < 1$; as further discussed in Example 2, below.

Figure 25:
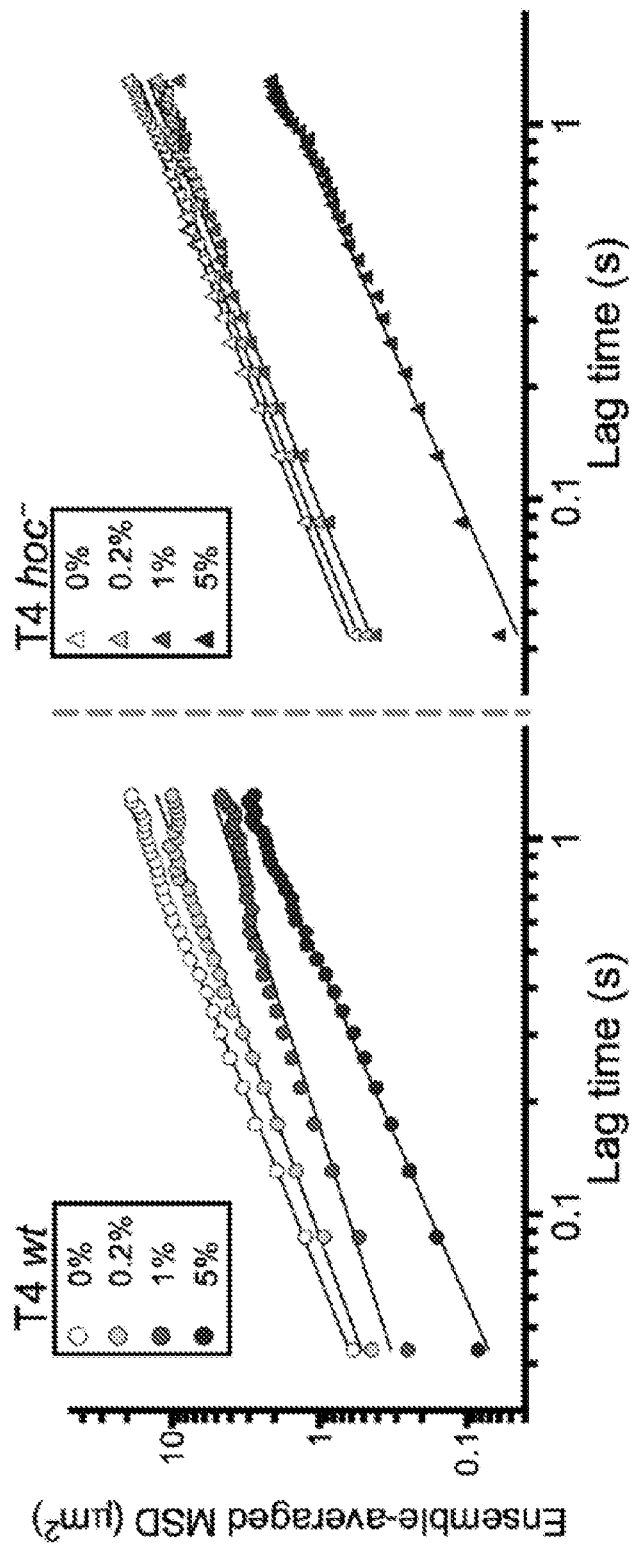

FIG. 25 (or FIG. 3, of Example 2) graphically illustrates: Ensemble-averaged mean square displacement (MSD) ($\mu m^2$) of mucus-adherent T4 wt and non-adherent T4 hoc⁻ phage in 0% (buffer), 0.2%, 1%, and 5% mucin solutions (wt/vol). Lines indicate best fit and alpha value ($\alpha$) are the measurement of slope; as further discussed in Example 2, below.

Figure 26A:
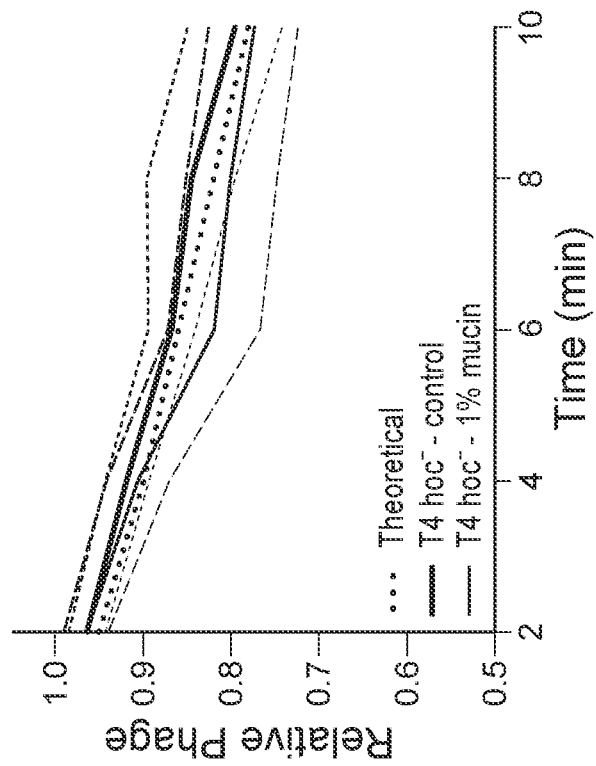
Figure 26B:
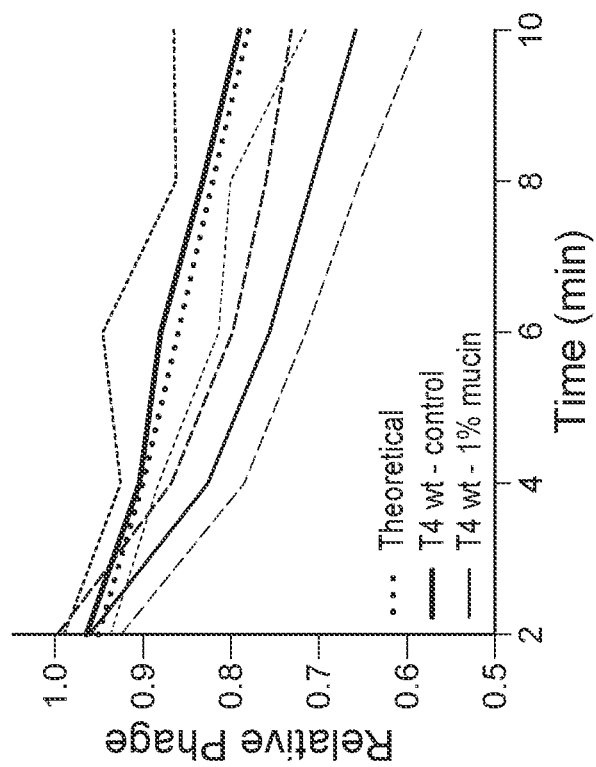

FIG. 26A and FIG. 26B (or FIG. 4, of Example 2) graphically illustrates: Adsorption of relative phage ($2 \times 10^5$ $mL^{-1}$) and *E. coli* host ($1 \times 10^7$ $mL^{-1}$) over a 10 min period, theoretical calculations used the T4 adsorption constant (k)=$2.4 \times 10^9$ $cm^3$/min. FIG. 26A) T4 wt phage adsorption in control (0%) and 1% mucin (wt/vol) solutions, with k=$2.3 \times 10^{-9}$ and $4.7 \times 10^{-9}$ $cm^3$/min, respectively. FIG. 26B) T4 hoc⁻ phage adsorption in control (0%) and 1% mucin (wt/vol) solutions, with k=$2.1 \times 10^{-9}$ and $2.6 \times 10^9$ $cm^3$/min, respectively; as further discussed in Example 2, below.

Figure 5:
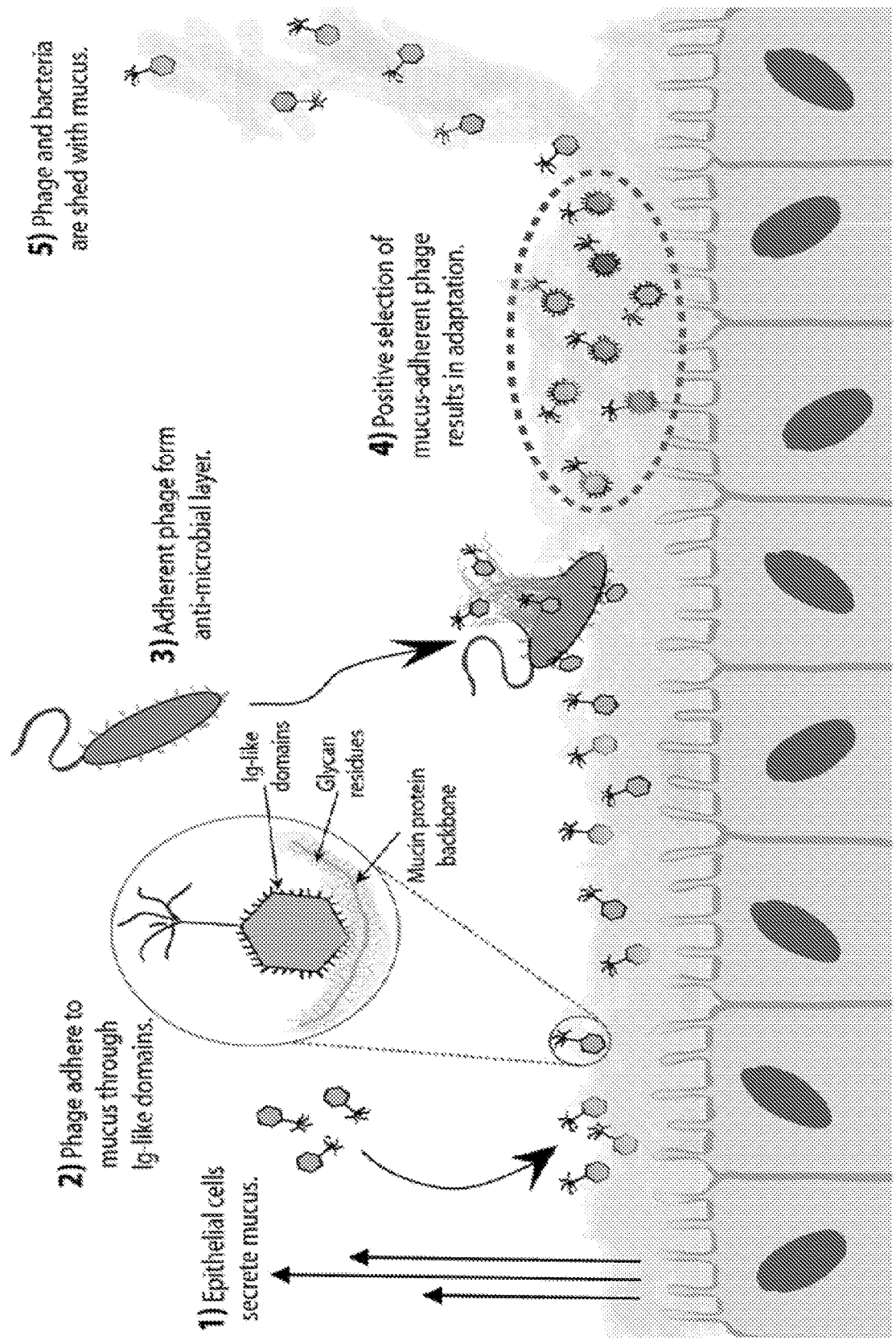
FIG. 5 schematically illustrates the so-called "Bacteriophage Adherence to Mucus (BAM) model": 1) Mucus is produced and secreted by the underlying epithelium. 2)
Figure 27:
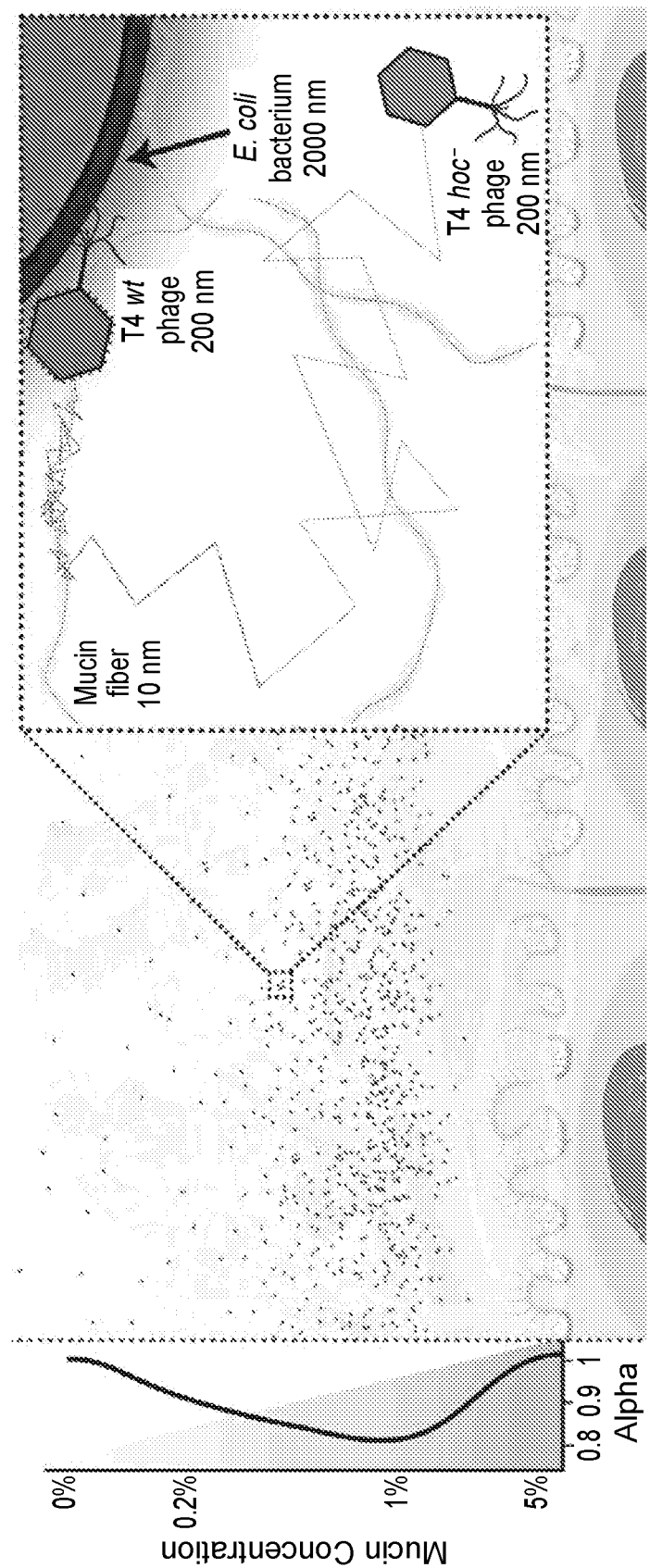

FIG. 27A and FIG. 27B (or FIGS. 5A and B, of Example 2) schematically and illustrates phage subdiffusion in a mucus network, and the phages' physical relationship to the exterior of a bacteria; as further discussed in Example 2, below.

FIG. 28A-B illustrates exemplary glycans that can be used to practice embodiments as provided herein; as further discussed in Example 2, below.

Like reference symbols in the various drawings indicate like elements.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, provided are compositions and methods for treating, ameliorating and preventing various infections, disorders and conditions in mammals, including genetically-predisposed and chronic disorders, where a microbial or bacterial flora is at least one causative or symptom-producing factor.

In alternative embodiment, provided herein are compositions and methods for treating, preventing or ameliorating conditions or infection caused by a microbe or a bacteria susceptible to lysis by a bacteriophage, or the bacteriophage has a microbiocidal, a bacteriocidal or bacteriostatic effect on the microbe or bacteria. In alternative embodiments, provided are products of manufacture, a food, a drink, a nutraceutical, a formulation, a pharmaceutical or a pharmaceutical preparation comprising a plurality of isolated, or substantially purified bacteriophages, or bacteriophage subunits, formulated with a milk, a milk product, milk lipid, milk fat globule (MFG) macromolecule, a milk mucin, a milk glycolipid, a milk free glycan, a milk mucin-like glycoprotein, a milk protein, a milk sugar or lactose, a milk fat or butterfat, a milk vitamin, or equivalents thereof, or a mixture thereof.

In alternative embodiment, provided herein are compositions and methods for treating, preventing or ameliorating an infection, for example, an infection in the gastrointestinal tract, or bowel, or any condition or disease caused or exacerbated by a microbe in the gastrointestinal tract, e.g., a bacterial infection. In alternative embodiment, compositions and methods as provided herein are used to target a microbe or a bacteria that is pathogenic, or is associated with or completely or partially causative of an infection or a condition, e.g., a colitis, obesity, diabetes, an autism and the like. In alternative embodiment, compositions and methods as provided herein are designed to target a particular microbe or bacteria by selecting a particular bacteriophage that has a microbiocidal, a bacteriocidal or bacteriostatic effect on the targeted microbe or bacteria. In alternative embodiments, compositions and methods as provided herein comprise use of a bacteriophage specific for, or a bacteriophage designed or constructed to be (e.g., by recombinant technology) specific for, or a bacteriophage subunit responsible for specifically targeting, a particular infectious agent or pathogen, a microbe or a bacteria that is pathogenic, or is associated with or completely or partially causative of an infection or a condition, for example, bacteria.

In alternative embodiments, provided are compositions, e.g., a drug delivery agent, a liposome or a micelle, a hydrogel, a dendrimer, a particle or a microparticle, a powder, a nanostructure or a nanoparticle, capable of targeting a specific microbe or bacteria, where in alternative embodiments the specific targeting is effected by incorporation of a component of a bacteriophage specific for, or a bacteriophage designed or constructed to be (e.g., by recombinant technology) specific for, or a bacteriophage subunit responsible for specifically targeting, the specific microbe or bacteria, which can be a particular infectious agent or pathogen, a microbe or a bacteria that is pathogenic, or is associated with or completely or partially causative of an infection or a condition, for example, bacteria.

Milk Products, Isolates, Components

In alternative embodiments, provided are compositions, and methods of using them, comprising (or comprising use of) a milk, a cream, or a milk product, component or isolate. In alternative embodiments, a milk, a cream, a milk product, milk component or milk isolate can comprise: a milk lipid, a milk fat globule (MFG) macromolecule, a mucin found in a milk (a milk mucin), a glycolipid found in a milk (a milk glycolipid), a free glycan found in a milk (a milk free glycan), a mucin-like glycoprotein found in a milk (a milk mucin-like glycoprotein), a milk protein (e.g., a casein, a casein micelle, or a whey, e.g., a beta-lactoglobulin or an alpha-lactalbumin), a milk sugar or a lactose, a milk fat or a butterfat. In alternative embodiments, a milk, a cream, a milk product, milk component or milk isolate can comprise: milk fat globule (MFG) macromolecule, mucin found in a milk (a milk mucin), glycolipid found in a milk (a milk glycolipid), free glycan found in a milk (a milk free glycan), mucin-like glycoprotein found in a milk (a milk mucin-like glycoprotein), milk protein, milk sugar or lactose, milk fat or butterfat, milk vitamin, or equivalents thereof, or a mixture thereof.

Any method known in the art can be used to generate, process or make, a milk, a cream, or a milk product, component or isolate used to practice embodiments as provided herein. For example, any known method or process used to process milk, e.g., breast milk, into its structural components or fractions, including full milk, skim milk, milk fat content ranging from 0.1% to 100%, cream, can be used, including methods and processes that do not use heat, excessive heat, pasteurization and/or shredding, shearing or fragmenting of milk components such as milk fat globules, milk fat globule (MFG) macromolecules, or milk fat membranes.

For example, methods as described in WO/2001/035760 A1 can be used for the bulk preparation of milk fat globule membranes. Alternatively, methods as described in US pat app publication nos. 2012 0321600 A1 or 2014 0105875 A1, can be used for to isolating and/or preparing milk fat globule (MFG) membranes and MFG components. Alternatively, methods and processes as described in US patents (USPN) or application publications can be used, for example: U.S. Pat. No. 5,861,491, which describes methods for isolating and preparing macromolecular species present in the milk, e.g., hydrophobic interaction chromatography; U.S. Pat. No. 6,444,247, which describes preparation of milk fat globule membranes in tablet or capsule form; U.S. Pat. No. 4,994,496, which describes use of milk fat globules as carriers for drugs; U.S. Pat. No. 4,997,668, which describes production of low-cholesterol milk fat by solvent extraction; U.S. Pat. No. 8,846,604, which describes making lipid compositions comprising phospholipids having a high docosahexaenoic acid (DHA) content; U.S. Pat. No. 8,012,509, which describes various milk fractions and milk preparations; US pat app pub no 20140255539 and 20140255537, which describe making structured fat globules from an enriched lipid fraction derived from milk; US pat app pub no 20140093554 and 20110300204 which describe making nutritional compositions for infants and/or toddlers comprising a lipid component which has a large lipid globule size; US pat app pub no 20100068293, describing making milk ingredients enriched in polar lipids such as phospholipids and in sphingolipids; US pat app pub nos 20140127350 and 20060150916 which describe separating components from milk. Additionally, methods described in WO/2001/035760 A1, teaching bulk preparation methods for isolating milk fat globule membranes from milk, can be used.

Probiotics, Postbiotics, Prebiotics, and Synbiotics

In alternative embodiments, additives that are also included in a composition as provided herein (e.g., a product of manufacture, food, drink, nutraceutical, formulation, pharmaceutical or pharmaceutical preparation), or a composition used to practice embodiments as provided herein, includes one or more prebiotics, postbiotics, probiotics or synbiotics, including for example: inulin, lactulose, extracts of artichoke, chicory root, oats, barley, various legumes, garlic, kale, beans or flacks and at times prebiotics may include herbs.

Also, in alternative embodiments, provided herein are uses and methods for: increasing or decreasing an effective dose of a probiotic, a prebiotic, a postbiotic or a synbiotic; increasing or decreasing efficacy of a probiotic, a prebiotic, a postbiotic or a synbiotic attaching to mucosal surfaces; increasing or decreasing access of a probiotic, a prebiotic, a postbiotic or a synbiotic to mucosal surfaces; or, increasing or decreasing resistance of a probiotic, a prebiotic, a postbiotic or a synbiotic to temperature, pH, mechanical stress, osmotic stress and/or gastrointestinal enzymes.

In alternative embodiments, additives may include beneficial (e.g., prebiotics, postbiotics, probiotics or synbiotics) flora components such as Bacteroidetes, Firmicutes, *Bacillus* (e.g., *Bacillus thurigiensis*) or any combination thereof. In alternative embodiments, cultured components are back to the flora to fortify or expand specific genus or species, e.g., Bacteroidetes, Firmicutes, *Bacillus* or *Bacillus thurigiensis*. In alternative embodiments, prebiotics comprises a nondigestible oligosaccharide, optionally an inulin, a fructan, a xylose, a maltose, a mannose, or a fructooligosaccharide. In alternative embodiments, probiotic bacteria comprise: a *Bacillus* or a *Lactobacillus*; or, a *Bacillus coagulans*, a *Lactobacillus acidophilus*, a *Lactobacillus plantarum* or a *Lactobacillus rhamnosus*. In alternative embodiments, probiotic comprise yeasts, e.g., comprise a *Saccharomyces*; or a *Saccharomyces boulardii*.

Probiotics, postbiotics, synbiotics etc. may at times be included as single cultured components. They would avoid multiply cultured components as they lose their implantation characteristics.

Preservatives, Cryoprotectants, Lyoprotectants

In alternative embodiments, to any composition as provided herein, for example, a particle, a nanoparticle, a liposome, a tablet, a pill, a capsule, a gel, a geltab, a liquid, a powder, a suspension, a syrup, an emulsion, a lotion, an ointment, an aerosol, a spray, a lozenge, an ophthalmic preparation, an aqueous or a sterile or an injectable solution, a patch (optionally a transdermal patch or a medicated adhesive patch), an implant, a dietary supplement, an ice cream, an ice, a yogurt, a cheese, an infant formula or infant dietary supplement, a pasteurized milk or milk product or milk-comprising product, or a liquid preparation embodiment or candies, lollies, drinks and the like, there can be added various preservatives, cryoprotectants and/or lyoprotectants, including e.g., various polysaccharides or sugars (such as sucrose, fructose, lactose, mannitol), glycerol, polyethylene glycol (PEG), trehalose, glycine, glucose, dextran and/or crythritol. In alternative embodiments, other cryoprotectants that can be used are ethylene glycol, 1,2-Propanediol, Methylcelliosolve, Dimethyl Formamide, or Dimethylsulphoxide Methanol. In alternative embodiments the content of these cryoprotectants are between about 1% and about 50% but generally between about 5% and about 15% is adequate.

In alternative embodiments, a composition o as provided herein is frozen and/or is freeze-dried, or spray dried, or lyophilized, using any method known in the art. For example, a method for freeze-drying bacteriophage can be used as described by Puapermpoonsiri et al., Int J. Pharm. 2010 Apr. 15; 389(1-2):168-75, who used sucrose or poly (ethylene glycol) 6000 to make bacteriophage-comprising freeze-dried cakes; or a method for making freeze-dried formulations of bacteriophage encapsulated in biodegradable microsphere, as described by Puapermpoonsiri et al., European J. Pharmaceutics and Biopharmaceutics, Vol. 72, Issue 1, 2009, Pgs 26-33; or methods for making stable bacteriophage compositions or matrices, as described e.g., by Murthy et al. WO2006047870 A1, or U.S. Pat. No. 8,309,077.

In alternative embodiments there are different types of final products that can be manufactured. In alternative embodiments a product or formulation as provided herein is a liquid. In alternative embodiments a product or formulation as provided herein is frozen and kept at e.g. minus 80 degrees for usage later given a cryoprotectant is added.

Biofilm Disrupting Compounds

In alternative embodiments, biofilm disrupting compounds added into a composition or formulation o as provided herein (e.g., a product of manufacture, food, drink, nutraceutical, formulation, pharmaceutical or pharmaceutical preparation), or used to practice a method as provided herein. In alternative embodiments, in practicing the methods as provided herein, biofilm disrupting compounds are administered before or during (co-administered), or co-formulated with (e.g., in a multilaminated tablet or capsule), or separately formulated, as the administered composition or formulation as provided herein. In alternative embodiments, disrupting biofilms are used to separate from the colonic mucosa an adherent polysaccharide/DNA-containing layer, the so-called "biofilm".

In alternative embodiments, other biofilm disrupting components or agents also can be used, e.g., enzymes such as a deoxyribonuclease (DNase), a N-acetylcysteine, an auranofin, alginate lyase, glycoside hydrolase dispersin B; Quorum-sensing inhibitors e.g., ribonucleic acid III inhibiting peptide, *Salvadora persica* extracts, Competence-stimulating peptide, Patulin and penicillic acid; peptides—cathelicidin-derived peptides, small lytic peptide, PTP-7 (a small lytic peptide, see e.g., Kharidia (2011) J. Microbiol. 49(4): 663-8, Epub 2011 Sep. 2), Nitric oxide, neo-emulsions; ozone, lytic bacteriophages, lactoferrin, xylitol hydrogel, synthetic iron chelators, cranberry components, curcumin, silver nanoparticles, Acetyl-11-keto-β-boswellic acid (AKBA), barley coffee components, probiotics, sinefungin, S-adenosylmethionine, S-adenosyl-homocysteine, Delisea furanones, N-sulfonyl homoserine lactones and/or macrolide antibiotics or any combination thereof.

In alternative embodiments, biofilm disrupting components or agents are administered before and during the administration of a composition as provided herein, e.g., as an antibacterial, in whatever format or formulation this may take place, for example, as a capsule.

In alternative embodiments, biofilm disrupting agents are added either before treatment and/or during and/or after treatment with a composition as provided herein. In alternative embodiments, biofilm disrupting agents are used singly or in combination.

In alternative embodiments, biofilm disrupting agents include particular enzymes and degrading substances including in N-acetylcysteine, deoxyribonuclease (DNase). Others would include Alginate, lyase and Glycoside hydrolase dispersin, Ribonucleic-acid-Ill inhibiting peptide (RIP), *Salvadora persica* extracts, Competence-stimulating peptide (CSP) Patulin (PAT) and penicillic acid (PA)/EDTA, Cathelicidin-derived peptides, Small lytic peptide, PTP-7, Nitric oxide, Chlorhexidine, Povidone-iodine (PI), Nanoemulsions, Lytic bacteriophages, Lactoferrin/xylitol hydrogel, Synthetic iron chelators, Cranberry components, Curcumin, Acetyl-11-keto-boswellic acid (AKBA), Barley coffee (BC) components, silver nanoparticles, azithromycin, clarithromycin, gentamicin, streptomycin and also Disodium EDTA. Ozone insufflations of the colon can also be used to disrupt the biofilm.

Unit Dosage Forms and Formulations, Foods, and Delivery Vehicles

In alternative embodiments, a composition as provided herein (e.g., a particle, a nanoparticle, a liposome, a tablet, a pill, a capsule, a gel, a geltab, a liquid, a powder, a suspension, a syrup, an emulsion, a lotion, an ointment, an aerosol, a spray, a lozenge, an ophthalmic preparation, an aqueous or a sterile or an injectable solution, a patch (optionally a transdermal patch or a medicated adhesive patch), an implant, a dietary supplement, an ice cream, an ice, a yogurt, a cheese, an infant formula or infant dietary supplement, a pasteurized milk or milk product or milk-comprising product) can be further processed by, e.g., spray-drying or equivalent, e.g., spray-drying in an inert gas or freeze-drying under similar conditions, thus ending up with a powdered product.

In alternative embodiments, a composition o as provided herein can be formulated for enteral or parenteral administration, e.g., to reach the systemic circulation, or for local delivery (e.g., for administration to skin, ears, teeth), as a topical for e.g., infections, as an inhalant, e.g., for inhalation of phages for the treatment of e.g., lung infections, as described e.g., by Ryan et al. J Pharm Pharmacol. 2011 October; 63(10):1253-64.

In alternative embodiments, a composition is manufactured, labelled or formulated as a liquid, a suspension, a spray, a gel, a geltab, a semisolid, a tablet, or sachet, a capsule, a lozenge, a chewable or suckable unit dosage form, or any pharmaceutically acceptable formulation or preparation. In alternative embodiments, a composition as provided herein is incorporated into a food or a drink (e.g., a yogurt, ice cream, smoothie), a candy, sweet or lolly, or a feed, a nutritional or a food or feed supplement (e.g., liquid, semisolid or solid), and the like.

For example, bacteriophage used to practice embodiments as provided herein can be encapsulated as described, e.g., by Murthy et al. in US 2012-0258175 A1. A composition as provided herein can be manufactured, labelled or formulated as an orally disintegrating tablet as described e.g., in U.S. Pat. App. Publication No. 20100297031. A composition as provided herein can be a polyol/thickened oil suspension as described in U.S. Pat. No. (USPN) 6,979,674; 6,245,740. A composition as provided herein can be encapsulated, e.g., encapsulated in a glassy matrix as described e.g., in U.S. Pat. App. Publication No. 20100289164; and U.S. Pat. No. 7,799,341. A composition as provided herein can be manufactured, labelled or formulated as an excipient particle, e.g., comprising a cellulosic material such as microcrystalline cellulose in intimate association with silicon dioxide, a disintegrant and a polyol, sugar or a polyol/sugar blend as described e.g., in U.S. Pat. App. Publication No. 20100285164. A composition as provided herein can be manufactured, labelled or formulated as an orally disintegrating tablet as described e.g., in U.S. Pat. App. Publication No. 20100278930. A composition as provided herein can be manufactured, labelled or formulated as a spherical particle, as described e.g., in U.S. Pat. App. Publication No. 20100247665, e.g., comprising a crystalline cellulose and/or powdered cellulose. A composition as provided herein can be manufactured, labelled or formulated as a rapidly disintegrating solid preparation useful e.g. as an orally-disintegrating solid preparation, as described e.g., in U.S. Pat. App. Publication No. 20100233278. A composition as provided herein can be manufactured, labelled or formulated as a solid preparation for oral application comprising a gum tragacanth and a polyphosphoric acid or salt thereof, as described e.g., in U.S. Pat. App. Publication No. 20100226866.

A composition as provided herein can be manufactured, labelled or formulated using a water soluble polyhydroxy compound, hydroxy carboxylic acid and/or polyhydroxy carboxylic acid, as described e.g., in U.S. Pat. App. Publication No. 20100222311. A composition as provided herein can be manufactured, labelled or formulated as a lozenge, or a chewable and suckable tablet or other unit dosage form, as described e.g., in U.S. Pat. App. Publication No. 20100184785.

A composition as provided herein can be manufactured, labelled or formulated in the form of an agglomerate, as described e.g., in U.S. Pat. App. Publication No. 20100178349. A composition as provided herein can be manufactured, labelled or formulated in the form of a gel or paste, as described e.g., in U.S. Pat. App. Publication No. 20060275223. A composition as provided herein can be manufactured, labelled or formulated in the form of a soft capsule, as described e.g., in U.S. Pat. No. 7,846,475, or U.S. Pat. No. 7,763,276.

The polyols used in compositions as provided herein can be micronized polyols, e.g., micronized polyols, e.g., as described e.g., in U.S. Pat. App. Publication No.

20100255307, e.g., having a particle size distribution ($d_{50}$) of from 20 to 60 μm, and a flowability below or equal to 5 s/100 g, or below 5 s/100 g.

In practicing embodiments as provided herein, a wide variation of bacteriophage can be administered, for example, in some aspects, a smaller dosage can be administered because phage (i.e., bacteriophage) can replication in the host, i.e., in the individual to which a composition as provided herein is administered. In alternative embodiments, compositions as provided herein, including phage as provided herein, are formulated per dose, or per serving, or per unit dosage at, or at a total daily dose of: between about 10(1) (or $10^1$) and 10(20) plaque-forming units (PFUs), or between about 10(3) and 10(17) PFUs, or between about 10(5) and 10(12) PFUs, or between about 10(7) and 10(9) PFUs.

Gradual or Delayed Release Formulations

In alternative embodiments, provided are compositions formulated for delayed or gradual enteric release comprising at least one active agent (e.g., a composition, a formulation or a pharmaceutical preparation as provided herein) formulated with a delayed release composition or formulation, coating or encapsulation. In alternative embodiments, formulations or pharmaceutical preparations as provided herein are designed or formulated for delivery of active ingredient (e.g., a bacteriophage) into the distal small bowel and/or the colon. Thus, for this embodiment, it is important to allow the active ingredient to pass the areas of danger, e.g., stomach acid and pancreatic enzymes and bile, and reach undamaged to be viable in the distal small bowel and especially the colon. In alternative embodiments, a formulation or pharmaceutical preparation as provided herein is a liquid formulation, a microbiota-comprising formulation as provided herein and/or a frozen or a freeze-dried version thereof. In alternative embodiments, preferably for the encapsulated format, all are in powdered form.

In alternative embodiments, compositions as provided herein are formulated for delayed or gradual enteric release using cellulose acetate (CA) and polyethylene glycol (PEG), e.g., as described by Defang et al. (2005) Drug Develop. & Indust. Pharm. 31:677-685, who used CA and PEG with sodium carbonate in a wet granulation production process.

In alternative embodiments, compositions as provided herein are formulated for delayed or gradual enteric release using a hydroxypropylmethylcellulose (HPMC), a microcrystalline cellulose (MCC) and magnesium stearate, as described e.g., in Huang et al. (2004) European J. of Pharm. & Biopharm. 58: 607-614).

In alternative embodiments, compositions as provided herein are formulated for delayed or gradual enteric release using e.g., a poly(meth)acrylate, e.g. a methacrylic acid copolymer B, a methyl methacrylate and/or a methacrylic acid ester, a polyvinylpyrrolidone (PVP) or a PVP-K90 and a EUDRAGIT® RL PO™, as described e.g., in Kuksal et al. (2006) AAPS Pharm. 7(1), article 1, E1 to E9.

In alternative embodiments, compositions as provided herein are formulated for delayed or gradual enteric release as described in U.S. Pat. App. Pub. 20100239667. In alternative embodiments, the composition comprises a solid inner layer sandwiched between two outer layers. The solid inner layer can comprise a formulation or pharmaceutical preparation as provided herein and one or more disintegrants and/or exploding agents, one of more effervescent agents or a mixture. Each outer layer can comprise a substantially water soluble and/or crystalline polymer or a mixture of substantially water soluble and/or crystalline polymers, e.g., a polyglycol. These can be adjusted in an exemplary composition as provided herein to achieve delivery of the living components of an FMT distally down the bowel.

In alternative embodiments, compositions as provided herein are formulated for delayed or gradual enteric release as described in U.S. Pat. App. Pub. 20120183612, which describes stable pharmaceutical formulations comprising active agents in a non-swellable diffusion matrix. In alternative embodiments, a formulation or pharmaceutical preparation as provided herein is released from a matrix in a sustained, invariant and, if several active agents are present, independent manner and the matrix is determined with respect to its substantial release characteristics by ethylcellulose and at least one fatty alcohol to deliver bacteria distally.

In alternative embodiments, a formulation or pharmaceutical preparation as provided herein is formulated for delayed or gradual enteric release as described in U.S. Pat. No. 6,284,274, which describes a bilayer tablet containing an active agent (e.g., an opiate analgesic), a polyalkylene oxide, a polyvinylpyrrolidone and a lubricant in the first layer and a second osmotic push layer containing polyethylene oxide or carboxy-methylcellulose.

In alternative embodiments, a formulation or pharmaceutical preparation as provided herein is formulated for delayed or gradual enteric release as described in U.S. Pat. App. Pub. No. 20030092724, which describes sustained release dosage forms in which a nonopioid analgesic and opioid analgesic are combined in a sustained release layer and in an immediate release layer, sustained release formulations comprising microcrystalline cellulose, EUDRAGIT RSPO™, CAB-O-SIL™, sodium lauryl sulfate, povidone and magnesium stearate.

In alternative embodiments, a formulation or pharmaceutical preparation as provided herein is formulated for delayed or gradual enteric release as described in U.S. Pat. App. Pub. 20080299197, describing a multi-layered tablet for a triple combination release of active agents to an environment of use, e.g., in the GI tract. In alternative embodiments, a multi-layered tablet is used, and it can comprise two external drug-containing layers in stacked arrangement with respect to and on opposite sides of an oral dosage form that provides a triple combination release of at least one active agent. In one embodiment the dosage form is an osmotic device, or a gastro-resistant coated core, or a matrix tablet, or a hard capsule. In these alternative embodiments, the external layers may contain biofilm dissolving agents and internal layers the living bacteria.

In alternative embodiments, a formulation or pharmaceutical preparation as provided herein is formulated as multiple layer tablet forms, e.g., where a first layer provides an immediate release of a formulation or pharmaceutical preparation as provided herein and a second layer provides a controlled-release of another (or the same) formulation or pharmaceutical preparation as provided herein, or another active agent, as described e.g., in U.S. Pat. No. 6,514,531 (disclosing a coated trilayer immediate/prolonged release tablet), U.S. Pat. No. 6,087,386 (disclosing a trilayer tablet), U.S. Pat. No. 5,213,807 (disclosing an oral trilayer tablet with a core comprising an active agent and an intermediate coating comprising a substantially impervious/impermeable material to the passage of the first active agent), and U.S. Pat. No. 6,926,907 (disclosing a trilayer tablet that separates a first active agent contained in a film coat from a core comprising a controlled-release second active agent formulated using excipients which control the drug release, the film coat can be an enteric coating configured to delay the release of the active agent until the dosage form reaches an environment where the pH is above four).

In alternative embodiments, a formulation or pharmaceutical preparation as provided herein is formulated for delayed or gradual enteric release as described in U.S. Pat. App. Pub. 20120064133, which describes a release-retarding matrix material such as: an acrylic polymer, a cellulose, a wax, a fatty acid, shellac, zein, hydrogenated vegetable oil, hydrogenated castor oil, polyvinylpyrrolidine, a vinyl acetate copolymer, a vinyl alcohol copolymer, polyethylene oxide, an acrylic acid and methacrylic acid copolymer, a methyl methacrylate copolymer, an ethoxyethyl methacrylate polymer, a cyanoethyl methacrylate polymer, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate polymer, a polymethacrylate, a poly(methyl methacrylate) copolymer, a polyacrylamide, an aminoalkyl methacrylate copolymer, a glycidyl methacrylate copolymer, a methyl cellulose, an ethylcellulose, a carboxymethylcellulose, a hydroxypropylmethylcellulose, a hydroxymethyl cellulose, a hydroxyethyl cellulose, a hydroxypropyl cellulose, a crosslinked sodium carboxymethylcellulose, a crosslinked hydroxypropylcellulose, a natural wax, a synthetic wax, a fatty alcohol, a fatty acid, a fatty acid ester, a fatty acid glyceride, a hydrogenated fat, a hydrocarbon wax, stearic acid, stearyl alcohol, beeswax, glycowax, castor wax, carnauba wax, a polylactic acid, polyglycolic acid, a co-polymer of lactic and glycolic acid, carboxymethyl starch, potassium methacrylate/divinylbenzene copolymer, crosslinked polyvinylpyrrolidone, polyvinylalcohols, polyvinylalcohol copolymers, polyethylene glycols, non-crosslinked polyvinylpyrrolidone, polyvinylacetates, polyvinylacetate copolymers or any combination. In alternative embodiments, spherical pellets are prepared using an extrusion/spheronization technique, of which many are well known in the pharmaceutical art. The pellets can comprise one or more formulations or pharmaceutical preparations as provided herein, e.g., the liquid preparation embodiment.

In alternative embodiments, a formulation or pharmaceutical preparation as provided herein is formulated for delayed or gradual enteric release as described in U.S. Pat. App. Pub. 20110218216, which describes an extended release pharmaceutical composition for oral administration, and uses a hydrophilic polymer, a hydrophobic material and a hydrophobic polymer or a mixture thereof, with a microenvironment pH modifier. The hydrophobic polymer can be ethylcellulose, cellulose acetate, cellulose propionate, cellulose butyrate, methacrylic acid-acrylic acid copolymers or a mixture thereof. The hydrophilic polymer can be polyvinylpyrrolidone, hydroxypropylcellulose, methylcellulose, hydroxypropylmethyl cellulose, polyethylene oxide, acrylic acid copolymers or a mixture thereof. The hydrophobic material can be a hydrogenated vegetable oil, hydrogenated castor oil, carnauba wax, candellia wax, beeswax, paraffin wax, stearic acid, glyceryl behenate, cetyl alcohol, cetostearyl alcohol or and a mixture thereof. The microenvironment pH modifier can be an inorganic acid, an amino acid, an organic acid or a mixture thereof. Alternatively, the microenvironment pH modifier can be lauric acid, myristic acid, acetic acid, benzoic acid, palmitic acid, stearic acid, oxalic acid, malonic acid, succinic acid, adipic acid, sebacic acid, fumaric acid, maleic acid; glycolic acid, lactic acid, malic acid, tartaric acid, citric acid, sodium dihydrogen citrate, gluconic acid, a salicylic acid, tosylic acid, mesylic acid or malic acid or a mixture thereof.

In alternative embodiments, a formulation or pharmaceutical preparation as provided herein is a powder that can be included into a tablet or a suppository. In alternative embodiments, a formulation or pharmaceutical preparation as provided herein can be a 'powder for reconstitution' as a liquid to be drunk or otherwise administered. In alternative embodiments, a formulation or pharmaceutical preparation as provided herein is micro-encapsulated, formed into tablets and/or placed into capsules, especially enteric-coated capsules.

Buffers and Antacids

In alternative embodiments, in practicing the methods as provided herein, buffers or antacids are administered before or during (co-administered), or co-formulated with a composition or formulation as provided herein. For example, in alternative embodiments, a composition or formulation as provided herein and a buffer or antacid are co-formulated, e.g., as multiple layer tablet form or as a multi-laminated tablet or capsule. In alternative embodiments of methods as provided herein, buffers or antacids are separately formulated. In alternative embodiments, the antacid, buffer or buffering agent is administered (optionally before, during or after, or before and during, administration) to raise the pH of the stomach in the individual to between about 2.5 and 7, or between about 3 and 6.5, or to about 5.0, 5.5, 6.0, 6.5, 6.8 or 7.0 (optionally these pH values reached before, during or after, or before and during, administration). In alternative embodiments, the buffer or a buffering agent or the pharmaceutically acceptable excipient comprises an inorganic salt, a citric acid, a sodium chloride, a potassium chloride, a sodium sulfate, a potassium nitrate, a sodium phosphate monobasic, a sodium phosphate dibasic or combinations thereof. In alternative embodiments, the antacid comprises a calcium carbonate, a magnesium hydroxide, a magnesium oxide, a magnesium carbonate, an aluminum hydroxide, a sodium bicarbonate or a dihydroxyaluminum sodium carbonate.

Infant Formulas, Feeds, Drinks, Candies, Nutritional or a Food or Feed Supplements In alternative embodiments, a formulation or pharmaceutical preparation as provided herein is incorporated into an infant formula or equivalent infant food or supplement, a food, a feed, a candy (e.g., a lollypop or a lozenge) a drink, a nutritional or a food or feed supplement (e.g., liquid, semisolid or solid), and the like, as described e.g., in U.S. Pat. App. Publication No. 20100178413. In one embodiment, a formulation or pharmaceutical preparation as provided herein is incorporated into (manufactured as) a beverage as described e.g., in U.S. Pat. No. 7,815,956. For example, a composition as provided herein is incorporated into a yogurt, an ice cream, a milk or milkshake, a "frosty", "snow-cone", or other ice-based mix, and the like.

In alternative embodiments, a formulation or pharmaceutical preparation as provided herein is a freeze-dried powder form added to a food, e.g., a yogurt, an ice cream, a milk or milkshake, a "frosty", "snow-cone", or other ice-based mix, and the like. In one form of embodiments as provided herein it can be kept in a lid-storage (e.g., of a yogurt or ice cream) such that when it is twisted the powder falls into the product or formulation (e.g., yoghurt or ice cream) and then it can be stirred so as not to have the powder ferment 'standing on the shelf'. Various flavourings can be added. In alternative embodiments, this is particularly important for administration of a composition as provided herein, e.g., a wild type microbiota or a cultured bacteria, to a very young individual and/or a patient with autism or related disease or condition.

In alternative embodiments, these exemplary products are important when administered to children or babies who may have acquired various pathogenic or abnormal bacteria, e.g., *E. coli*, Clostridia or Disulfovibrio, e.g., as in autism.

Packaging

In alternative embodiments, provided are compositions (e.g., a product of manufacture, food, drink, nutraceutical, formulation, pharmaceutical or pharmaceutical preparation), including preparations, formulations and/or kits, comprise combinations of ingredients, as described herein. In alternative embodiments, these combinations can be mixed and administered together, or alternatively, they can be an individual member of a packaged combination of ingredients, e.g., as manufactured in a separate package, kit or container; or, where all or a subset of the combinations of ingredients are manufactured in a separate package or container. In alternative aspects, the package, kit or container comprises a blister package, a clamshell, a tray, a shrink wrap and the like.

In one aspect, the package, kit or container comprises a "blister package" (also called a blister pack, or bubble pack). In one aspect, the blister package is made up of two separate elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, provided are blister packs, clamshells or trays comprising a composition (e.g., a (the multi-ingredient combination of drugs as provided herein) combination of active ingredients) as provided herein. Blister packs, clamshells or trays can be designed to be non-reclosable, so consumers can tell if a package has already opened. They are used to package for sale goods where product tampering is a consideration, such as the pharmaceuticals as provided herein. In one aspect, a blister pack as provided herein comprises a moulded PVC base, with raised areas (the "blisters") to contain the tablets, pills, etc. comprising the combinations as provided herein, covered by a foil laminate. Tablets, pills, etc. are removed from the pack either by peeling the foil back or by pushing the blister to force the tablet to break the foil. In one aspect, a specialized form of a blister pack is a strip pack. In one aspect, in the United Kingdom, blister packs adhere to British Standard 8404.

In one embodiment, provided is a method of packaging where the compositions comprising combinations of ingredients as provided herein are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. as provided herein are used, and they can comprise of two vacuum-formed PVC sheets meshed together at the edges, with the informative card inside. These can be hard to open by hand, so a pair of scissors or a sharp knife may be required to open.

In one aspect, blister packaging comprises at least two or three or more components (e.g., is a multi-ingredient combination o as provided herein: a thermoformed "blister" which houses multi-ingredient combination as provided herein, and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or as large as you would like, but there are limitations and cost considerations in going to an oversized blister card. Conventional blister packs can also be sealed (e.g., using an AERGO 8 DUO™, SCA Consumer Packaging, Inc., DeKalb IL) using regular heat seal tooling. This alternative aspect, using heat seal tooling, can seal common types of thermoformed packaging.

Blister Packaging

In alternative embodiments, combinations of ingredients of compositions as provided herein, or combinations of ingredients for practicing methods as provided herein, can be packaged alone or in combinations, e.g., as "blister packages" or as a plurality of packettes, including as lidded blister packages, lidded blister or blister card or packets or packettes, or a shrink wrap.

In alternative embodiments, laminated aluminium foil blister packs are used, e.g., for the preparation of drugs designed to dissolve immediately in the mouth of a patient. This exemplary process comprises having the drug combinations as provided herein prepared as an aqueous solution(s) which are dispensed (e.g., by measured dose) into an aluminium (e.g., alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a child-proof peel open security laminate. In one aspect, the system give tablets an identification mark by embossing a design into the alufoil pocket that is taken up by the tablets when they change from aqueous to solid state. In one aspect, individual 'push-through' blister packs/packettes are used, e.g., using hard temper aluminium (e.g., alufoil) lidding material. In one aspect, hermetically-sealed high barrier aluminium (e.g., alufoil) laminates are used. In one aspect, any products of manufacture as provided herein, including kits or blister packs, use foil laminations and strip packs, stick packs, sachets and pouches, peelable and non-peelable laminations combining foil, paper, and film for high barrier packaging.

In alternative embodiments, any multi-ingredient combinations or products of manufacture as provided herein, including kits or blister packs, include memory aids to help remind patients when and how to take the drug. This safeguards the drug's efficacy by protecting each tablet, geltab or pill until it's taken; gives the product or kit portability, makes it easy to take a dose anytime or anywhere.

The invention will be further described with reference to the following examples; however, it is to be understood that the invention is not limited to such examples.

EXAMPLES

Example 1: Exemplary Treatments

This example provides data demonstrating the efficacy of embodiments as provided herein, and, while the invention is not limited by any particular mechanism of action, this example provides exemplary mechanisms by which exemplary embodiments provided antibacterial protection to an individual in need thereof.

Here we show that phage-to-bacteria ratios were increased, relative to the adjacent environment, on all mucosal surfaces sampled ranging from cnidarians to humans. In vitro studies of tissue culture cells with and without surface mucus demonstrated that this mucus-dependent increase in phage abundance protects the underlying epithelium from bacterial infection. Enrichment of phage in mucus occurs via interactions between mucin glycoproteins and immunoglobulin-like protein domains exposed on phage capsids. This interaction was found to be a result of phage immunoglobulin-like domains binding variable glycan residues that coat the mucin glycoprotein component of mucus. Metagenomic analysis found these immunoglobulin-like proteins present in many environments, particularly those adjacent to mucosal surfaces. Based on these observations, we present the Bacteriophage Adherence to Mucus (BAM) model, providing a ubiquitous but non-host-derived immune system applicable to mucosal surfaces. This model suggests that metazoan mucosal surfaces and phage have coevolved so that phage stick to them, thus benefiting the metazoan host through increased killing of mucosal bacteria, and the phage through increased interactions with bacterial hosts. The relationships shown here suggest a symbiotic relationship between phage and metazoan hosts, and the data herein demonstrate a novel immunity for mucosal surfaces.

Here we demonstrate that phage adhere to mucus and that this association reduces microbial colonization and pathology. In vitro studies demonstrated that this adherence was mediated by the interaction between displayed Ig-like domains of phage capsid proteins and glycan residues, such as those in mucin glycoproteins. Homologs of these Ig-like domains are encoded by phages from many environments, particularly those adjacent to mucosal surfaces. In alternative embodiments, provided are compositions and methods that can incorporate the so-called "Bacteriophage Adherence to Mucus (BAM)" model, and comprise use of phages to provide a non-host-derived antimicrobial defence on the mucosal surfaces of diverse metazoan hosts.

Results

Phage Adhere to Mucus

Figure 1A:
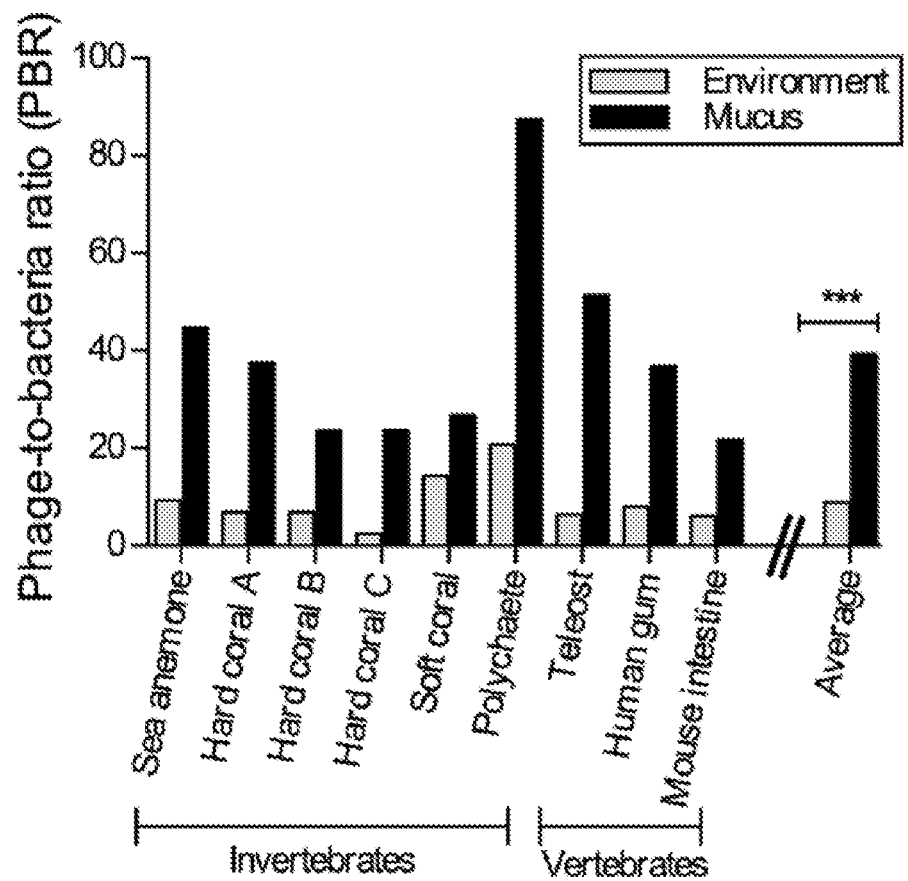
FIG. 1a, FIG. 1b, FIG. 1c graphically illustrate data showing the effect of Phage adhering to the mucin glycoprotein in mucus layers.

Our preliminary investigations of mucosal surfaces suggested that phage concentrations in the mucus layer were elevated compared to the surrounding environment. Here we used epifluorescence microscopy to count the phage and bacteria in mucus, sampled from a diverse range of mucosal surfaces (e.g., sea anemones, fish, human gum), and in each adjacent environment (FIG. S1). Comparing the calculated phage-to-bacteria ratios (PBRs) showed that PBRs in metazoan-associated mucus layers were on average 4.4-fold higher than those in the respective adjacent environment (FIG. 1A). The PBRs on these mucus surfaces ranged from 21:1 to 87:1 (average 39:1), as compared to 3:1 to 20:1 for the surrounding milieus (average 9:1, n=9, t=4.719 ***P=0.0002). Earlier investigations of phage abundance in marine environments reported that phage typically outnumber bacteria by an order of magnitude (49-51), but here we demonstrate that this margin was significantly larger in metazoan-associated mucus surface layers.

Figure 1B:
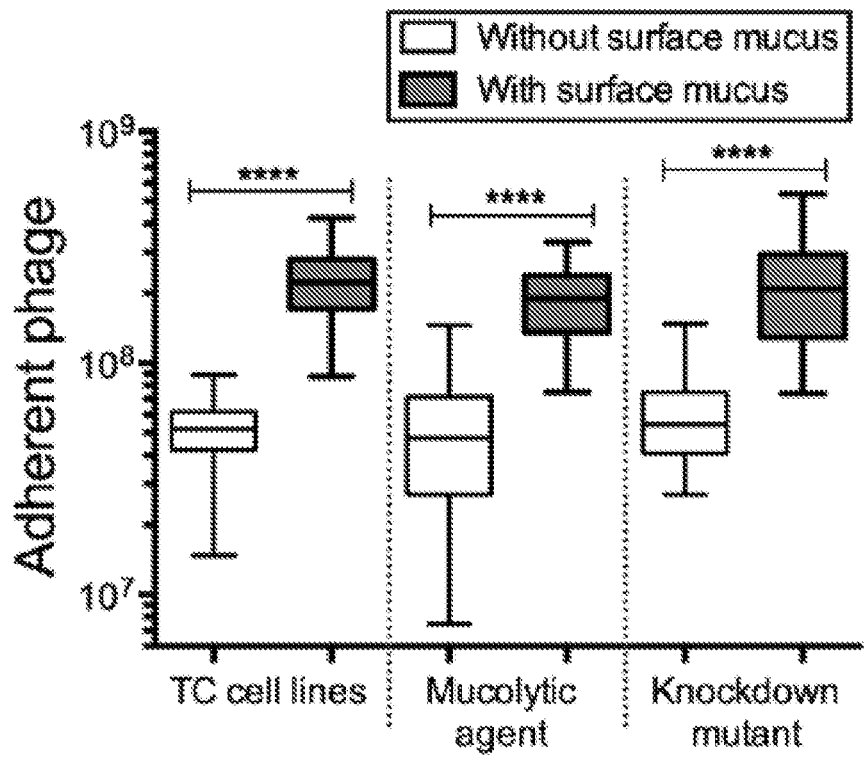

To determine if this enrichment was dependent on the presence of mucus rather than some general properties of the cell surface (e.g., charge), phage adherence was tested with tissue culture (TC) cells with and without surface mucus. In these assays, T4 phage were washed across confluent cell monolayers for 30 min, after which non-adherent phage were removed by repeated washings and the adherent phage quantified by epifluorescence microscopy. Two mucus-producing cell lines were used: T84 (human colon epithelial cells) and A549 (human lung epithelial cells). For these cells, mucin secretion was stimulated by pretreatment with phorbol 12-myristate-13-acetate (52, 53). Comparison of the T84 cells with the non-mucus-producing Huh-7 human hepatocyte cell line showed that T4 phage adhered significantly more to the mucus-producing T84 cells (FIG. 1B, n>18, t=8.366, **$P<0.0001$). To demonstrate the mucus-dependence of this adherence, the mucus layer was chemically removed from A549 cells by N-acetyl-L-cysteine (NAC) treatment (54) (FIG. S2). This significantly reduced the number of adherent phage to levels similar to those observed with non-mucus-producing cell lines (FIG. 1B, n>40, t=9.561, $P<0.0001$). Lastly, we created an A549 shRNA mucus knockdown cell line (MUC$^-$), reducing mucus production in A549, and a non-sense shRNA control (shConrol; FIGS. S3 and S4). Again, T4 phage adhered significantly more to the mucus-producing cells (FIG. 1B, n>37, t=7.673, **$P<0.0001$).

Figure 1C:
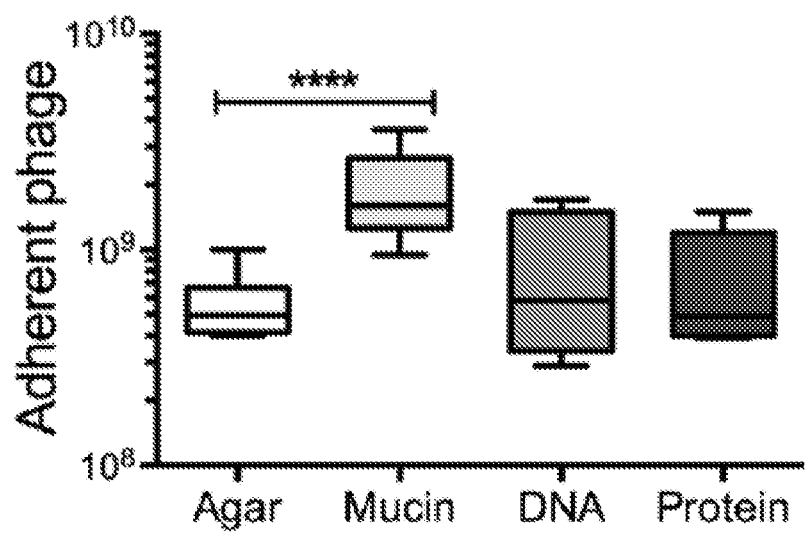

While mucin glycoproteins are the predominant component of mucus, other macromolecular components are also present, any of which might be involved in the observed phage adherence. We developed a modified top agar assay to determine whether phage adhered to a specific macromolecular component of mucus. Plain agar plates and agar plates coated with 1% (w/v) mucin, DNA, or protein were prepared. That concentration was chosen because it is at the low end of the range of physiological mucin concentrations (55). T4 phage suspensions were incubated on the plates for 30 min after which the phage suspension was decanted to remove unbound particles. The plates were then overlaid with a top agar containing E. coli hosts and incubated overnight. The number of adherent phage was calculated from the number of plaque forming units (PFU) observed. Significantly more T4 phage adhered to the 1% mucin-coated agar surface (FIG. 1c, n=12, t=5.306, ****$P<0.0001$). Combined, these three assays show that phage adhere to mucin glycoproteins.

Phage Adherence and Bacterial Infection

The mucus layer is an optimal environment for microbial growth, providing structure and access to a range of diverse mucin-associated glycans. To limit this growth the metazoan host retards microbial colonization by diverse antimicrobial mechanisms (23, 25-27). This raises the question of whether the increased number of adherent phage found on mucosal surfaces, provides the metazoan host with the benefit of reduced microbial colonization? To test this prediction, bacterial attachment to mucus-producing and non-mucus-producing TC cells was assayed both with and without pretreatment with the mucus-adherent phage T4. Here confluent monolayers of TC cells were overlaid with T4 phage for 30 min, washed to remove non-adherent phage, and then incubated with E. coli for 4 h. Cells were then scraped from the plates and attached bacteria were fluorescently stained and counted by epifluorescence microscopy. Phage pretreatment of mucus-producing TC cell lines (T84, A549) significantly decreased subsequent bacterial attachment (FIG. 2a, T84; n>30, t=32.05, **P<0.0001, A549; n>30, t=36.85, **P<0.0001). Comparatively, phage pretreatment of non-mucus producing cells (Huh-7; MUC⁻, an A549 mucus knockdown strain), resulted in less dramatic shifts in bacterial attachment. These results show that pretreatment of a mucosal surface with phage reduces adherence of a bacterial pathogen.

Figure 2B:
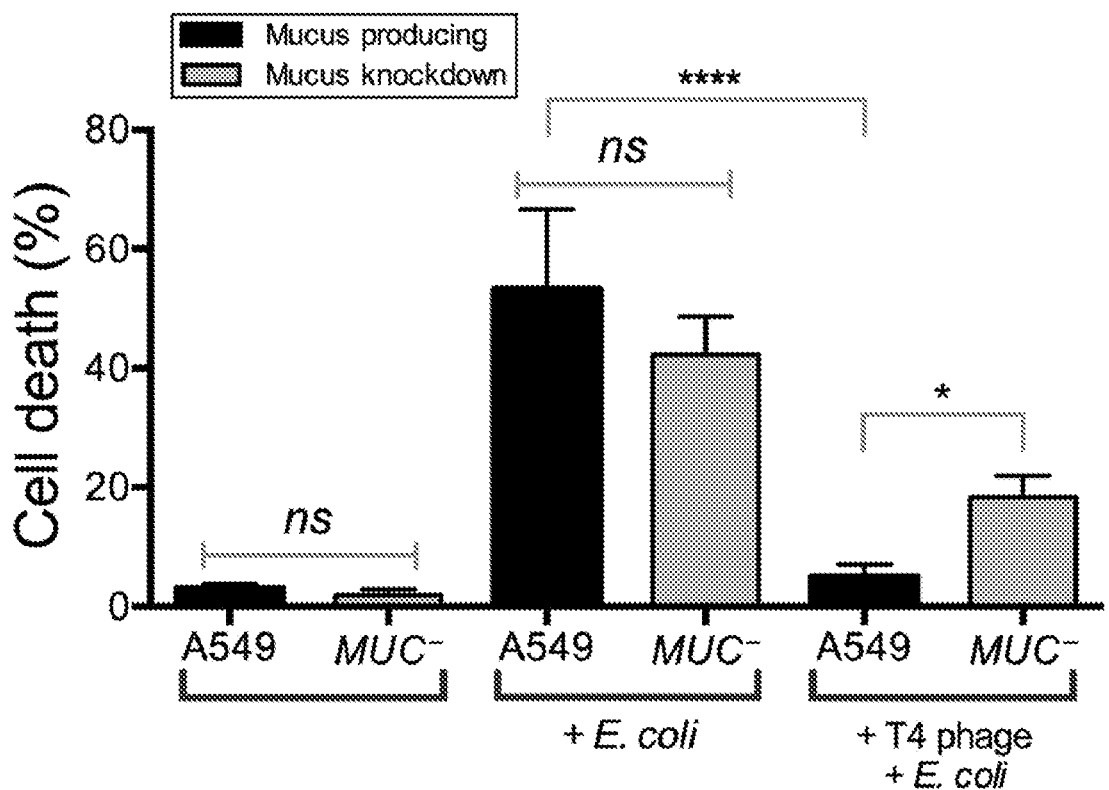

To test whether the observed reduced bacterial adherence was accompanied by reduced pathology of the underlying TC cells, mucus-producing A549 and non-mucus-producing MUC³¹ TC cells were exposed to *E. coli* overnight, either with or without a 30 min pre-treatment with T4 phage. Infection was quantified as the percentage of cell death. Adherence of phage effectively protected the mucus-producing cells against the subsequent bacterial challenge (FIG. 2*b*, *n*=12, ****P<0.0001). Phage pretreatment showed a reduced protection to the non-mucus-producing MUC⁻ cells against bacterial challenge, decreasing cell death by only 2-fold. Notably, phage pretreatment of mucus-producing A549 cells, relative to the non-mucus-producing MUC⁻ cells, resulted in a 3.6-fold greater reduction in cell death (n=12, *P=0.0181). Results show that mucin production significantly increased phage-associated protection of tissue culture cells, compared to mucin knockdown cell lines.

Role of Capsid Ig-Like Domains in Phage Adherence

Minot et al. recently reported that human gut-associated phage communities encode a diverse array of hypervariable proteins, including some with hypervariable Ig-like domains (43). T4 phage contain four Ig-like domains as part of the structural protein, Hoc, 155 copies of which are displayed on the phage capsid surface (56, 57). Based on this, and given that most Ig-like domains function in recognition and adhesion processes, we hypothesized that the T4 Hoc protein might mediate the adherence of T4 phage to mucus. To test this, the adherence of hoc+T4 phage and a hoc⁻ mutant to mucin-, DNA-, and protein-coated agar plates was compared to an agar control using the modified top agar assay (see above). Relative to plain agar, the adherence of hoc⁺ T4 phage increased 4.1-fold for mucin-coated agar (n>11, t=3.977, ***P=0.0007), whereas adherence increased only slightly for agar coated with DNA (1.1-fold) or protein (1.2-fold; FIG. 3*a*). Unlike the hoc⁺ T4 phage, the hoc⁻ phage did not show preferential adherence to the mucin-coated agar, with increased adherence of 1.2-, 1.2-, and 1.1-fold for mucin, DNA, and protein coatings, respectively. To ensure that none of the macromolecules directly affected phage infectivity, hoc⁺ and hoc⁻ T4 phage were incubated 1% (w/v) solutions of mucin, DNA, or BSA. Phage suspensions were combined with *E. coli* top agar as described above and layered over uncoated agar plates. The results confirmed that the macromolecules did not affect phage infectivity (FIG. S5). To further demonstrate the mucin adherence capability of other phage capsid displayed Ig-like domains, we repeated the modified top agar assay using Ig⁺ and Ig⁻ T3 phage. Results indicate a similar increase in adherence to mucin for the Ig⁺ T3 phage, while Ig⁻ T3 phage did not show this increase (FIG. S6).

Next a competition assay using hoc⁺ and hoc⁻ T4 phage and mucus producing TC cells was performed. Phage suspended in mucin solutions ranging from 0% to 5% (w/v), were washed over confluent layers of mucus-producing A549 TC cells and phage adherence assayed as described above. Adherence of hoc⁺ T4 phage, but not of hoc⁻ T4 phage, was reduced by mucin competition in a concentration-dependent manner (FIG. 3*b*).

Interaction of the Hoc protein domains displayed on the capsid surface with mucin glycoproteins could potentially affect the rate of diffusion of T4 virions in mucus. To evaluate this, we used multiple-particle tracking (MPT) to quantify transport rates of phage particles in buffer and in mucin suspensions. The ensemble average effective diffusivity ($D_{eff}$) calculated at a time scale of 1 s for both hoc⁺ and hoc⁻ T4 phage in buffer was compared against that in 1% (w/v) mucin suspensions. Both hoc⁺ and hoc phage diffuse rapidly through buffer (FIG. 3*c*). While hoc⁻ phage diffused in 1% mucin at the same rate as in buffer, the mucin decreased the diffusion rate for hoc⁺ phage particles 8-fold. Combined these three experiments support the hypothesis that the Hoc proteins displayed on the T4 phage capsid interact with mucin, thereby slowing phage diffusion in mucus and increasing phage mucosal residence time.

Phage Capsid Ig-Like Domains Interact with Glycans

Figure 4A:
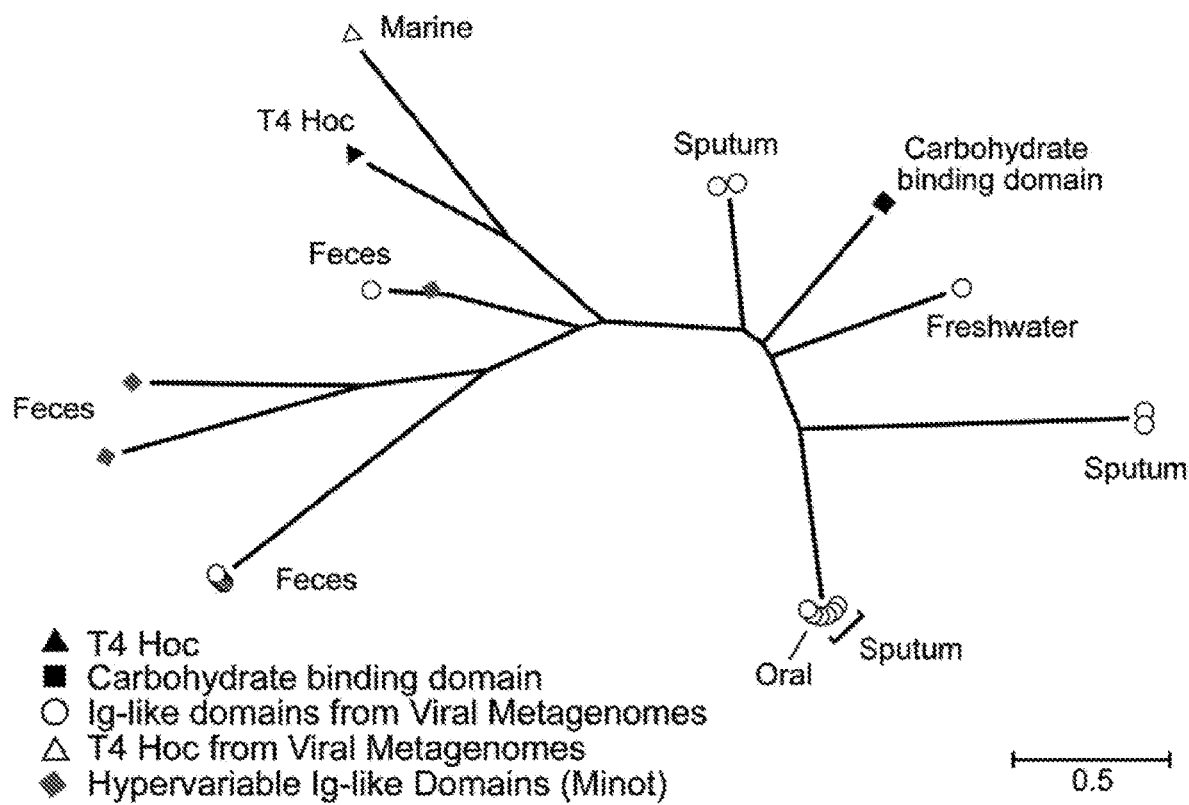
FIG. 4a and FIG. 4b graphically and schematically illustrate data showing Hoc-mediated glycan binding and Hoc-related phylogeny.
Figure 4B:
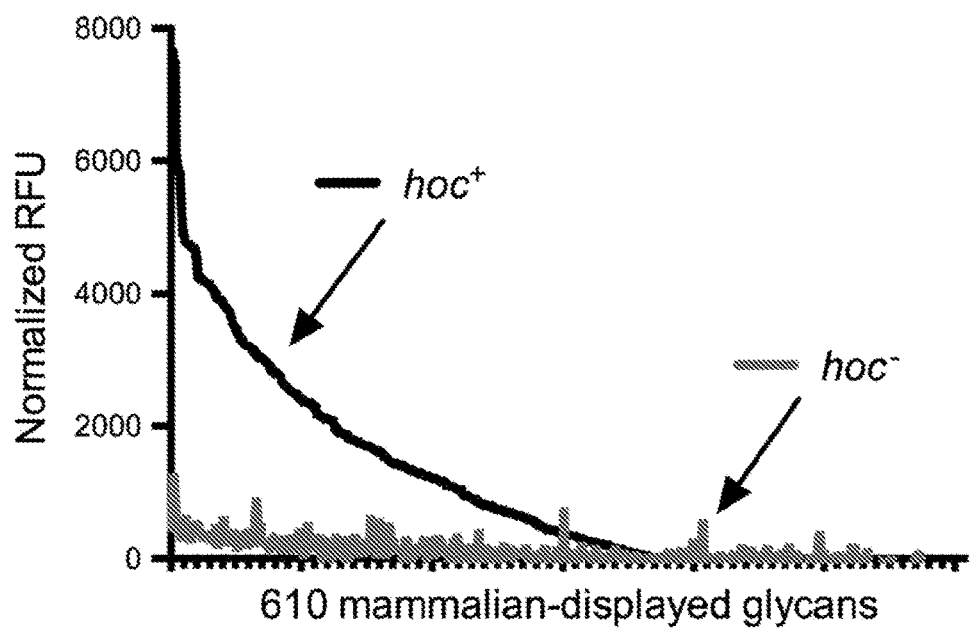

It is known that approximately 25% of sequenced tailed dsDNA phages (Caudovirales) encode structural proteins with predicted Ig-like domains (47). A search of publicly available viral metagenomes for homologs of the Ig-like domains of the T4 Hoc protein yielded numerous viral Ig-like domains from a variety of environments (FIG. 4*a*). These domains were more likely to be found in samples collected directly from mucus (e.g., sputum samples) or from an environment directly adjacent to a mucosal surface (e.g., intestinal lumen, oral cavity). All homologs displayed high structural homology (Phyre2 confidence score average 96±5%) with a plant-sugar binding domain known for its promiscuous carbohydrate binding specificity (Supplementary Methods and Table S1), suggesting an interaction between these Ig-like domains and glycans.

Mucins are complex glycoproteins with highly variable glycan groups exposed to the environment. To investigate whether Hoc interacts with glycans, and if so, to determine whether it interacts with a specific glycan or with a diverse array of glycans, we assayed phage adherence to microarrays printed with 610 mammalian glycans. While hoc⁺ T4 phage adhered to a large number of diverse glycans, they showed a preference for the O-linked glycan residues that are typically found in mucin glycoproteins (FIG. 4*b*; Table S2). The hoc⁻ T4 phage exhibited significantly lower affinity for all tested glycans. This indicates that Hoc mediates interactions between T4 phage and varied glycan residues.

Discussion

In diverse metazoans, body surfaces that interact with the environment are covered by a protective layer of mucus. These mucus layers provide favorable habitats for bacteria that serve as the point of entry for many pathogens but also support large populations of microbial symbionts. Also present are diverse phages that prey on specific bacterial hosts. Moreover, phage concentrations in mucus are elevated relative to the surrounding environment (an average 4.4-fold increase for a diverse sample of invertebrate and vertebrate metazoans; FIG. 1A). The increased concentration of lytic phage on mucosal surfaces provides a previously unrecognized metazoan immune defence effected by phage lysis of incoming bacteria.

Working with a model system employing T4 phage and various tissue culture (TC) cell lines, we demonstrated that the increased concentration of phage on mucosal surfaces is mediated by weak binding interactions between the variable Ig-like domains on the T4 phage capsid and mucin-displayed glycans. The immunoglobulin protein fold is well known for its varied but essential roles in the vertebrate immune response and cell adhesion. Ig-like domains are also present in approximately one quarter of the sequenced genomes of tailed DNA phages (47). Notably, these domains were found only in virion structural proteins and are typically displayed on the virion surface. Thus they were postulated to bind to bacterial surface carbohydrates during infection (47, 48). However, mucin glycoproteins, the predominant macromolecular constituent of mucus, display hundreds of variable glycan chains to the environment that offer potential sites for binding by phage Ig-like proteins. Furthermore, we speculate that phage utilize the variability of the Ig-like protein scaffold (supporting >$10^{13}$ potential alternatives) to adapt to the host's ever-changing patterns of mucin glycosylation.

The presence of an Ig-like protein (Hoc) displayed on the capsid of T4 phage significantly slowed the diffusion of the phage in mucin solutions. In vivo, similar phage binding to mucin glycans would increase phage residence time in mucus layers. Since bacterial concentrations are typically enriched in mucus, we predict that mucus-adherent phage are more likely to encounter bacteria, potentially increasing their replicative success. If so, phage Ig-like domains that bind effectively to the mucus layer would be under positive selection. Likely Hoc and other phage proteins with Ig-like domains interact with other glycans with different ramifications, as well (48, 57).

Previous metagenomic studies had documented the ubiquity and diversity of bacteria and phage within mucus-associated environments (e.g., human gut, human respiratory tract, corals) (51, 58-63). We had also become aware of some of the essential but adaptable services provided by symbiotic bacteria in these environments (McFall-Ngai et al., 2013). However, only recently have we begun to investigate the dynamic influences of phage within host-associated ecosystems (36, 43, 64). In this work, we used an in vitro model system to demonstrate a mechanism of phage adherence to the mucus layers that shield metazoan cells from the environmental. Further, adherent phage protected the underlying epithelial cells from bacterial infection. Based on these observations and previous research, we describe the Bacteriophage Adherence to Mucus (BAM) model of immunity in which the adherence of phage to mucosal surfaces yields a non-host-derived, antimicrobial defence. According to this model (summarized in FIG. 5), the mucus layer, already considered to be part of the innate immune system and known to provide physical and biochemical anti-microbial defences (15, 23, 65), also accumulates phage.

The model system we employed involved a single lytic phage and host bacterium. Within the mucosal layer reside diverse bacterial lineages and predictably an even greater diversity of phage strains enmeshed within complex phage-bacterial infection networks and engaged in a dynamic arms race (66, 67). These and other factors lower the probability that any given phage-bacterium encounter will result in a successful infection. The time dimension adds further complexity. The mucus layer is dynamic. Mucins are continually secreted by the underlying epithelium; mucus is continually sloughed from the outer surface. As a result, there is an ongoing turnover of both the bacterial and phage populations in the mucus layer. Driven by kill-the-winner dynamics, the population of phage types that can infect the dominant bacterial types present will cycle along with the populations of their hosts. Through such mechanisms we envision that adherent lytic phages provide a dynamic and adaptable defence for their metazoan hosts—the first example of a metazoan-phage symbiosis.

In summary, compositions and methods as provided herein, which can incorporate "BAM immunity", reduce bacterial pathogenesis and provide a previously unrecognized, mucosal immunity.

Materials and Methods

Bacterial and Phage Counts from Mucus and Environmental Samples

Samples of mucus and the adjacent environment were collected directly from nine evolutionarily-diverse mucosal surfaces (FIG. S1 and Table S1). Samples were transported and maintained on ice until processed. All samples were fixed overnight in 0.5% glutaraldehyde at 4° C., then incubated in 6.5 mM dithiothreitol (DTT) at 37° C. for one hour to assist mucus degradation. A 1-100 µl aliquot was diluted with 2 ml of 0.02 µm SM buffer, briefly mixed, then filtered onto a 0.02 µm anodisc polycarbonate filter (Whatman, Piscataway, NJ). Filters were stained with 10×SYBR Gold, washed, and visualized on a Zeiss epifluorescence microscope. For each sample, 20-30 images were taken for both bacteria and virus-like particles. Images were analyzed using Image Pro Plus 5.1 software (MediaCybernetics, Rockville, MD). Counts of bacteria and virus-like particles (referred to as "phage" throughout the text) per ml were made as previously described (68).

Phage Adherence to Mucus-Associated Macromolecules

LB agar plates were coated with 1 ml of 1% (w/v) of one of the following in 1×PBS: type III porcine stomach mucin, DNA from salmon testes, or bovine serum albumin (all three from Sigma-Aldrich, St. Louis, MO) and then allowed to dry. Stocks of hoc$^+$ and hoc$^-$ T4 phage ($10^9$ PFU ml$^{-1}$) were serially diluted to $1×10^{-7}$ and $1×10^{-8}$ per ml in LB, and a 5 ml aliquot of each dilution was washed across the plates for 30 min at 37° C. on an orbital shaker. After the phage suspensions were decanted from the plates, the plates were shaken twice to remove excess liquid and dried. Each plate was then layered with 1 ml of overnight E. coli culture ($10^9$ ml$^{-1}$) in 3 ml of molten top agar and incubated overnight at 37° C. The number of adherent phage was calculated from the number of plaque forming units (PFU) observed multiplied by the initial phage dilution. To determine if mucus macromolecules directly affected phage infectivity, hoc$^+$ and hoc$^-$ T4 phage ($10^9$ PFU ml$^{-1}$) were serially diluted as described above into 1 ml LB solutions containing 1% (w/v) mucin, DNA, or BSA. After incubation for 30 min at 37° C., the phage suspensions were combined with E. coli top agar as described above and layered over uncoated agar plates (FIG. S6).

Tissue Culture Cells and Mucus Reduction

Monolayers of various mucus-producing and non-mucus-producing tissue culture (TC) cells (Supplementary Methods) were grown to confluence in 6 well multi-well Tissue Culture plates (Becton Dickinson, Franklin Lakes, N.J.). (a) Mucus-producing TC cells were exposed to 1 µg/ml of a phorbol ester, phorbol-12-myristate-13-acetate (PMA: Sigma-Aldrich, St. Louis, Mo.) in the culture media overnight to stimulate the mucin secretory response (53). (b) The mucolytic agent N-acetyl-L-cysteine (NAC; Sigma-Aldrich, St. Louis, Mo.) was used to chemically remove mucus from A549 TC cells (60 mM NAC in serum-free media for 1 h with agitation) (54). Mucus depletion was confirmed using PAS/AB (FIG. S2). (c) A MUC-A549 cell line was produced by transduction of A549 cells with GIPZ™ Lentiviral Human MUC1 shRNA and TRIPZ™ Inducible Lentiviral Human MUC5AC shRNA as target vectors; a shControl A549 cell line was produced using the GIPZ™ Non-silencing Lentiviral shRNA Control as a control vector (Thermo Scientific, Waltham, Mass.; ). Knockdown of mucus production in the MUC-cell line was confirmed by Western blot analysis and periodic acid-Schiff-Alcian blue (PAS/AB; Sigma-Aldrich, St. Louis, Mo.; FIGS. S3 and S4).

Phage Treatment of TC Cells

TC cells were washed twice with 5 ml of serum-free media to remove residual antibiotics, layered with 2 ml of serum-free media containing T4 phage ($10^7$ or $10^9$ ml$^{-1}$), and incubated at 37° C. and 5% $CO_2$ for 30 min. Cells were then washed five times with 5 ml of serum-free media to remove non-adherent phage.

Phage Adherence to TC Cells

TC cells were treated with phage ($10^9$ ml$^{-1}$; see above), then scraped from plates using Corning Cell Scrapers (Sigma-Aldrich, St. Louis, MO). Adherent phage were counted by epifluorescence microscopy as described above.

Bacterial Adherence to TC Cells with/without Phage Pretreatment

TC cells, with or without pretreatment with T4 phage ($10^7$ ml$^{-1}$) were layered with 2 ml serum-free media containing E. coli ($10^7$ ml$^{-1}$), incubated at 37° C. and 5% $CO_2$ for 4 h, and then washed five times with 5 ml serum-free media to remove non-adherent phage and bacteria. Cells were scraped from plates and adherent phage and bacteria were counted by epifluorescence microscopy as described above.

TC Cell Death from Bacterial Infection

Mucus-producing A549 and MUC$^-$ A549 TC cells were grown to confluence. T4 phage were cleaned using Amicon 50™ kDa centrifugal filters (Millipore, Billerica, MA) and SM buffer to remove bacterial lysis products. Cells, with or without T4 phage pretreatment ($10^7$ ml$^{-1}$), were incubated with E. coli ($10^7$ ml$^{-1}$) overnight. Afterwards, TC cells were recovered from the plates by trypsin/EDTA solution (Invitrogen, Grand Island, NY). Cells were pelleted by centrifugation and resuspended in 1×PBS. Dead cells were identified by staining with 1 mg/ml of propidium iodide (Invitrogen, Grand Island, NY). Samples were then analyzed on a FACSCANTO II™ flow cytometer (BD Biosciences, San Jose, CA) with excitation at 488 nm and emission detected through a 670 LP filter. The forward scatter threshold (FSC) was set at 5,000 and a total of 10,000 events were collected for each sample.

Mucin Competition Assay

Mucus-producing A549 TC cells were grown to confluence. Hoc$^+$ and hoc$^-$ T4 phage ($10^9$ ml$^{-1}$) were diluted into mucin solutions ranging between 0% and 5% (w/v), then washed over TC cells for 30 min at 37° C. and 5% $CO_2$. Cells were washed five times with 5 ml serum-free media to remove non-adherent phage, scraped from plates, and adherent phage were quantified as described above.

Multiple Particle Tracking (MPT)

Assays were performed in plastic well chambers mounted on glass slides that had been coated with poly(dimethylsiloxane) (PDMS) to prevent phage adherence. 5 µl of 10 ml$^{-1}$ SYBR™ Gold-labelled phage suspensions were added to 50 µl of 1% (w/v) mucin solution in 1×PBS buffer. Trajectories of fluorescently labelled phage were observed using a DELTAVISION SPECTRIS™ Model DV4™ deconvolution microscope (Applied Precision, Issaquah, WA) equipped with a 100× Olympus PLANAPO 1.4™ lens. Movies were captured using SOFTWORX® 5.0.0 (Applied Precision, Issaquah, WA); 100 ms temporal resolution for 30 s; ten analyses per sample; n>100 particle trajectories per analysis. Trajectories were analyzed with the SPOTTRACKER™ 2D and 3D plugin for Image J (69). The coordinates of phage particle centroids were transformed into time-averaged mean square displacements (MSD): $<\Delta r^2(\tau)> = <\Delta x^2 + \Delta y^2>$, from which effective diffusivities ($<D_{eff}>$) were calculated; $D_{eff} = <\Delta r^2(\tau)>/(4\tau)$ (70, 71).

Glycan Microarray

Phage binding to glycans was assayed using printed mammalian glycan microarrays (version 5.1, Consortium for Functional Glycomics Core) containing 610 glycan targets. Samples of hoc$^+$ T4 phage, hoc$^-$ T4 phage, and buffer controls were applied to separate glycan microarray slides. Each slide received 35 µl of sample, 35 µl of binding buffer (Tris saline with 2 mM $Ca^{2+}$, 2 mM $Mg^{21}$, 1% BASE and 0.05% Tween 20), and a coverslip. Slides were incubated for 1 h at room temperature and washed with binding buffer. Slides were then incubated in SYBR GOLD™ fluorescence dye (diluted 1:10,000 in binding buffer) for 1 h under a coverslip at room temperature, washed, dried, and immediately scanned in a PerkinElmer PROSCANARRAY MICROARRAY SCANNER™ using an excitation wavelength of 488 nm. IMAGENE™ software (BioDiscovery, Inc., El Segundo, CA) was used to quantify fluorescence. Normalized relative fluorescence (RFU) values reported are the average (after subtraction of background buffer fluorescence) from six spots for each glycan represented on the array.

Graphing and statistics: Graphing and statistical analyses were performed using GRAPHPAD PRISM 6™ (GraphPad Software, San Diego, CA). All error bars represent 5-95% confidence intervals. The mid-line represents the median and the mean for box plots and bar plots, respectively.

Example 2: Exemplary Treatments

This example provides data demonstrating the efficacy of exemplary embodiments as provided herein, and, while the invention is not limited by any particular mechanism of action, this example provides exemplary mechanisms by which aspects as provided herein provide antibacterial protection to an individual in need thereof.

Here we tested a phage therapy application of the bacteriophage adherence to mucus (BAM) model on a life-like mucosal surface. Only mucus-adherent phage were capable of reducing bacterial colonization of the mucus layer, with non-adherent phages performing no better than when no phage were added. Diffusion experiments reveal that mucus-adherent phage exhibit continuous time random walk (CTRW) subdiffusive motion in mucus solutions, which theoretically predicts increased phage-bacteria encounters. Using the classical adsorption assay, we experimentally validated that the subdiffusive motion of phage is a more effective search strategy bacterial hosts within mucus. Here we demonstrate that phage are capable of mimicking complex search patterns that lead to increased encounter rates, effectively enabling phage to hunt their bacterial prey within mucosal surfaces. The evidence shown here proposes phage as the first predator known to utilize a subdiffusive search strategy, and, while the invention is not limited by any particular mechanism of action, further demonstrates the success of mucosal phage therapies provided herein.

In an attempt to understand the fundamental interactions occurring between phage and bacterial host within the context of the mucus layer, we developed a microfluidic system to simulate a life-like mucosal surface and test the phage therapy application of the BAM model (Barr, Auro, et al., 2013). Here we used the T4 phage model system, including the mucus-adherent T4 wild type phage (T4 wt), and the non-mucus-adherent, T4 Hoc knockout phage (T4 hoc$^-$)—a deletion mutant that does not contain the Hoc domain but is otherwise a normally infective T4 phage particle. Microfluidic chips allowed for the investigation of well-controlled phage and bacterial infections on a repeatable and standardized mucosal surface, with constant fluid-flow selectively amplifying microbial growth within the mucus layer.

We investigated how both mucus-adherent and non-adherent phages diffuse within simplified mucin solutions. Using the classical phage adsorption assay, we then tested two models of diffusion within relevant mucosal environments, and propose a potential therapeutic solution for the inconsistencies associated with mucosal phage therapy applications.

Phage Therapy within a Dynamic Mucosal Surface

A mucosal microfluidic device (chip) was designed to mimic the microenvironment of a mucosal surface, exhibiting constant fluid flow, physiological shear stress, and mucus secretion dynamics (McGuckin *et al.*, 2011). The chip was made of poly(dimethylsiloxane) (PDMS) and consisted of a single microfluidic channel, with in and out ports, attached to a glass microscope slide (FIGS. 1A & B, Example 2; or FIGS. 23A, 23B). Mucus-producing human lung epithelial cells were seeded into the channel, and allowed to attach to the glass surface. Tissue culture media was then perfused through at a flow rate of 40-100 $\mu L\ h^{-1}$ (0.02 dyne $cm^2$) to mimic the physiological fluid flow and shear stresses experienced by a mucosal surface (Kim et al., 2012; Ishikawa et al., 2011). Using a multiplex syringe-pump, up to nine of these chips were simultaneously fed with continual fluid-flow for seven days to allow the establishment of a confluent mucosal epithelium exhibiting mucus secretion and turnover dynamics (FIGS. 1C, D & E, Example 2; or FIGS. 23C, 23D and 23E). Using these chips we performed perfusion-based, phage and bacterial infection assays upon the in vitro mucosal surface. More specifically, the continually fluid-flow allowed us to selectively amplify the effects of microbial growth within the mucosal surface, as both contaminating growth from the surrounding milieu and sloughed mucus layers were constantly washed away and removed from the system.

FIG. 1, Example 2; or FIG. 23, schematically and graphically illustrates microfluidic devices (chip) designed to simulate a life-like in vitro mucosal surface, and their function, respectively. A) Schematic of chip design and measurements. B) Single chip bonded to a glass microscope slide with microfluidic tubing attached to in and out ports. C) Mucus-producing lung tissue cultured cells seeded into main channel. D) Cells in main after seven days of fluid flow and growth. E) Multiplex syringe pump running nine chips simultaneously. F) Phage therapy assay with phage and bacterial counts taken from the mucosal surface. G) Phage detachment rates from mucosal surface over a six hour period, dashed line indicates the 1 hr wash time point used in phage therapy assay.

One critical aspect of phage therapy that has never been effectively investigated in vitro is the treatment of such a dynamic and life-like mucosal surface. To investigate the tripartite interactions between phage-bacterium-mucosa, we treated chips with either the mucus-adherent T4 wt phage ($10^7\ mL^{-1}$), the non-adherent T4 hoc$^-$ phage ($10^7\ mL^{-1}$), or a no-phage control, for 24 hours in order to saturate the mucosal epithelium. Chips were then washed for one hour to remove phage not enmeshed within the mucus layer, followed by infection with *Escherichia coli* (*E. coli*) bacterial host ($10^7\ mL^{-1}$) at a multiplicity of infection (MOI) of 1. Following infection, chips were washed with phage- and bacterium-free media for 18 hours, allowing for microbial replication within the mucus layer. Chips were then sacked, the mucosal surface scraped, and the number of phage and bacteria present within the mucus layer was quantified by culturing (FIG. 1F, Example 2, or FIG. 23F). High phage abundances were detected in both the T4 wt and hoc$^-$ treatments, indicating that both phage populations were actively infecting and propagating with the *E. coli* bacterial host. Yet only the T4 wt treated chips showed a significant antimicrobial effect, with over a 4000-fold reduction in bacterial abundance within the mucus layer (n=5, t=; P<Barb stats to come). Comparatively, the T4 hoc treated chips showed no effective reduction in bacterial mucosal abundance compared to the no-phage control (n=5, t=; P=).

Why were only the mucus-adherent, T4 wt phage effective at reducing the bacterial load on the in vitro mucosal surface? The mucus layer is a complex, gel-like, network that traps and embeds both T4 wt and hoc$^-$ phage particles within it. Thus in an attempt to explain the differences in anti-bacterial protection, we investigated whether mucus-adherent T4 wt phage accumulated at higher abundance, or persisted for longer, within the chips mucosal surface, than the non-adherent T4 hoc phage (Barr, Auro, et al., 2013). Chips were again saturated with either T4 wt or hoc$^-$ phage ($10^7\ mL^{-1}$) for 24 hours, and then washed with phage- and bacterium-free media to quantify phage detachment from the mucosal surface over a six-hour period (FIG. 1G, Example 2, or FIG. 23G). Detachment of T4 wt and hoc$^-$ phage from the mucosal surface within the first hour were comparable, with the majority of both phages rapidly releasing from the mucus layer. At this point, a large portion of phage had detached from the mucosal surface, and the one-hour wash from the previous infection assay likely resulted in a MOI of significantly less than 1. The following five hours showed a much slower rate of detachment for both phage types, with slightly higher concentrations of T4 wt phage detaching from the mucosal surface. Results suggest that neither mucus-adherent phage accumulation, nor persistence within the mucosal surface were responsible for differences in antimicrobial protection. Thus the weak BAM mechanisms likely do not govern phage persistence within mucosal surface, and instead mucus secretion and turnover dynamics regulate mucosal phage abundances.

Bacteriophage Exhibit Subdiffusive Motion in Mucus.

In an attempt to elucidate the above-mentioned differences between T4 wt and hoc$^-$ phage within our mucosal surface, we employed high-speed multiple particle tracking (MPT) to track the diffusion of both phage types across a physiological range of homogenous mucin solutions. Fluorescence-labelled phage were mixed with 0% (buffer), 0.2%, 1%, and 5% mucin solutions (wt/vol) within a microscope slide well, and tracked at a temporal resolution of 43.5 ms. We manually tracked the diffusion of phage particles and calculated their diffusion constants ($\mu m^2/s$)(FIG. 2A, Example 2, or FIG. 24A) (Meijering et al., 2012).

Diffusion of both phage were comparable in 0% solutions, but T4 wt phage diffused 1.13 and 1.62 times slower than the T4 hoc$^-$ phage, in 0.2% and 1% mucin solutions respectively. These 10% mucin diffusion values are different from our previously reported results (Barr, Auro, et al., 2013), and are likely due to higher temporal resolution and improve MPT methodologies employed here. Interestingly at 5% mucin concentrations both T4 wt and hoc$^-$ phage particles were effectively 'trapped' in the mucin solution, with diffusion constants approaching our resolving power.

It is known that within complex fluids, such as the cellular cytoplasm or mucus gels, that diffusion can exhibit anomalous characteristics over time that are not defined by normal Brownian motion (Guigas & Weiss, 2008; Saxton, 2007). Enhancing diffusion results in superdiffusion, while subdiffusion is a result of hindrance or slowing. Normal diffusion is characterized by a MSD that grows linearly over time (t) with the diffusion constant (D); that is, MSD(τ)=Dτ. Comparatively, anomalous diffusion is characterized by the power-law exponent alpha (α), where MSD~τ$^α$. Simply put, normal diffusion is characterized by α=1, superdiffusion by α>1, and subdiffusion by α<1. Mucus-adherent phage binding to glycan residues displayed on the large mucin glycoproteins, slowing their diffusion through the mucus network, but this slowing may not be anomalous over time. To investigate whether T4 wt and hoc⁻ phage exhibit anomalous diffusion in mucus, we calculated their α-value of from our MPT experiments (FIG. 2B, Example 2, or FIG. 24B). All experimental conditions revealed normal diffusion (i.e., α≈1), with the exception of T4 wt phage in 0.2% and 1% mucin solutions, both showing a clear subdiffusive signal of α=0.94 and α=0.81, respectively.

FIG. 2, Example 2, or FIG. 24, graphically illustrates: A) Mucus-adherent T4 wt and non-adherent T4 hoc⁻ phage diffusion constants (μm²/s) in 0% (buffer), 0.2%, 1%, and 5% mucin solutions (wt/vol). B) Alpha value (α) measurements of T4 wt and T4 hoc⁻ phage in 0% (buffer), 0.2%, 1%, and 5% mucin solutions (wt/vol). Brownian diffusion α≈1, subdiffusion α<1.

Subdiffusion has been found to emerge from a wide variety of complex processes, including the intracellular transport of proteins, nucleic acids, and lipids. But the picture is not simple, with different models of subdiffusion having distinct biophysical effects. Next we calculated the ensemble-averaged MSD for all experimental conditions, with alpha values represented by the slope of the line of best fit showing a decreased slope for T4 wt phage in 0.2% and 1% mucin solutions (FIG. 3, Example 2, or FIG. 25). To elucidate the most appropriate model of sub-diffusion, we compared these results with a time-averaged MSD calculation, which revealed Brownian motion for both phages in all experimental conditions (α≈1). This ensemble-averaged aging effect, or weak ergodicity breaking, is the hallmark feature described by a continuous time random walk (CTRW) model (Ernst et al., 2014). According to the CTRW model of sub-diffusion, particles diffuse by Brownian motion, but are interrupted by periods of the particle becoming 'stuck' for periods of ever increasing time, which describes the aging process and mechanism of sub-diffusion. This explains why sub-diffusion is not observed for the T4 hoc⁻ phage, which is not able to adhere to mucins and therefore never becomes 'stuck' during its Brownian motion.

What is the biological relevance of phage sub-diffusion in mucus? Contrary to naïve expectations that slower diffusion results in lethargic reactions, sub-diffusion can actually dramatically increase the rate of biological encounters (Weiss & Nilsson, 2004; Höfling & Franosch, 2013). Subdiffusive particles take longer to diffuse away from their initial positions, and are more likely to retrace local regions than a freely diffusing particle (Weber et al., 2010). Thus a phage that diffuses normally could swiftly escape the mucus layer, while the subdiffusive phage is more likely to stay within the mucus layer for a longer period of time (Golding & Cox, 2006; Barkai et al., 2012).

Bacteriophage have Increased Adsorption with Bacterial Host in Mucus.

The search for a specific target is a ubiquitous process across biology. At the macroscopic scale we observe animals searching for food, at the microscopic, molecules and enzymes perform site-specific searches within a cell (Sims et al., 2008; Golding & Cox, 2006). Many predators possess prior knowledge of where prey is located, and can further utilize their senses—sight, touch, sound—to fine-tune the forage. But a bacteriophage possess no such knowledge or sense, and the search for a susceptible bacterial host becomes effectively 'blind'. Under such limitations, foraging success is largely dependent on the search strategy employed (Humphries *et al.*, 2012). It has been shown that many predators, ranging from microbes to humans, adopt a super-diffusive search strategy—called a Lévy flight—to optimize their success of random searches for food (Schuster & Levandowsky, 1996; Raichlen et al., 2014; Viswanathan et al., 1996). But when trying to apply such a search strategy to phage, we fall short. Phage have no locomotion, acting instead as colloidal particles rather than as predators capable of superdiffusive pursuit.

A critical and rate-limiting step in the phage life cycle is the extracellular search by a phage for a new bacterial host (Adams, 1959; Schlesinger, 1932). Phages ability to infect and reproduce within a bacterial host can be entirely predicted by equations describing the movement and adsorption of inert colloidal particles under Brownian motion (Stent, 1963; Schlesinger, 1932). These adsorption reactions are experimentally measured by mixing a phage with its bacterial host in a suspension, and following the disappearance of free phage as they collide with host cells, becoming irreversibly adsorbed to their surface, (Hyman & Abedon, 2009). These reactions are represented by adsorption constants (k), which are a function of bacterium and phage size, rate of phage diffusion, and likelihood of attachment upon collision, all of which are specific for a given phage-host pair (Stent, 1963). The model T4 phage has a widely reported and empirically determined adsorption constant of $2.4 \times 10^{-9}$ cm³/min, which can be used to theoretically calculate phage adsorption rates at a known bacterial density.

We experimentally tested phage subdiffusion in mucus as an optimal search strategy for a bacterial host. Adsorption assays of both the mucus-adherent T4 wt phage and non-adherent T4 hoc⁻ phage were performed under low bacterial densities in both 1% mucin (wt/vol) and control solutions. Briefly, *E. coli* ($1 \times 10^7$ mL⁻¹) was mixed with a control (0%) or 1% mucin solution, followed by the addition of either T4 wt or hoc⁻ phage ($2 \times 10^5$ mL⁻¹). Samples were then collected from these solutions every two minutes, followed by the addition of chloroform, effectively destroying all bacterial cells in the sample and stopping any further phage-host adsorptions. Adsorption assays were designed, based on the T4 phage k, so that ~22% of phages particles were theoretically adsorbed to a bacterial host over a 10-minute period. The mucus-adherent T4 wt phage adsorption to a bacterial host was significantly higher in 1% mucin solution than in the control (FIG. 4A, Example 2, or FIG. 26A; n=6, t=−3.89, **P=0.0037). Comparatively, the adsorption of the non-adherent T4 hoc⁻ phage to a bacterial host was not significantly different between the 1% mucin solution and the control (FIG. 4B, Example 2, or FIG. 26B; n=6, t=−1.33, P=0.22). Adsorption assays were repeated under higher bacterial densities ($7 \times 10^7$ mL⁻¹), so that ~80% of phage particles were adsorbed to a bacterial host over a 10-minute period. Interestingly, under higher bacterial densities the increased adsorption of T4 wt phage in 1% mucin solution was not apparent. It is known that as the density of phage and bacterial particles increases, so does their random chance of encounter (Stent, 1963). Thus we conclude that at higher phage and bacterial densities the benefit provided by a subdiffusive search strategy is masked by a high chance of random encounters. But at sufficiently low bacterial densities, and therefore low random chance of encounter with a bacterial host, subdiffusion in mucus provides an optimal search strategy for a bacteriophage. Thus by interacting with mucosal surfaces, phage can mimic complex search strategies, becoming effectual bacterial predators.

A Conceptual Model of Phage Adherence to Mucus.

We have proposed a bacteriophage adherence to mucus (BAM) model, whereby phage adhered to mucus, and demonstrated that this association reduced bacterial colonization and pathology (Barr, Auro, et al., 2013). Here we designed a life-like in vitro mucosal surface, with continual fluid-flow dynamics and mucus secretion, to test a phage therapy application of the BAM model. Only mucus-adherent phage were capable of protecting this surface from a bacterial infection, with the non-adherent phage performing no better than if no phage were added at all. Intriguingly, when we investigated the differences in phage detachment rates from the mucus layers, we saw little difference between our two phage types, leading us to hypothesize that these adherence mechanism do not influence phage accumulation or residence times in a life-like mucosal layers. Instead, it is likely that the continual secretion and sloughing of the mucus layer acts to regulate phage retention times, irrespective of BAM mechanisms. Such dynamics were not easily addressed in our previous study.

At the microscopic level, phage adherence to mucus is measured by a decrease or slowing in diffusion (Barr, Auro, et al., 2013). Upon detailed investigation, phage diffusion in mucus was revealed to be anomalous over short time frames, indicative of a continuous time random walk (CTRW) model of subdiffusion. The CTRW model suggests that phage diffuse normally in mucus until they encounter a mucin glycoprotein, which they remain stuck to for a random period of time (Barkai et al., 2012; Ernst et al., 2014). Thus those phages stuck within the mucus layer would not move far away from their initial positions (Metzler et al., 2009). This is an important realization. At low densities phage make poor predators, and this slow de-correlation of phage away from mucus layers acts to maintain locally higher phage densities around productive sites of infection (FIG. 5A of Example 2; or FIG. 27A). This affect is further amplified by the realization that mucus-adherent phage exhibit Brownian motion at both lower and higher mucin concentrations, driving phage toward an optimal mucosal locale that likely parallels their bacterial host niche. Yet this explanation alone is insufficient. The mucus layer is a dynamic, ever-outwardly expanding gradient of mucins, and phages aggregating within this optimal range will quickly find themselves sloughed away.

In order to visualize and understand phage subdiffusion, we must become the phage—now lost within a convoluted mucus network, trying to find an evasive bacterium of our own to infect (FIG. 5B of Example 2; or FIG. 27B). Afloat within this environment we notice our prey, a distant bacterium barging through the mucus network, quickly squirming away. Eventually we drift into a mucin glycoprotein—a boundlessly long fiber, forming a three-dimensional spider web, covered by thousands of hair-like glycan chains. Using the hundreds of immunoglobulin-like domains covering our capsid, we weakly grab hold of, and then release, one of these mucin glycans. At times we hold onto many glycans, grasping hold of the mucin fiber for ever-longer periods of time, slowly drifting along a mucin cable. This dance continues, until eventually an oblivious bacterium, stopping briefly to absorb a swath of glycans, crashes into the mucin we are a grasp. Seizing this chance encounter, we attack the bacterium, injecting our genetic material and quickly synthesizing phage proteins and nucleic acids. Eventually, we lyse the temporary bacterial host, releasing phage progeny back into the mucus network at higher concentrations. Many more phage now dance along the mucin fibers, encountering significantly more bacterial hosts than those competing phage that simply drift. Very quickly our mucus-adherent phage have become a swarm, completely coating the mucin fibers within the immediate vicinity. Like ticks in a grass field, our phage swarm catches progressively more bacteria as they brush past the mucin branches unaware.

The degree of subdiffusion can dramatically influence the time-course at which biological encounters take place. This mechanism has important and previously unrecognized implications for phage therapy. We demonstrate that only mucus-adherent phage were capable of reducing bacterial colonization of our in vitro mucosal surface, and correlate this with increased host adsorption as a result of subdiffusive motion. Although phage adherence to mucus only results in a small increased chance of any one phage finding a bacterial host, at large abundances this biological effect is dramatic. Here we apply methodologies to corroborate the connection between subdiffusion and the biophysical world, providing a much wanted subdiffusion experimental control (Höfling & Franosch, 2013; Saxton, 2012).

REFERENCES—EXAMPLE 1

1. Bäckhed F, Ley R E, Sonnenburg J L, Peterson D A, & Gordon J I (2005) Host-bacterial mutualism in the human intestine. *Science* 307(5717):1915-1920.
2. Dethlefsen L, McFall-Ngai M, & Relman D A (2007) An ecological and evolutionary perspective on human-microbe mutualism and disease. *Nature* 449(7164):811-818.
3. Clay K & Holah J (1999) Fungal endophyte symbiosis and plant diversity in successional fields. *Science* 285 (5434):1742-1744.
4. Douglas A (2008) Mycetocyte symbiosis in insects. *Biol Rev* 64(4):409-434.
5. Hooper L V, Midtvedt T, & Gordon J I (2002) How host-microbial interactions shape the nutrient environment of the mammalian intestine. *Annu Rev Nutr* 22(1): 283-307.
6. Hosokawa T, Koga R, Kikuchi Y, Meng X-Y, & Fukatsu T (2010) *Wolbachia* as a bacteriocyte-associated nutritional mutualist. *Proc Natl Acad Sci USA* 107(2):769-774.
7. Nyholm S V & McFall-Ngai M (2004) The winnowing: establishing the squid-*Vibrio* symbiosis. *Nat Rev Microbiol* 2(8):632-642.
8. Ruby E G (1996) Lessons from a cooperative, bacterial-animal association: the *Vibrio fischeri-Euprymna scolopes* light organ symbiosis. *Annu Rev Microbiol* 50(1):591-624.
9. Currie C R, Scott J A, Summerbell R C, & Malloch D (1999) Fungus-growing ants use antibiotic-producing bacteria to control garden parasites. *Nature* 398(6729): 701-704.
10. Kaltenpoth M, Göttler W, Herzner G, & Strohm E (2005) Symbiotic bacteria protect wasp larvae from fungal infestation. *Curr Biol* 15(5):475-479.
11. Sachs J L, Skophammer R G, & Regus J U (2011) Evolutionary transitions in bacterial symbiosis. *Proc Natl Acad Sci USA* 108(Supplement 2):10800-10807.
12. Stouthamer R, Breeuwer J, & Hurst G (1999) *Wolbachia pipientis*: microbial manipulator of arthropod reproduction. *Annu Rev Microbiol* 53(1):71-102.
13. Chow J, Lee S M, Shen Y, Khosravi A, & Mazmanian S K (2010) Host-Bacterial symbiosis in health and disease. *Adv Immunol* 107:243.

14. Cone R A (2009) Barrier properties of mucus. *Adv Drug Deliv Rev* 61(2):75-85.
15. Linden S, Sutton P, Karlsson N, Korolik V, & McGuckin M (2008) Mucins in the mucosal barrier to infection. *Mucosal Immunol* 1(3):183-197.
16. Clunes M T & Boucher R C (2007) Cystic fibrosis: the mechanisms of pathogenesis of an inherited lung disorder. *Drug Discov Today* 4(2):63-72.
17. Strugala V, Allen A, Dettmar P W, & Pearson J P (2003) Colonic mucin: methods of measuring mucus thickness. *Proc Nutr Soc* 62(01):237-243.
18. Garren M & Azam F (2011) Corals shed bacteria as a potential mechanism of resilience to organic matter enrichment. *ISME J*. 19. Button B, et al. (2012) A Periciliary Brush Promotes the Lung Health by Separating the Mucus Layer from Airway Epithelia. *Science* 337(6097):937-941.
20. Martens E C, Chiang H C, & Gordon J I (2008) Mucosal glycan foraging enhances fitness and transmission of a saccharolytic human gut bacterial symbiont. *Cell Host Microbe* 4(5):447-457.
21. Poulsen L K, et al. (1994) Spatial distribution of *Escherichia coli* in the mouse large intestine inferred from rRNA in situ hybridization. *Infect Immun* 62(11):5191-5194.
22. Hooper L V, Xu J, Falk P G, Midtvedt T, & Gordon J I (1999) A molecular sensor that allows a gut commensal to control its nutrient foundation in a competitive ecosystem. *Proc Natl Acad Sci USA* 96(17):9833-9838.
23. Schluter J & Foster K R (2012) The Evolution of Mutualism in Gut Microbiota Via Host Epithelial Selection. *PLoS Biol* 10(11):e1001424.
24. Sonnenburg J L, et al. (2005) Glycan foraging in vivo by an intestine-adapted bacterial symbiont. *Science* 307(5717):1955-1959.
25. Phalipon A, et al. (2002) Secretory component: a new role in secretory IgA-mediated immune exclusion in vivo. *Immunity* 17(1):107-115.
26. Raj P A & Dentino A R (2002) Current status of defensins and their role in innate and adaptive immunity. *FEMS Microbiol Lett* 206(1):9-18.
27. Vaishnava S, et al. (2011) The Antibacterial Lectin RegIII {gamma} Promotes the Spatial Segregation of Microbiota and Host in the Intestine. *Sci. STKE* 334(6053):255.
28. Gerken T A (2004) Kinetic modeling confirms the biosynthesis of mucin Core 1 (β-Gal (1-3) α-GalNAc-O-Ser/Thr) O-glycan structures are modulated by neighboring glycosylation effects. *Biochemistry* 43(14):4137-4142.
29. Jentoft N (1990) Why are proteins O-glycosylated? *Trends Biochem. Sci.* 15(8):291.
30. Schulz B L, et al. (2007) Glycosylation of sputum mucins is altered in cystic fibrosis patients. *Glycobiology* 17(7):698-712.
31. Rodriguez-Brito B, et al. (2010) Viral and microbial community dynamics in four aquatic environments. *ISME J* 4(6):739-751.
32. Thingstad T & Lignell R (1997) Theoretical models for the control of bacterial growth rate, abundance, diversity and carbon demand. *Aquat Microb Ecol* 13:19-27.
33. Groisman E A & Ochman H (1993) Cognate gene clusters govern invasion of host epithelial cells by *Salmonella typhimurium* and *Shigella flexneri*. *EMBO J* 12(10):3779.
34. Johansen B K, Wasteson Y, Granum P E, & Brynestad S (2001) Mosaic structure of Shiga-toxin-2-encoding phages isolated from *Escherichia coli* O157: H7 indicates frequent gene exchange between lambdoid phage genomes. *Microbiol* 147(7):1929-1936.
35. Willner D, et al. (2011) Metagenomic detection of phage-encoded platelet-binding factors in the human oral cavity. *Proc Natl Acad Sci USA* 108(Supplement 1):4547-4553.
36. Duerkop B A, Clements C V, Rollins D, Rodrigues J L M, & Hooper L V (2012) A composite bacteriophage alters colonization by an intestinal commensal bacterium. *Proc Natl Acad Sci USA* 109(43):17621-17626.
37. Furuse K, et al. (1983) Bacteriophage distribution in human faeces: continuous survey of healthy subjects and patients with internal and leukaemic diseases. *J Gen Virol* 64(9):2039-2043.
38. Weinbauer M G (2004) Ecology of prokaryotic viruses. *FEMS Microbiol Rev* 28(2):127-181.
39. Clokie M R, Millard A D, Letarov A V, & Heaphy S (2011) Phages in nature. *Bacteriophage* 1(1):31-45.
40. Moran N A, Degnan P H, Santos S R, Dunbar H E, & Ochman H (2005) The players in a mutualistic symbiosis: insects, bacteria, viruses, and virulence genes. *Proc Natl Acad Sci USA* 102(47):16919-16926.
41. Oliver K M, Degnan P H, Hunter M S, & Moran N A (2009) Bacteriophages encode factors required for protection in a symbiotic mutualism. *Science* 325(5943):992-994.
42. Roossinck M J (2011) The good viruses: viral mutualistic symbioses. *Nat Rev Microbiol* 9(2):99-108.
43. Minot S, Grunberg S, Wu G D, Lewis J D, & Bushman F D (2012) Hypervariable loci in the human gut virome. *Proc Natl Acad Sci USA*.
44. McMahon S A, et al. (2005) The C-type lectin fold as an evolutionary solution for massive sequence variation. *Nat Struct Mol Biol* 12(10):886-892.
45. Medhekar B & Miller J F (2007) Diversity-generating retroelements. *Curr Opin Microbiol* 10(4):388-395.
46. Halaby D & Mornon J P E (1998) The immunoglobulin superfamily: an insight on its tissular, species, and functional diversity. *J Mol Evol* 46(4):389-400.
47. Fraser J S, Yu Z, Maxwell K L, & Davidson A R (2006) Ig-like domains on bacteriophages: a tale of promiscuity and deceit. *J Mol Biol* 359(2):496-507.
48. Fraser J S, Maxwell K L, & Davidson A R (2007) Immunoglobulin-like domains on bacteriophage: weapons of modest damage? *Curr Opin Microbiol* 10(4):382-387.
49. Fuhrman J A (1999) Marine viruses and their biogeochemical and ecological effects. *Nature* 399(6736):541-548.
50. Danovaro R & Serresi M (2000) Viral density and virus-to-bacterium ratio in deep-sea sediments of the Eastern Mediterranean. *Appl Environ Microbiol* 66(5):1857-1861.
51. Breitbart M, et al. (2002) Genomic analysis of uncultured marine viral communities. *Proc Natl Acad Sci USA* 99(22):14250.
52. Hong D H, Petrovics G, Anderson W, Forstner J, & Forstner G (1999) Induction of mucin gene expression in human colonic cell lines by PMA is dependent on PKC-ε. *Am J Physiol Gastrointest Liver Physiol* 277(5):G1041-G1047.
53. Forstner G, Zhang Y, McCool D, & Forstner J (1993) Mucin secretion by T84 cells: stimulation by PKC, Ca2+, and a protein kinase activated by Ca2+ ionophore. *Am J. Physiol Gastrointest Liver Physiol* 264(6):G1096-G1102.

54. Alemka A, et al. (2010) Probiotic colonization of the adherent mucus layer of HT29MTXE12 cells attenuates *Campylobacter jejuni* virulence properties. *Infect Immun* 78(6):2812-2822.
55. Lieleg O, Vladescu I, & Ribbeck K (2010) Characterization of particle translocation through mucin hydrogels. *Biophys J* 98(9):1782-1789.
56. Sathaliyawala T, et al. (2010) Functional analysis of the highly antigenic outer capsid protein, Hoc, a virus decoration protein from T4-like bacteriophages. *Mol Microbiol* 77(2):444-455.
57. Fokine A, et al. (2011) Structure of the Three N-Terminal Immunoglobulin Domains of the Highly Immunogenic Outer Capsid Protein from a T4-Like Bacteriophage. *J Virol* 85(16):8141-8148.
58. Reyes A, et al. (2010) Viruses in the faecal microbiota of monozygotic twins and their mothers. *Nature* 466(7304):334-338.
59. Marhaver K L, Edwards R A, & Rohwer F (2008) Viral communities associated with healthy and bleaching corals. *Environ Microbiol* 10(9):2277-2286.
60. Willner D, et al. (2009) Metagenomic analysis of respiratory tract DNA viral communities in cystic fibrosis and non-cystic fibrosis individuals. *PLoS One* 4(10):e7370.
61. Wegley L, Edwards R, Rodriguez Brito B, Liu H, & Rohwer F (2007) Metagenomic analysis of the microbial community associated with the coral Porites astreoides. *Environ Microbiol* 9(11):2707-2719.
62. Willner D, et al. (2012) Case studies of the spatial heterogeneity of DNA viruses in the cystic fibrosis lung. *Am J Respir Cell Mol Biol* 46(2):127.
63. Eckburg P B, et al. (2005) Diversity of the human intestinal microbial flora. *Science* 308(5728):1635-1638.
64. Minot S, et al. (2011) The human gut virome: Inter-individual variation and dynamic response to diet. *Genome Res* 21(10):1616-1625.
65. Lieleg O, Lieleg C, Bloom J, Buck C B, & Ribbeck K (2012) Mucin Biopolymers As Broad-Spectrum Antiviral Agents. *Biomacromolecules* 13(6):1724-1732.
66. Labrie S J, Samson J E, & Moineau S (2010) Bacteriophage resistance mechanisms. *Nat Rev Microbiol* 8(5):317-327.
67. Weitz J S, et al. (2012) Phage-bacteria infection networks. *Trends Microbiol*.
68. Patel A, et al. (2007) Virus and prokaryote enumeration from planktonic aquatic environments by epifluorescence microscopy with SYBR Green I. *Nat Protoc* 2(2):269-276.
69. Sage D, Neumann F R, Hediger F, Gasser S M, & Unser M (2005) Automatic tracking of individual fluorescence particles: application to the study of chromosome dynamics. *IEEE Trans Image Process* 14(9):1372-1383.
70. Suh J, Dawson M, & Hanes J (2005) Real-time multiple-particle tracking: applications to drug and gene delivery. *Adv Drug Deliv Rev* 57(1):63-78.
71. Lai S K, et al. (2007) Rapid transport of large polymeric nanoparticles in fresh undiluted human mucus. *Proc Natl Acad Sci USA* 104(5):1482.

REFERENCES—EXAMPLE 2

Abedon S T, Kuhl S J, Blasdel B G, Kutter E M. (2011). Phage treatment of human infections. *Bacteriophage* 1:66-85.
Adams M H. (1959). Bacteriophages. Interscience: New York, N.Y.
Atuma C, Strugala V, Allen A, Holm L. (2001). The adherent gastrointestinal mucus gel layer: thickness and physical state in vivo. *Am J Physiol Gastrointest Liver Physiol* 280:G922-929.
Babalova E G, Katsitadze K T, Sakvarelidze L A, Imnaishvili N S, Sharashidze T G, Badashvili V A, et al. (1968). [Preventive value of dried dysentery bacteriophage]. *Zh Mikrobiol Epidemiol Immunobiol* 45:143-5.
Barkai E, Garini Y, Metzler R. (2012). Strange kinetics of single molecules in living cells. *Phys Today* 65:29.
Barr J J, Auro R, Furlan M, Whiteson K L, Erb M L, Pogliano J, et al. (2013). Bacteriophage adhering to mucus provide a non-host-derived immunity. *Proc Natl Acad Sci* 110:10771-10776.
Barr J J, Youle M, Rohwer F. (2013). Innate and acquired bacteriophage-mediated immunity. *Bacteriophage*.
Bettarel Y, Bouvier T, Nguyen H, Pham T. (2014). The versatile nature of coral-associated viruses. *Environ Microbiol Rep*.
Brüssow H. (2005). Phage therapy: the *Escherichia coli* experience. *Microbiology* 151:2133-40.
Carlton R M. (1999). Phage therapy: Past history and future prospects. *Arch Immunol Ther Exp (Warsz)* 47:267-274.
Chibani-Chennoufi S, Sidoti J, Bruttin A, Kutter E, Sarker S, Brüssow H. (2004). In vitro and in vivo bacteriolytic activities of *Escherichia coli* phages: implications for phage therapy. *Antimicrob Agents Chemother* 48:2558-69.
d'Hérelle F. (1921). The bacteriophage: its role in immunity. Vol. 1. Masson.
Dabrowska K, Switala-Jelén K, Opolski A, Górski A. (2006). Possible association between phages, Hoc protein, and the immune system. *Arch Virol* 151:209-15.
Dethlefsen L, Huse S, Sogin M L, Relman D A. (2008). The pervasive effects of an antibiotic on the human gut microbiota, as revealed by deep 16S rRNA sequencing. Eisen, J A (ed). *PLoS Biol* 6:e280.
Dutilh B E, Cassman N, McNair K, Sanchez S E, Silva G G Z, Boling L, et al. (2014). A highly abundant bacteriophage discovered in the unknown sequences of human faecal metagenomes. *Nat Commun* 5.
Ernst D, Köhler J, Weiss M. (2014). Probing the type of anomalous diffusion with single-particle tracking. *Phys Chem Chem Phys* 16:7686-91.
Fokine A, Chipman P R, Leiman P G, Mesyanzhinov V V, Rao V B, Rossmann M G. (2004). Molecular architecture of the prolate head of bacteriophage T4. *Proc Nat Acad Sci USA* 101:6003-8.
Fraser J S, Yu Z, Maxwell K L, Davidson A R. (2006). Ig-like domains on bacteriophages: a tale of promiscuity and deceit. *J Mol Biol* 359:496-507.
Golding I, Cox E. (2006). Physical Nature of Bacterial Cytoplasm. *Phys Rev Lett* 96:098102.
Guigas G, Weiss M. (2008). Sampling the cell with anomalous diffusion—the discovery of slowness. *Biophys J* 94:90-4.
Höfling F, Franosch T. (2013). Anomalous transport in the crowded world of biological cells. *Rep Prog Phys* 76:046602.
Humphries N E, Weimerskirch H, Queiroz N, Southall E J, Sims D W. (2012). Foraging success of biological Lévy flights recorded in situ. *Proc Natl Acad Sci USA* 109:7169-74.
Hyman P, Abedon S T. (2009). Practical methods for determining phage growth parameters.

Ishikawa T, Sato T, Mohit G, Imai Y, Yamaguchi T. (2011). Transport phenomena of microbial flora in the small intestine with peristalsis. *J Theor Biol* 279:63-73.

Johansson M E V, Larsson J M H, Hansson G C. (2011). The two mucus layers of colon are organized by the MUC2 mucin, whereas the outer layer is a legislator of host-microbial interactions. *Proc Natl Acad Sci USA* 108 Suppl:4659-65.

Johansson M E V, Phillipson M, Petersson J, Velcich A, Holm L, Hansson G C. (2008). The inner of the two Muc2 mucin-dependent mucus layers in colon is devoid of bacteria. *Proc Natl Acad Sci USA* 105:15064-9.

Kim H J, Huh D, Hamilton G, Ingber D E. (2012). Human Gut-on-a-Chip inhabited by microbial flora that experiences intestinal peristalsis-like motions and flow. *Lab Chip*.

Linden S K, Sutton P, Karlsson N G, Korolik V, McGuckin M a. (2008). Mucins in the mucosal barrier to infection. *Mucosal Immunol* 1:183-97.

Markoishvili K, Tsitlanadze G, Katsarava R, Glenn J, Sulakvelidze A. (2002). A novel sustained-release matrix based on biodegradable poly(ester amide)s and impregnated with bacteriophages and an antibiotic shows promise in management of infected venous stasis ulcers and other poorly healing wounds. Int J Dermatol 41:453-458.

*Maura* D, Morello E, du Merle L, Bomme P, Le Bouguénec C, Debarbieux L. (2011). Intestinal colonization by enteroaggregative *Escherichia coli* supports long-term bacteriophage replication in mice. *Environ Microbiol* 1-11.

McGuckin M A, Lindén S K, Sutton P, Florin T H. (2011). Mucin dynamics and enteric pathogens. *Nat Rev Microbiol* 9:265-78.

Meijering E, Dzyubachyk O, Smal I. (2012). Methods for cell and particle tracking. *Methods Enzymol* 504:183-200.

Metzler R, Koren T, Brock B van den, Wuite G J L, Lomholt M A. (2009). And did he search for you, and could not find you? *J Phys A Math Theor* 42:434005.

Perez-Vilar J, Hill R L. (1999). The Structure and Assembly of Secreted Mucins. *J Biol Chem* 274:31751-31754.

Raichlen D A, Wood B M, Gordon A D, Mabulla A Z P, Marlowe F W, Pontzer H. (2014). Evidence of Levy walk foraging patterns in human hunter-gatherers. *Proc Natl Acad Sci USA* 111:728-33.

Sarker S A, McCallin S, Barretto C, Berger B, Pittet A-C, Sultana S, et al. (2012). Oral T4-like phage cocktail application to healthy adult volunteers from Bangladesh. *Virology* 434:222-32.

Saxton M J. (2007). A biological interpretation of transient anomalous subdiffusion. I. Qualitative model. *Biophys J* 92:1178-91.

Saxton M J. (2012). Wanted: a positive control for anomalous subdiffusion. *Biophys J* 103:2411-22.

Schlesinger M. (1932). Adsorption of phages to homologous bacteria. II. Quantitative investigations of adsorption velocity and saturation. Estimation of the particle size of the bacteriophage. *Z Hyg Infekt* 114:149-160.

Schuster F L, Levandowsky M. (1996). Chemosensory Responses of *Acanthamoeba castellanii*: Visual Analysis of Random Movement and Responses to Chemical Signals. *J Eukaryot Microbiol* 43:150-158.

Sekirov I, Tam N M, Jogova M, Robertson M L, Li Y, Lupp C, et al. (2008). Antibiotic-induced perturbations of the intestinal microbiota alter host susceptibility to enteric infection. *Infect Immun* 76:4726-36.

Sims D W, Southall E J, Humphries N E, Hays G C, Bradshaw C J A, Pitchford J W, et al. (2008). Scaling laws of marine predator search behaviour. *Nature* 451:1098-102.

Slopek S, Weber-Dabrowska B, Dabrowski M, Kucharewicz-Krukowska A. (1987). Results of bacteriophage treatment of suppurative bacterial infections in the years 1981-1986. *Arch Immunol Ther Exp (Warsz)* 35:569-83.

Smith H W, Huggins M B, Shaw K M. (1987). The control of experimental *Escherichia coli* diarrhoea in calves by means of bacteriophages. *J Gen Microbiol* 133:1111-26.

Stent G S. (1963). Molecular biology of bacterial viruses. Freeman and Company, San Francisco, Calif.

Sulakvelidze A, Alavidze Z, Morris J G. (2001). Bacteriophage therapy. *Antimicrob Agents Chemother* 45:649-59.

Tariq M A, Everest F L C, Cowley L, De Soyza A, Holt G S, Bridge S H, et al. (2015). A Metagenomic approach to characterize temperate bacteriophage populations from cystic fibrosis and non-cystic fibrosis bronchiectasis patients. *Front Microbiol* 6.

Viswanathan G M, Afanasyev V, Buldyrev S V., Murphy E J, Prince P A, Stanley H E. (1996). Lévy flight search patterns of wandering albatrosses. *Nature* 381.

Weber S C, Spakowitz A J, Theriot J A. (2010). Bacterial Chromosomal Loci Move Subdiffusively through a Viscoclastic Cytoplasm. *Phys Rev Lett* 104:238102.

Weiss M, Nilsson T. (2004). In a mirror dimly: tracing the movements of molecules in living cells. *Trends Cell Biol* 14:267-73.

Wright A, Hawkins C H, Anggård E E, Harper D R. (2009). A controlled clinical trial of a therapeutic bacteriophage preparation in chronic otitis due to antibiotic-resistant *Pseudomonas aeruginosa*; a preliminary report of efficacy. *Clin Otolaryngol* 34:349-57.

A number of embodiments of the invention have been described. Nevertheless, it will be understood that various modifications may be made without departing from the spirit and scope of embodiments as provided herein. Accordingly, other embodiments are within the scope of the following claims.

What is claimed is:

1. A method for:
   treating, ameliorating and preventing a microbial or a bacterial infection in an individual in need thereof,
   increasing or decreasing an effective dose of a probiotic, a prebiotic, a postbiotic or a synbiotic;
   increasing or decreasing efficacy of a probiotic, a prebiotic, a postbiotic or a synbiotic attaching to mucosal surfaces;
   increasing or decreasing access of a probiotic, a prebiotic, a postbiotic or a synbiotic to mucosal surfaces;
   increasing or decreasing chance of an enteral or gastrointestinal pathogenic infection or disease; or
   increasing or decreasing resistance of a probiotic, a prebiotic, a postbiotic or a synbiotic to temperature, pH, mechanical stress, osmotic stress and/or gastrointestinal enzymes,
   comprising:
   administering, feeding or applying to an individual in need thereof:
   (a) a product of manufacture, a food, a feed, a drink, a nutraceutical, formulation, a pharmaceutical or a pharmaceutical preparation comprising or having contained therein a composition;
   (b) a delivery vehicle, a product of manufacture, a container, a syringe, a device or an implant comprising or having contained therein a composition; or (c) a liquid, a suspension, a gel, a geltab, a semisolid, a tablet, a sachet, a lozenge, a capsule, a freeze-dried composition, an infant formula, an enteral or parenteral formulation, comprising: or having contained therein a composition, wherein the composition comprises:

a plurality of isolated, or substantially purified intact Caudovirales bacteriophages adherent or bound to mucins or negatively charged glycans on a surface of:

(i) an isolated or substantially purified: milk lipid, milk fat globule (MFG) macromolecule, or a mixture thereof;

(ii) an isolated plasma membrane, or isolated component of a plasma membrane, (iii) a hydrogel, (iv) a biocompatible crosslinked degradable thiol-ene polymer, or (v) any combination thereof, by binding or adhering the Caudovirales bacteriophages to the mucins or negatively charged glycans, wherein all of (i) to (iv) comprise and express on their surfaces the mucins or negatively charged glycans.

2. The method of claim 1, wherein the mucins comprise a membrane-tethered, membrane-integrated or secreted mucin.

3. The method of claim 1, wherein the negatively charged glycans comprise: an O-linked glycosylated glycan, or the glycan comprises an O-linked GalNAc or an N-linked glycosylation.

4. The method of claim 2, wherein the mucins comprise a MUC1, MUC3A, MUC3B, MUC4, MUC10, MUC11, MUC12, MUC13, MUC14, MUC15, MUC16, MUC17, MUC18, MUC20, MUC21, MUC2, MUC5AC, MUC5B, MUC6, MUC7, MUC8, MUC9 or MUC19 or any combination thereof.

5. The method of claim 1, wherein the Caudovirales bacteriophage are formulated per dose, or per serving, or per unit dosage at, or at a total daily dose of: between about $10^1$ and $10^{20}$ plaque-forming units (PFUs), or between about $10^3$ and $10^{17}$ PFUs, or between about $10^5$ and $10^{12}$ PFUs, or between about $10^7$ and $10^9$ PFUs.

6. The method of claim 1, wherein the composition further comprises a pharmaceutically acceptable excipient.

7. The method of claim 1, wherein the composition is formulated for administration in vivo; or for enteral or parenteral administration, or for ophthalmic, topical, oral, intranasal, intrarectal, intravaginal, intravenous, intra-peritoneal, intraocular, intra-placental, intra-bladder, cutaneous, intravenous (IV), intramuscular (IM), intrathecal, subcutaneous (SC), intracerebral, epidural, intracranial or rectal administration, or by inhalation.

8. The method of claim 1, wherein the composition is formulated or manufactured as or placed or formulated into:

(a) a tablet, a pill, a capsule, a gel, a geltab, a liquid, a powder, a suspension, a syrup, an emulsion, a lotion, an ointment, an aerosol, a spray, a lozenge, an ophthalmic preparation, an aqueous or a sterile or an injectable solution, or a patch, (b) an implant, a dietary supplement, an ice cream, an ice, a yogurt, a cheese, an infant formula or infant dietary supplement, a pasteurized milk or milk product or milk-comprising product; or (c) a veterinary formulation or feed.

9. The method of claim 1, wherein the composition further comprises or has added to:

a flavoring or a sweetening agent, an aspartamine, a stevia, monk fruit, a sucralose, a saccharin, a cyclamate, a xylitol, a vanilla, an artificial vanilla or chocolate or strawberry flavor, an artificial chocolate essence, or a mixture or combination thereof;

a preservative, a benzoic acid, a potassium sorbate;

at least one probiotic or prebiotic at least one anti-inflammatory agent; or an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, or a pharmaceutically acceptable excipient, a sweetening agent, a debittering agent, a flavoring agent, a pH stabilizer, an acidifying agent, a preservative, a desweetening agent and/or coloring agent, vitamin, mineral and/or dietary supplement, an antacid or a prebiotic nutrient.

10. The method of claim 1, wherein the composition is formulated as a delayed or gradual enteric release composition or formulation.

11. The method of claim 1, wherein the isolated, or substantially purified milk fat globule (MFG) macromolecule has a particle size between about: 1 nm to 100 nm, 100 nm to 1000 nm, 1 um to 100 um, or 100 um to 1000 um.

12. The method of claim 1, wherein the isolated, or substantially purified milk fat globule (MFG) macromolecule comprises between about 0.01% to 1%, or between about 1% to 20% of the composition.

13. The method of claim 1, wherein the individual in need thereof is a mammal.

14. The method of claim 13, wherein the mammal is a human, or a human infant.

15. The method of claim 1, wherein an antacid or a buffer or buffering agent or a pharmaceutically acceptable excipient is administered before, during or after, or before and during, administration of the composition.

16. The method of claim 15, wherein an antacid, a buffer or a buffering agent is administered to raise the pH of the stomach in the individual to between about 2.5 and 7, or between about 3 and 6.5, or to about 5.0, 5.5, 6.0, 6.5, 6.8 or 7.0.

17. The method of claim 16, wherein the buffer or the buffering agent or the pharmaceutically acceptable excipient comprises an inorganic salt, a citric acid, a sodium chloride, a potassium chloride, a sodium sulfate, a potassium nitrate, a sodium phosphate monobasic, a sodium phosphate dibasic or combinations thereof.

18. The method of claim 16, wherein the antacid comprises a calcium carbonate, a magnesium hydroxide, a magnesium oxide, a magnesium carbonate, an aluminum hydroxide, a sodium bicarbonate or a dihydroxyaluminum sodium carbonate.

19. The method of claim 1, wherein the isolated, or substantially purified milk lipid or milk fat globule (MFG) macromolecule is derived from a mammalian milk.

20. The method of claim 1, wherein the plasma membrane, or component of a plasma membrane:

(a) is reconstituted as a globular particle and/or (b) comprises a bacterial plasma membrane, or component of a bacterial plasma membrane.

21. The method of claim 1, wherein the bacterial infection is caused by a gram negative bacteria or a gram positive bacteria, or the bacterial infection is an MSRA infection, or the bacterial infection is caused by a *Staphylococcus*, a *Staphylococcus aureus*, a *Clostridium*, or a *Clostridium difficile*, *Escherichia coli*, a *Shigella*, a *Salmonella*, a *Campylobacter*, a *Cholerae Chloerae*, a *Bacillus*, or a *Yersinia*.

22. The method of claim 8, wherein the patch is a transdermal patch or a medicated adhesive patch.

23. The method of claim 1, wherein:
   (a) the Caudovirales bacteriophages are adherent to the surface of the isolated or substantially purified: the milk lipid, the milk fat globule (MFG) macromolecule, or the mixture thereof,
   (b) the Caudovirales bacteriophages are adherent to the surface of the plasma membrane or isolated component of the plasma membrane,
   (iii) the Caudovirales bacteriophages are adherent to the surface of the hydrogel, or
   (iv) the Caudovirales bacteriophages are adherent to the surface of the biocompatible crosslinked degradable thiol-ene polymer.

24. The method of claim 1, wherein the Caudovirales bacteriophages comprise or have contained on or therein a payload.

25. The method of claim 24, wherein the payload is capable of treating, ameliorating or preventing the infection.

26. The method of claim 9, wherein
   (a) the prebiotic comprises an inulin, lactulose, extracts of artichoke, chicory root, oats, barley, various legumes, garlic, kale, beans or flacks or an herb, at least one congealing agent,
   (b) the congealing agent comprises an arrowroot or a plant starch, a powdered flour, a powdered potato or potato starch, an absorbant polymer, a corn flour or a corn starch;
   (c) at least one inflammatory agent comprises or is an NSAID, a 4 or a 5-amino-salicylate, an olsalazine, a mesalazine, a sulfasalazine, a balsalazide, or an equivalent thereof or a combination thereof;
   (d) the buffer or a buffering agent or the pharmaceutically acceptable excipient comprises an inorganic salt, a citric acid, a sodium chloride, a potassium chloride, a sodium sulfate, a potassium nitrate, a sodium phosphate monobasic, a sodium phosphate dibasic or combinations thereof; or
   (e) the antacid comprises a calcium carbonate, a magnesium hydroxide, a magnesium oxide, a magnesium carbonate, an aluminum hydroxide, a sodium bicarbonate or a dihydroxyaluminum sodium carbonate; or any combination thereof.

27. The method of claim 16, wherein the antacid, buffer or buffering agent is administered before, during or after, or before and during, administration to raise the pH of the stomach in the individual to between about 2.5 and 7, or between about 3 and 6.5, or to about 5.0, 5.5, 6.0, 6.5, 6.8 or 7.0, and these pH values reached before, during or after, or before and during, administration.

28. The method of claim 20, wherein the globular particle has a size of between about: 1 nm to 100 nm, 100 nm to 1000 nm, 1 um to 100 um, or 100 um to 1000 um.

* * * * *